(12) United States Patent
Prammer et al.

(10) Patent No.: US 6,825,659 B2
(45) Date of Patent: Nov. 30, 2004

(54) METHOD AND APPARATUS FOR NUCLEAR MAGNETIC RESONANCE MEASURING WHILE DRILLING

(75) Inventors: Manfred G. Prammer, Downingtown, PA (US); James H. Dudley, Downingtown, PA (US); Peter Masak, West Chester, PA (US); George D. Goodman, Phoenixville, PA (US); Marian Morys, Downingtown, PA (US); Dale A. Jones, Houston, TX (US); Roger P. Bartel, Houston, TX (US); Chen-Kang David Chen, Houston, TX (US); Michael L. Larronde, Houston, TX (US); Paul F. Rodney, Spring, TX (US); John E. Smaardyk, Houston, TX (US)

(73) Assignee: Numar, Exton, PA (US)

( * ) Notice: Subject to any disclaimer, the term of this patent is extended or adjusted under 35 U.S.C. 154(b) by 0 days.

(21) Appl. No.: 10/603,073

(22) Filed: Jun. 24, 2003

(65) Prior Publication Data

US 2004/0124837 A1 Jul. 1, 2004

Related U.S. Application Data

(63) Continuation of application No. 10/108,182, filed on Mar. 27, 2002, now Pat. No. 6,583,621, which is a continuation of application No. 09/919,129, filed on Jul. 31, 2001, which is a continuation of application No. 09/232,072, filed on Jan. 15, 1999, now Pat. No. 6,268,726.
(60) Provisional application No. 60/071,612, filed on Jan. 16, 1998, and provisional application No. 60/071,699, filed on Jan. 16, 1998.

(51) Int. Cl.$^7$ ................................. G01V 3/00

(52) U.S. Cl. ........................ 324/303; 324/300

(58) Field of Search ..................... 324/303, 309, 324/300

(56) References Cited

U.S. PATENT DOCUMENTS 1,158,959 A    11/1915    Beach
3,205,477 A     9/1965    Kalbfell (List continued on next page.)

FOREIGN PATENT DOCUMENTS

EP    0 581 666 A3    2/1994    ............ G01V/3/32
EP    0 649 035 B1    4/1995    ............ G01V/3/32

OTHER PUBLICATIONS

International Publication No. WO 98/25164, Publication Date Jun. 11, 1998; from International Application No. PCT/US97/21889, Filed Nov. 26, 1997; Priority Data: Ser. No. 08/759,829, Filed Dec. 4, 1996.

(List continued on next page.)

*Primary Examiner*—Brij B. Shrivastav
(74) *Attorney, Agent, or Firm*—Jones Day

(57) ABSTRACT

A method for manufacturing NMR measurement-while-drilling tool having the mechanical strength and measurement sensitivity to perform NMR measurements of an earth formation while drilling a borehole, and a method and apparatus for monitoring the motion of the measuring tool in order to take this motion into account when processing NMR signals from the borehole. The tool has a permanent magnet with a magnetic field direction substantially perpendicular to the axis of the borehole, a steel collar of a non-magnetic material surrounding the magnet, antenna positioned outside the collar, and a soft magnetic material positioned in a predetermined relationship with the collar and the magnet that helps to shape the magnetic field of the tool. Due to the non-magnetic collar, the tool can withstand the extreme conditions in the borehole environment while the borehole is being drilled. Motion management apparatus and method are employed to identify time periods when the NMR measurements can be taken without the accuracy of the measurement being affected by the motion of the tool or its spatial orientation.

8 Claims, 38 Drawing Sheets

U.S. PATENT DOCUMENTS

| | | | |
|---|---|---|---|
| 3,213,357 A | 10/1965 | Brown et al. | |
| 3,360,716 A | 12/1967 | Bloom et al. | |
| 3,395,337 A | 7/1968 | Varian | |
| 3,402,344 A | 9/1968 | Brown et al. | |
| 3,453,433 A | 7/1969 | Alger et al. | 250/83.3 |
| 3,508,438 A | 4/1970 | Alger et al. | 73/152 |
| 3,567,935 A | 3/1971 | Nagel | 250/83.1 |
| 3,567,936 A | 3/1971 | Tittman | 250/83.1 |
| 3,590,228 A | 6/1971 | Burke | 235/151.35 |
| 3,593,116 A | 7/1971 | Culpepper | 324/0.5 |
| 3,617,867 A | 11/1971 | Herzog | 324/0.5 |
| 3,638,484 A | 2/1972 | Tixier | 73/152 |
| 3,657,730 A | 4/1972 | Robinson et al. | 324/0.5 |
| 3,667,035 A | 5/1972 | Slichter | 324/0.5 R |
| 3,777,560 A | 12/1973 | Gulgnard | 73/151.5 |
| 3,784,898 A | 1/1974 | Darley et al. | 324/0.5 R |
| 3,896,668 A | 7/1975 | Anderson et al. | 73/152 |
| 4,310,887 A | 1/1982 | Suau | 364/422 |
| 4,528,508 A | 7/1985 | Vail, III | 324/303 |
| 4,686,364 A | 8/1987 | Herron | 250/256 |
| 4,710,713 A | 12/1987 | Taicher et al. | 324/303 |
| 4,717,876 A | 1/1988 | Masi et al. | 324/303 |
| 4,717,877 A | 1/1988 | Taicher et al. | 324/303 |
| 4,717,878 A | 1/1988 | Taicher et al. | 324/303 |
| 4,728,892 A | 3/1988 | Vinegar et al. | 324/309 |
| RE32,913 E | 4/1989 | Clark | 324/338 |
| 4,885,540 A | 12/1989 | Snoddy et al. | 324/318 |
| 4,933,638 A | 6/1990 | Kenyon et al. | 324/303 |
| 5,055,787 A | 10/1991 | Kleinberg et al. | 324/303 |
| 5,055,788 A | 10/1991 | Kleinberg et al. | 324/303 |
| 5,122,746 A | 6/1992 | King et al. | 324/307 |
| 5,212,447 A | 5/1993 | Paltiel | 324/300 |
| 5,280,243 A | 1/1994 | Miller | 324/303 |
| 5,309,098 A | 5/1994 | Coates et al. | 324/303 |
| 5,349,184 A | 9/1994 | Wraight | 250/266 |
| 5,350,925 A | 9/1994 | Watson | 250/269.3 |
| 5,363,041 A | 11/1994 | Sezginer | 324/303 |
| 5,376,884 A | 12/1994 | Sezginer | 324/303 |
| 5,379,216 A | 1/1995 | Head | 364/422 |
| 5,381,092 A | 1/1995 | Freedman | 324/303 |
| 5,387,865 A | 2/1995 | Jerosch-Herold et al. | 324/303 |
| 5,412,320 A | 5/1995 | Coates | 324/303 |
| 5,432,446 A | 7/1995 | Macinnis et al. | 324/303 |
| 5,486,761 A | 1/1996 | Sezginer | 324/303 |
| 5,486,762 A | 1/1996 | Freedman et al. | 324/303 |
| 5,497,087 A | 3/1996 | Vinegar et al. | 324/303 |
| 5,498,960 A | 3/1996 | Vinegar et al. | 324/303 |
| 5,517,115 A | 5/1996 | Prammer | 324/303 |
| 5,557,200 A | 9/1996 | Coates | 324/303 |
| 5,557,201 A | 9/1996 | Kleinberg et al. | 324/303 |
| 5,565,775 A | 10/1996 | Stallmach et al. | 324/303 |
| 5,629,623 A | 5/1997 | Sezginer et al. | 324/303 |
| 5,680,043 A | 10/1997 | Hurlimann et al. | 324/303 |
| 5,705,927 A | 1/1998 | Sezginer et al. | 324/303 |
| 5,796,252 A | 8/1998 | Kleinberg et al. | 324/303 |
| 5,869,755 A | 2/1999 | Ramamoorthy et al. | 73/152.05 |
| 5,914,598 A | 6/1999 | Sezginer et al. | 324/303 |
| 5,977,768 A | 11/1999 | Sezginer et al. | 324/303 |
| 5,992,519 A | 11/1999 | Ramakrishnan et al. | 166/250.15 |
| 6,008,646 A | 12/1999 | Griffin et al. | 324/303 |
| 6,362,619 B2 * | 3/2002 | Prammer et al. | 324/303 |
| 6,583,621 B2 * | 6/2003 | Prammer et al. | 324/303 |

OTHER PUBLICATIONS

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Carr et al., "Effects of Diffusion on Free Precision in Nuclear Magnetic Resonance Experiments," *Physical Review*, vol. 94. No. 3 (May 1, 1954), pp. 630–638.

*Schlumberger Wireline & Testing*, "Combinable Magnetic Resonance tool reliably indicates water–free production and reveals hard–to–find pay zones," (Jun. 1995).

Morriss et al., "Field Test of an Experimental Pulsed Nuclear Magnetism Tool," SPWLA Annual Logging Symposium (Jun. 13–16, 1993), pp. 1–23.

Coates et al., "Core Data and the MRIL Show—A New Approach to 'Formation Factor,'" National SPWLA Convention (Jun. 15, 1992), pp. 1–15.

Kleinberg et al., "Novel NMR Apparatus for Investigating an External Sample," *Journal of Magnetic Resonance*, (1992) pp. 466–485.

Coates et al., "An Investigation of a New Magnetic Resonance Imaging Log," National SPWLA Convention (Jun. 18, 1991), pp. 1–24.

Howard et al., "Proton Magnetic Resonance and Pore–Size Variations in Reservoir Sandstones," *Society of Petroleum Engineers* (1990), pp. 733–741.

Miller et al., "Spin Echo Magnetic Resonance Logging: Porosity and Free Fluid Index Determination," *Society of Petroleum Engineers* (1990), pp. 321–334.

Kenyon et al., "Pore–Size Distribution and NMR in Microporous Cherty Sandstones," SPWLA Thirtieth Annual Logging Symposium (Jun. 11–14, 1989), pp. 1–24.

*Schlumberger Technology News—Oilfield Bulletin*, "Fifth Generation Nuclear Magnetic Resonance Logging Tool: A Major Advance in Producibility Measurement Technology," (Jul. 1995) (2 pp.).

Akkurt et al., "NMR Logging of Natural Gas Reservoirs," SPWLA 35th Annual Logging Symposium (Jun. 26–29, 1995).

Prammer, M.G., "NMR Pore Size Distributions and Permeability at the Well Site," *Society of Petroleum Engineers* (Sep. 25, 1995) pp. 55–64.

Chandler et al., "Improved Log Quality with a Dual–Frequency Pulsed NMR Tool," *Society of Petroleum Engineers* (1994) pp. 23–35.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Gallegos et al., "A NMR Technique for the Analysis of Pore Structure: Determination of Continuous Pore Size Distributions," Journal of Colloid and Interface Science, vol. 122, No. 1, Mar. 1988, pp. 143–153.

Gallegos et al., "A NMR Technique for the Analysis of Pore Structure: Application to Materials with Well–Defined Pore Structure," Journal of Colloid and Interface Science, vol. 119, No. 1, Sep. 1987, pp. 127–140.

Neuman et al., "Applications of Nuclear Magnetism Logging to Formation Evaluation," Journal of Petroleum Technology, vol. 34, (1982) pp. 2853–2862.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Jackson et al., "Western Gas Sands Project Los Alamos NMR Well Logging Tool Development," Los Alamos National Laboratory (Oct. 1981–Sep. 1982) pp. 1–28.

Clavier et al., "The Theoretical and Experimental Bases for the 'Dual Water' Model for the Interpretation of Shaly Sands," *Journal of Petroleum Technology* (Apr. 1984), pp. 3–15.

Petrakis et al., "The Utilization of Nuclear Magnetic Resonance Spectroscopy for Petroleum, Coal, Oil Shale, Petrochemicals, and Polymers, Phenomenology, Paradigms of Applications, and Instrumentation," 594 Applied Spectroscopy Reviews vol. 15 (1979) No. 2, pp. 195–260.

Brownstein et al., "Importance of classical diffusion in NMR studies of water in biological cells," The American Physical Society, vol. 19, No. 6, (1979) pp. 2446–2453.

Farrar et al., "Pulse and Fourier Transform NMR Introduction to Theory and Methods," Academic Press (1971) pp. 26–29.

Waxman et al., "Electrical Conductivities in Oil–Bearing Shaly Sands," *Society of Petroleum Engineers Journal* (1968) pp. 107–122.

Brown et al., "Nuclear Magnetism Logging," Transactions of the American Institute of Mining, Metallurgical, and Petroleum Engineers, vol. 219 (1960), pp. 199–207.

* cited by examiner

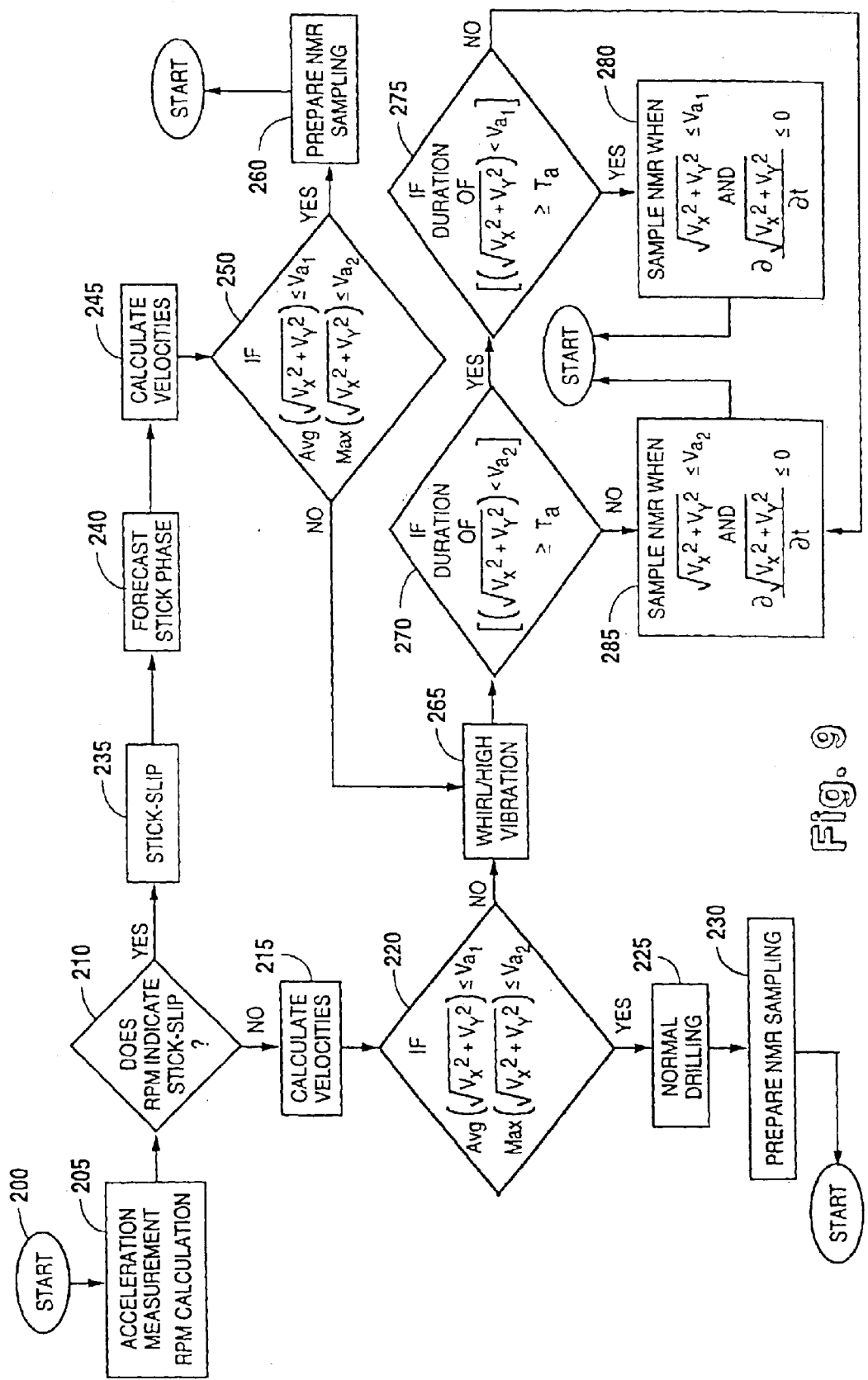

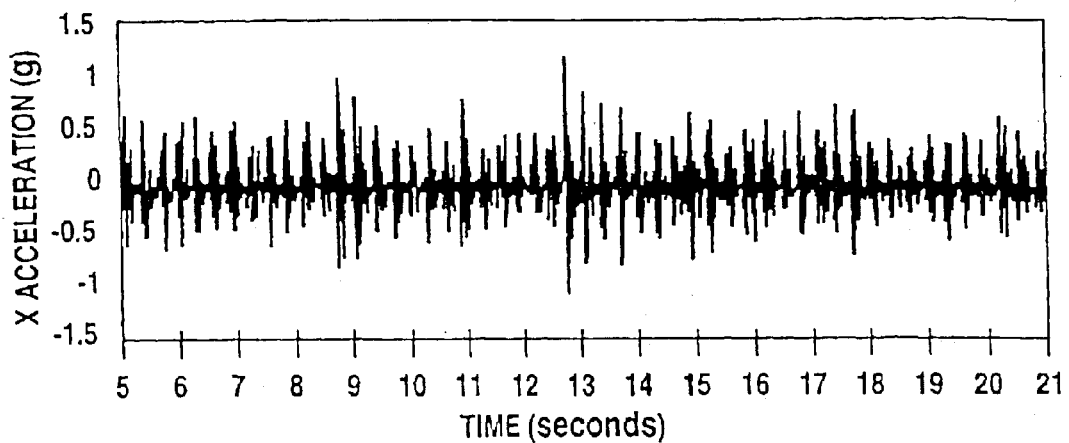
Fig. 10A1
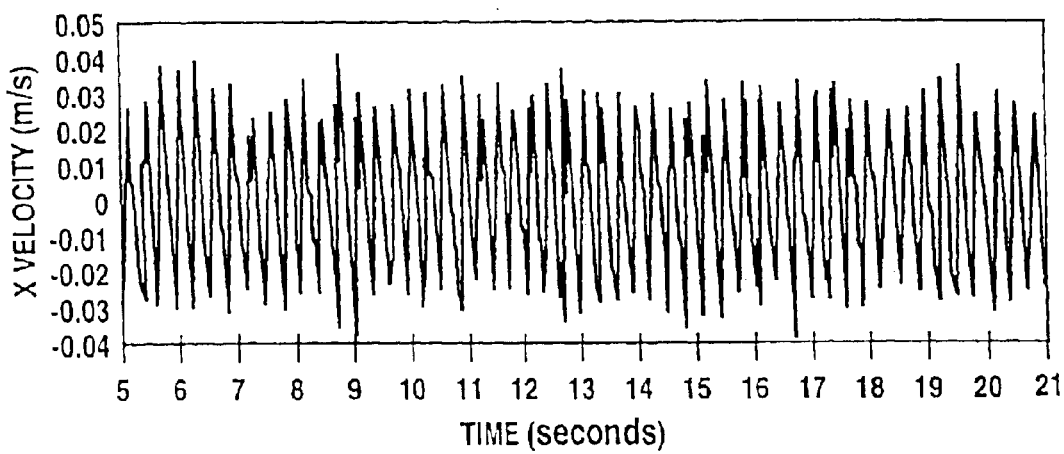
Fig. 10A2
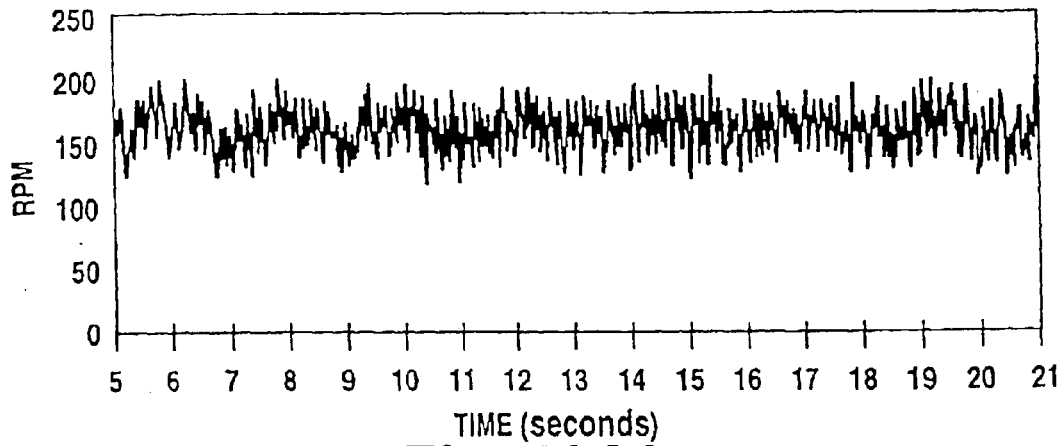
Fig. 10A3

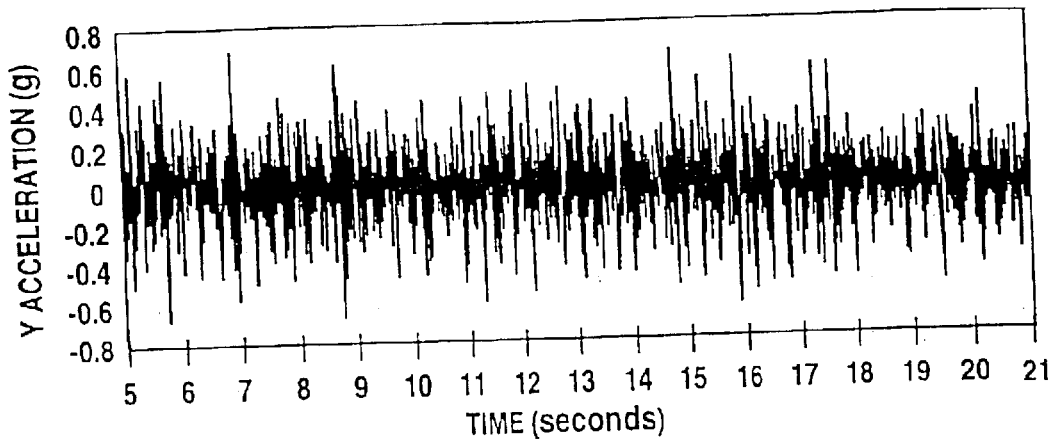
Fig. 10A4
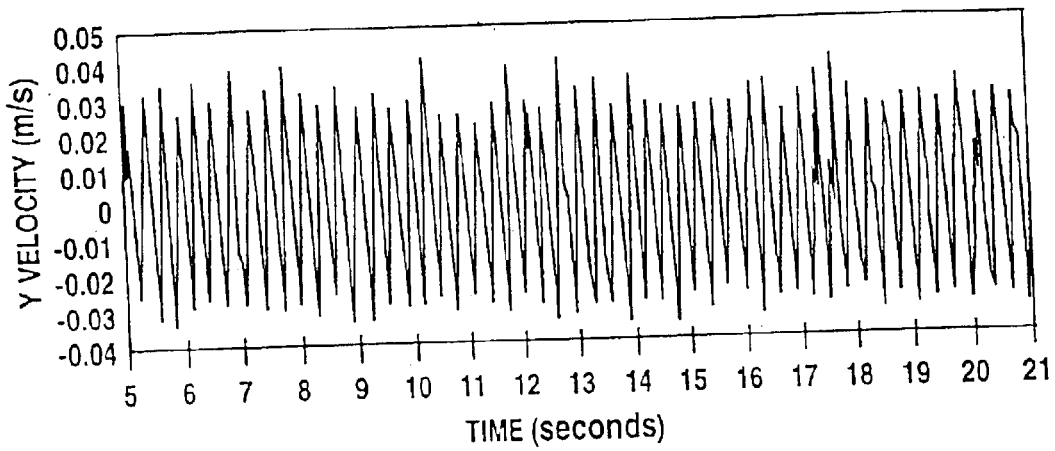
Fig. 10A5
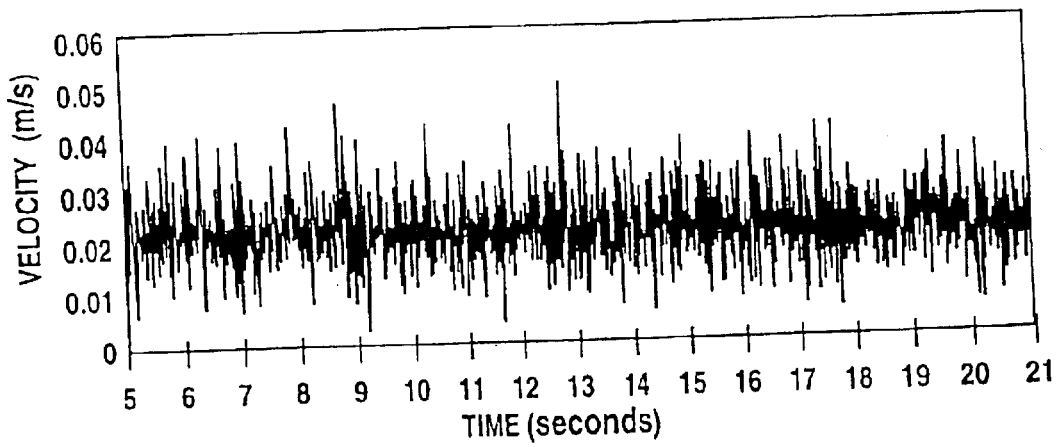
Fig. 10A6

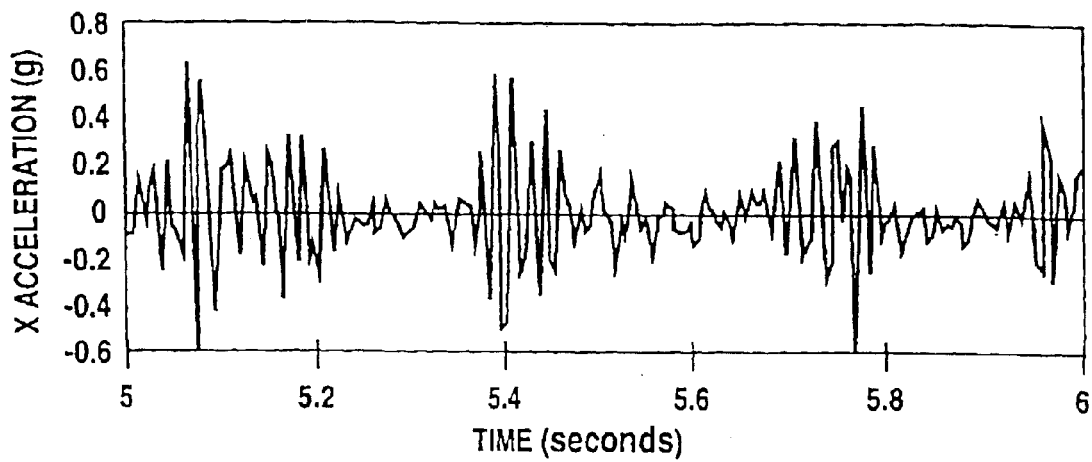
Fig. 10B1
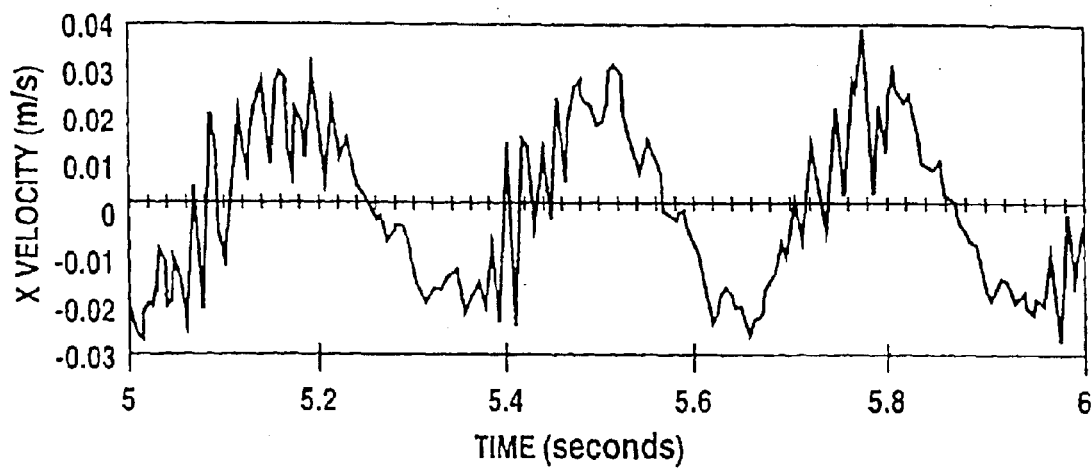
Fig. 10B2
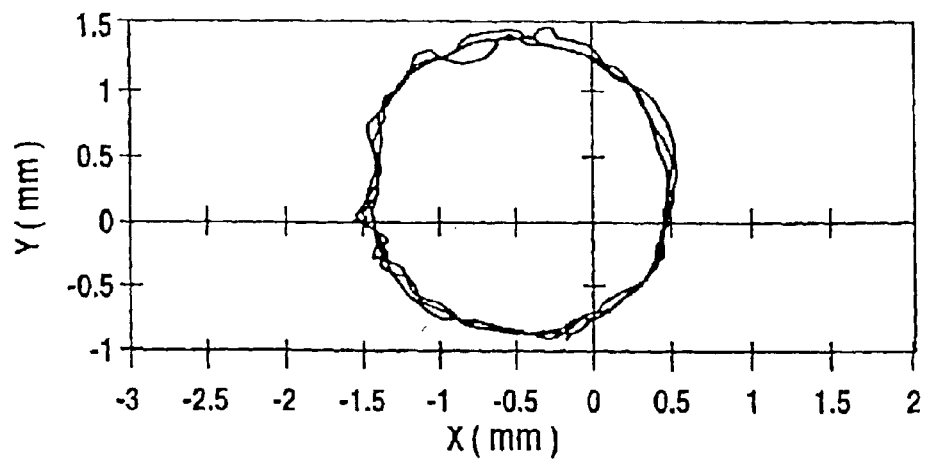
Fig. 10B3

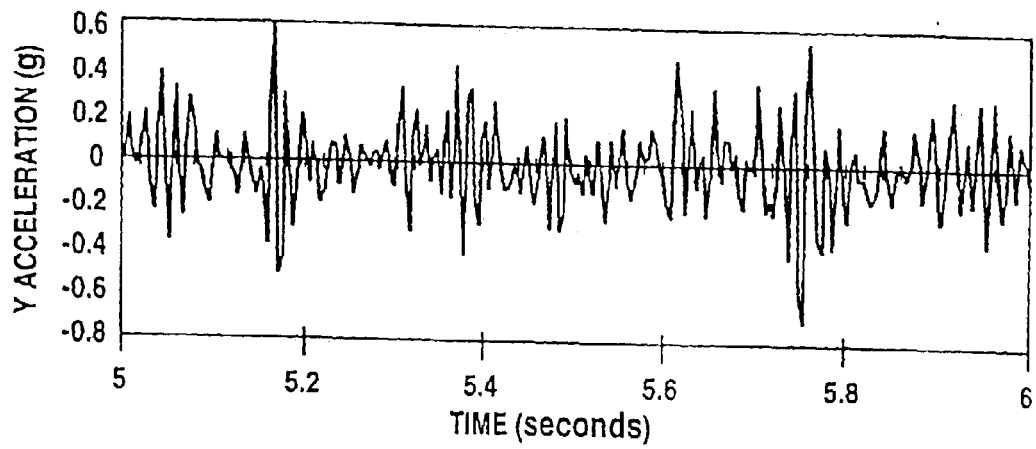
Fig. 10B4
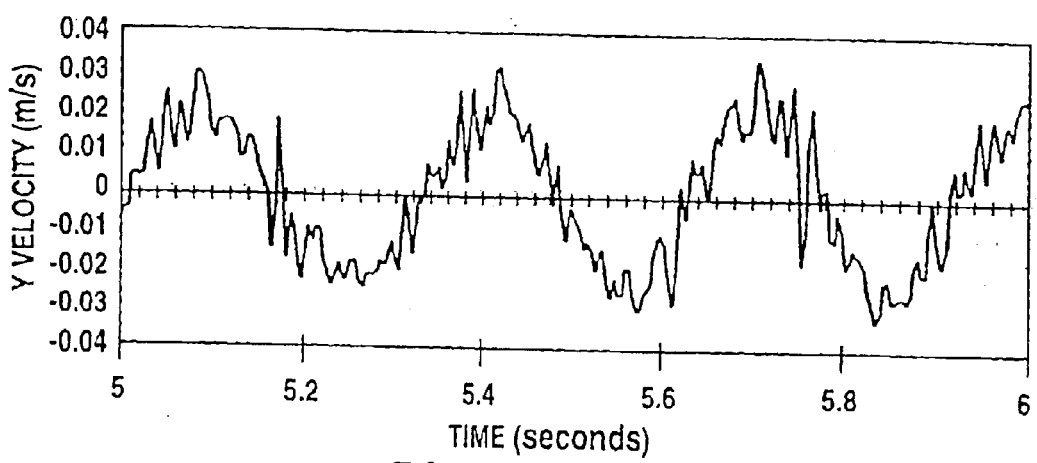
Fig. 10B5
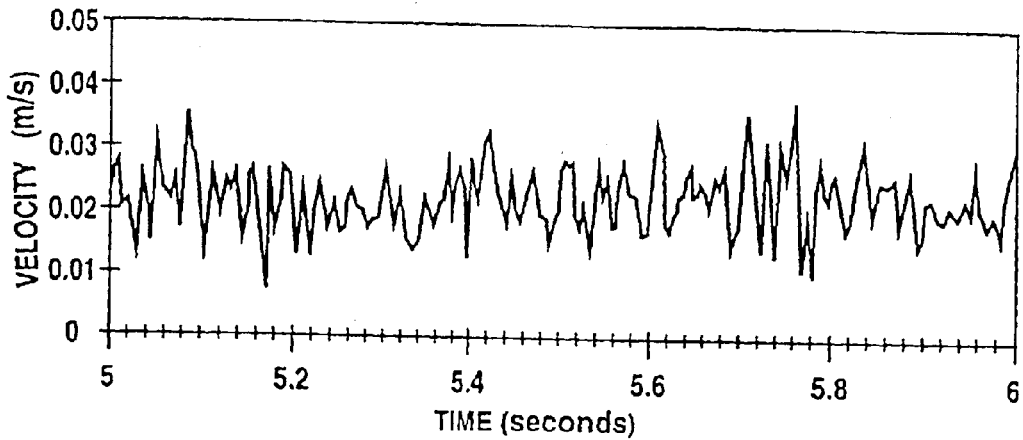
Fig. 10B6

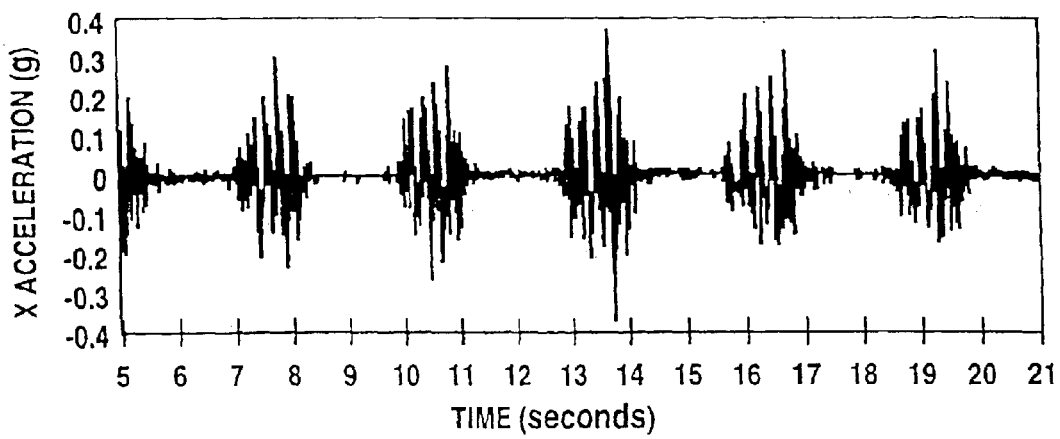
Fig. 11A1
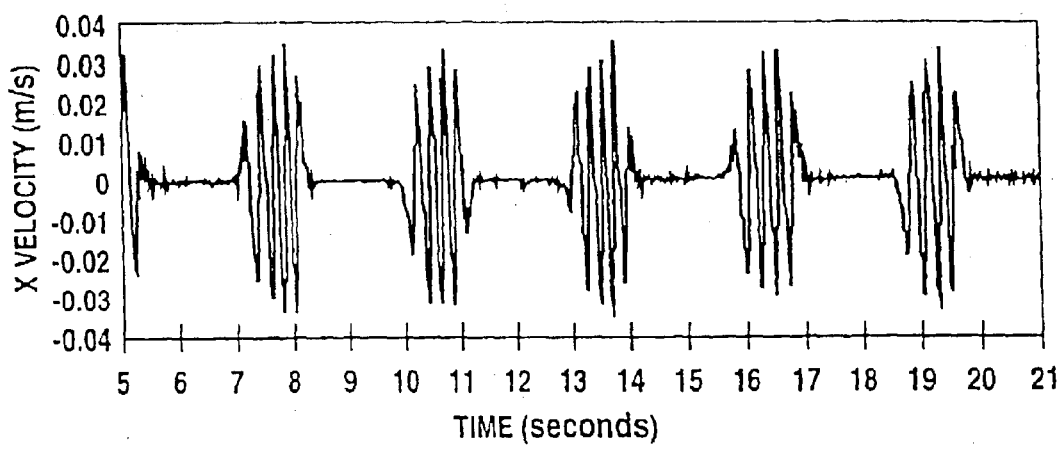
Fig. 11A2
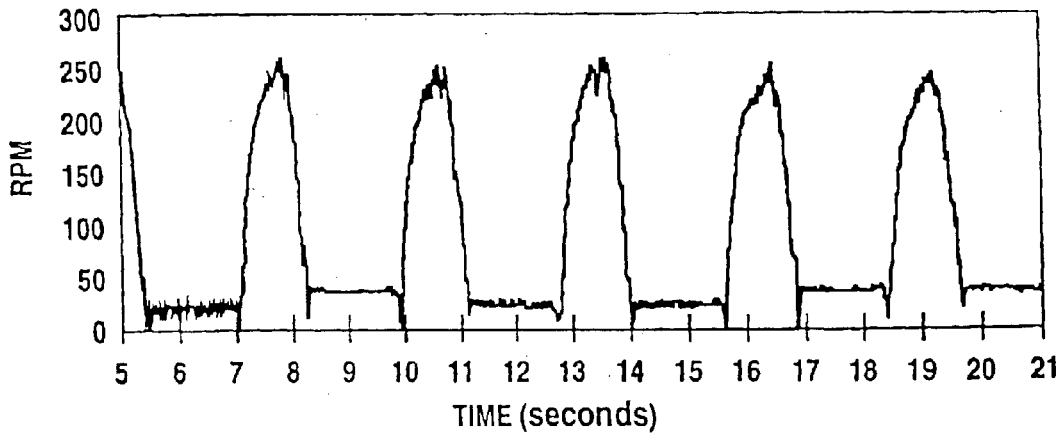
Fig. 11A3

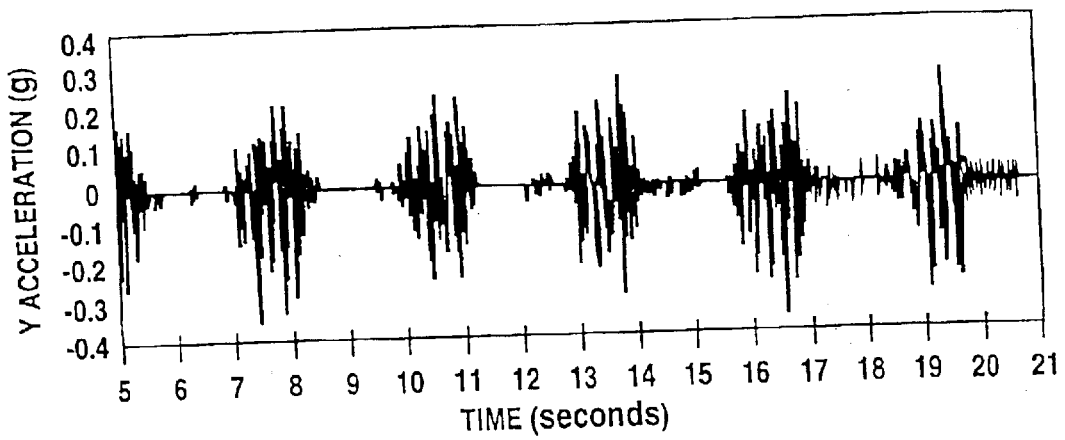
Fig. 11A4
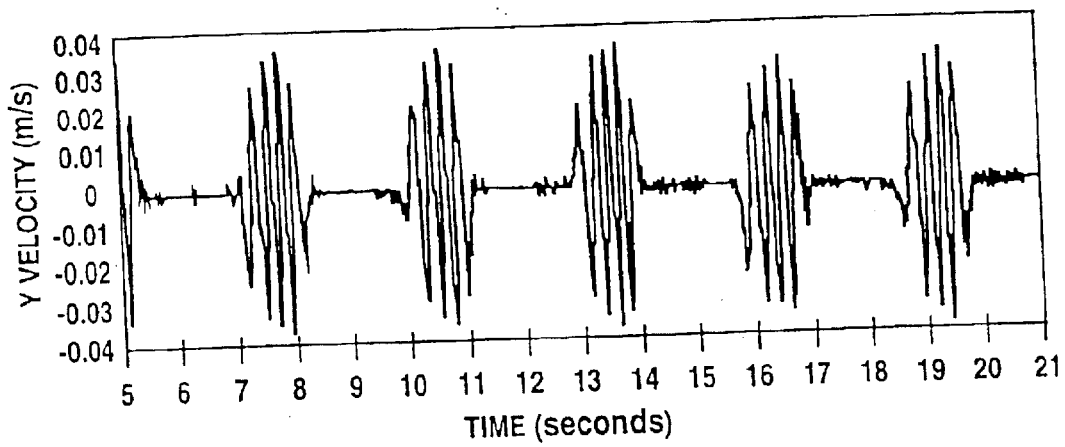
Fig. 11A5
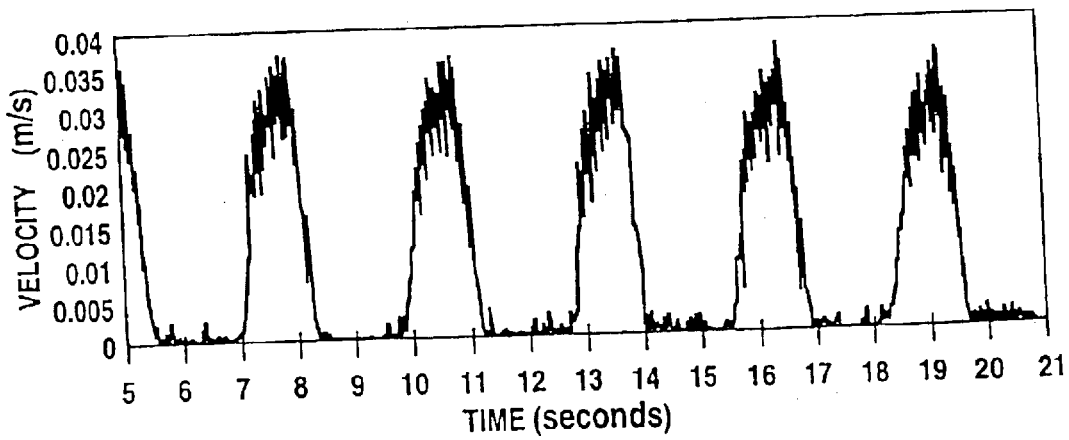
Fig. 11A6

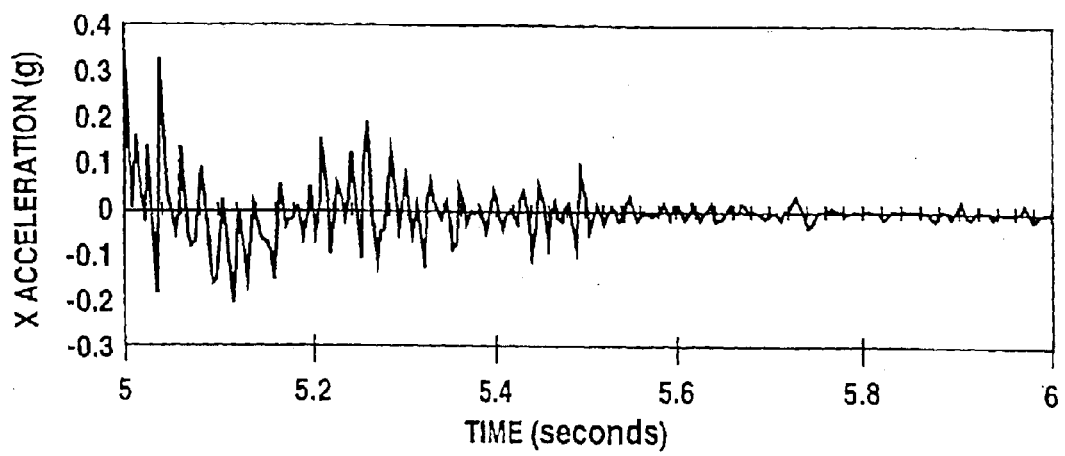
Fig. 11B1
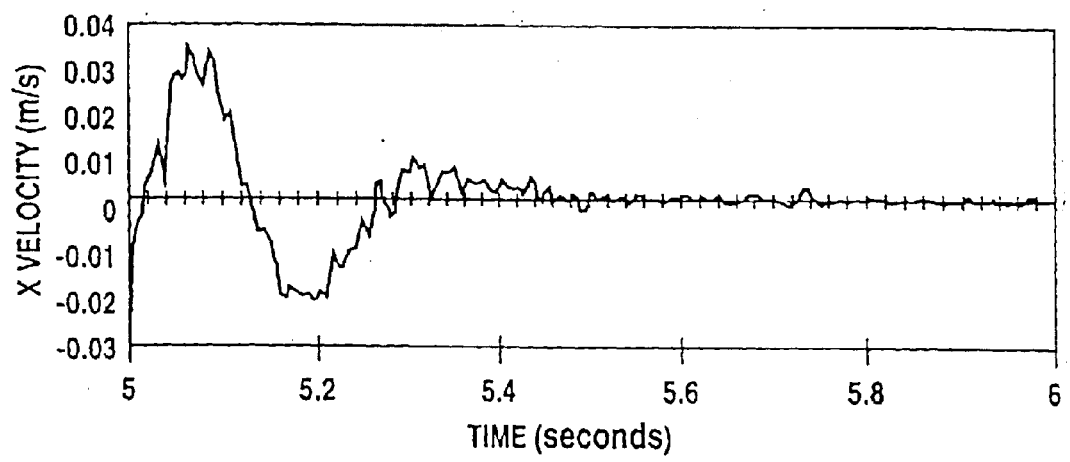
Fig. 11B2
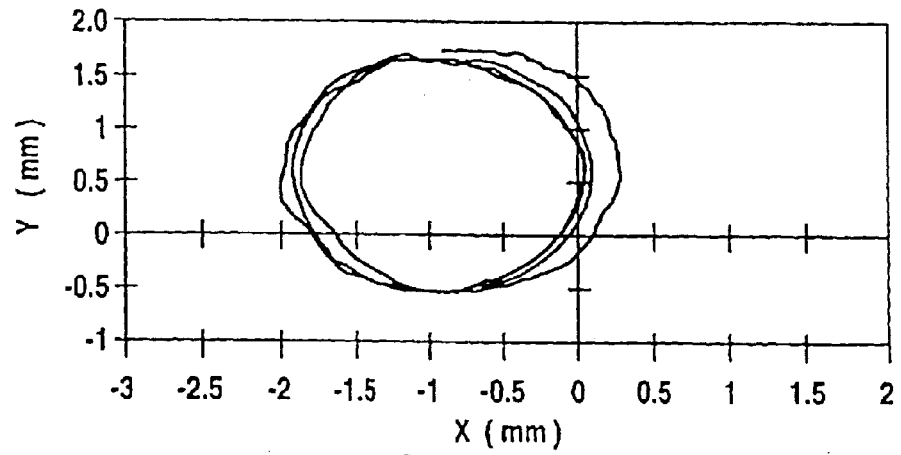
Fig. 11B3

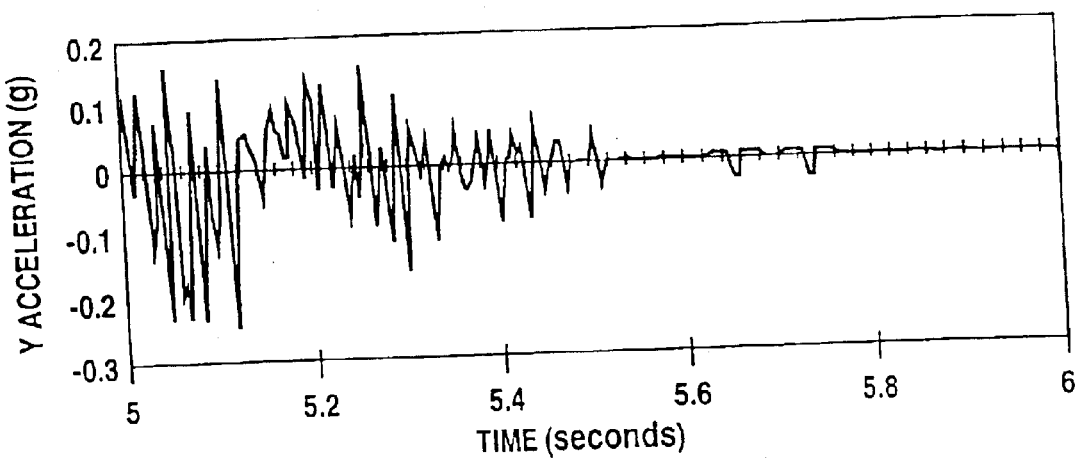
Fig. 11B4
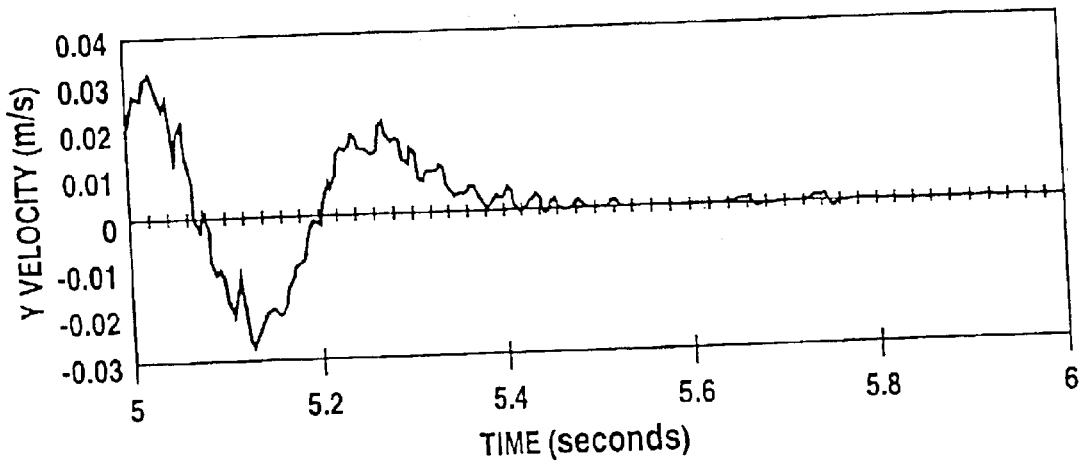
Fig. 11B5
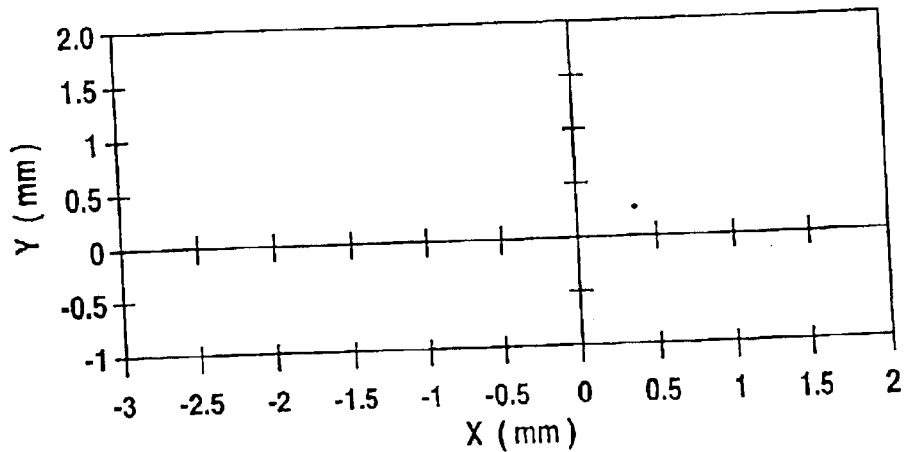
Fig. 11B6

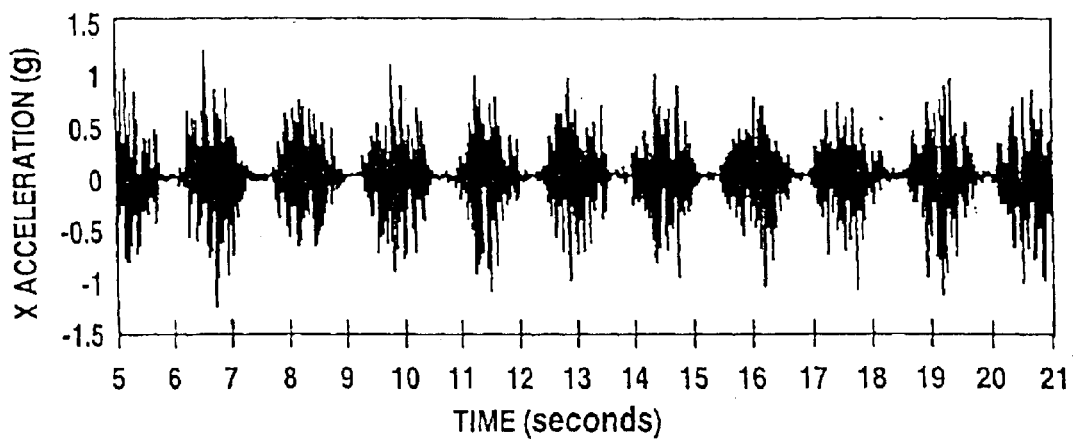
Fig. 12A1
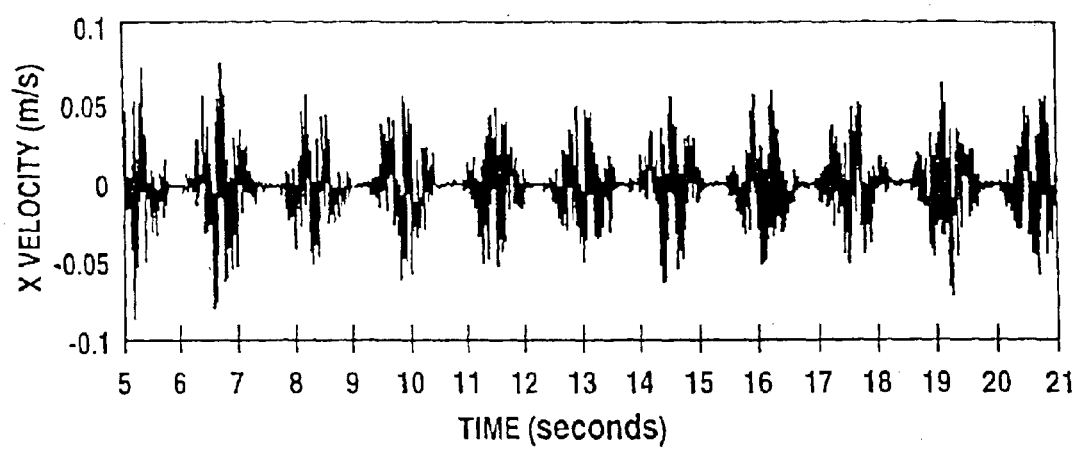
Fig. 12A2
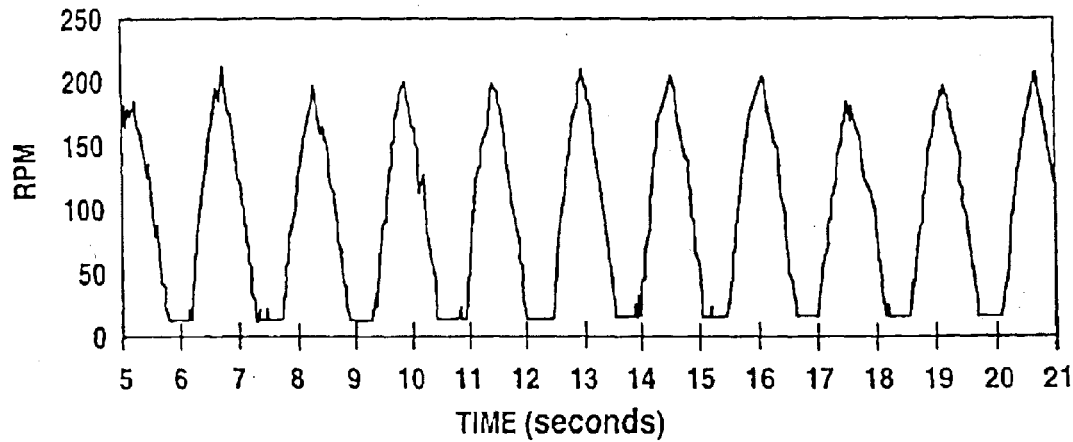
Fig. 12A3

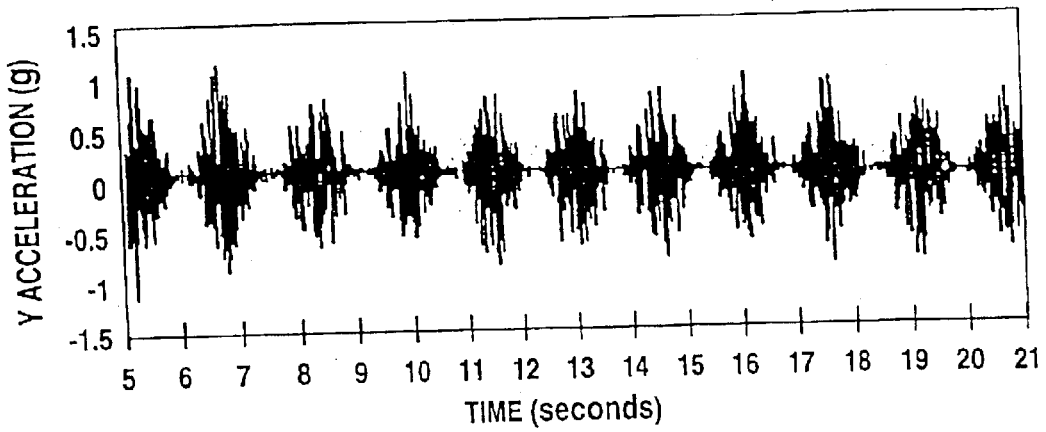
Fig. 12A4
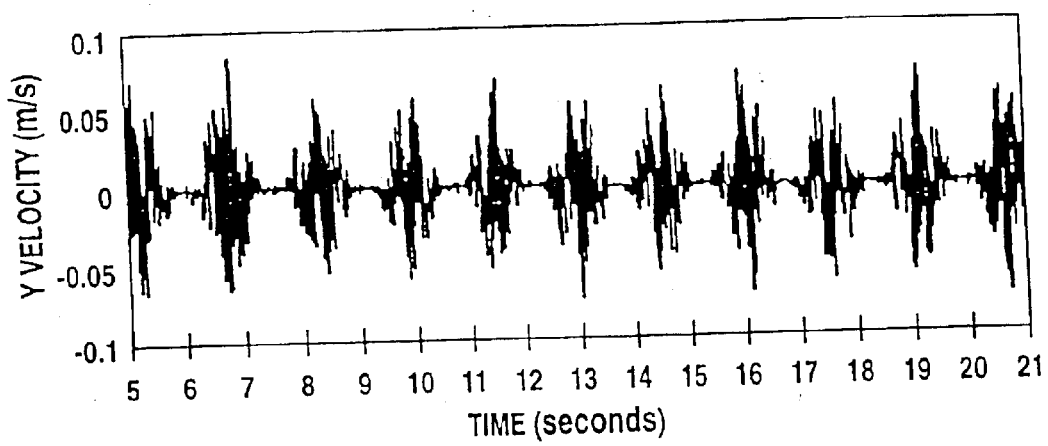
Fig. 12A5
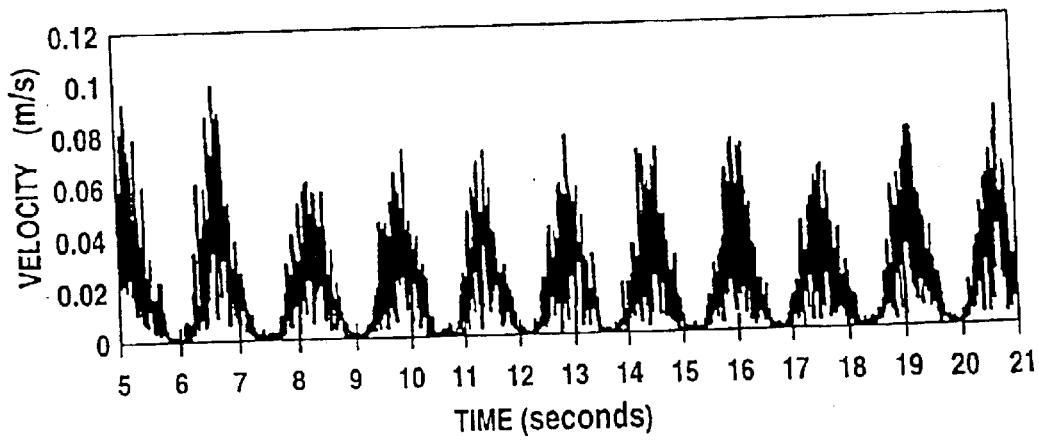
Fig. 12A6

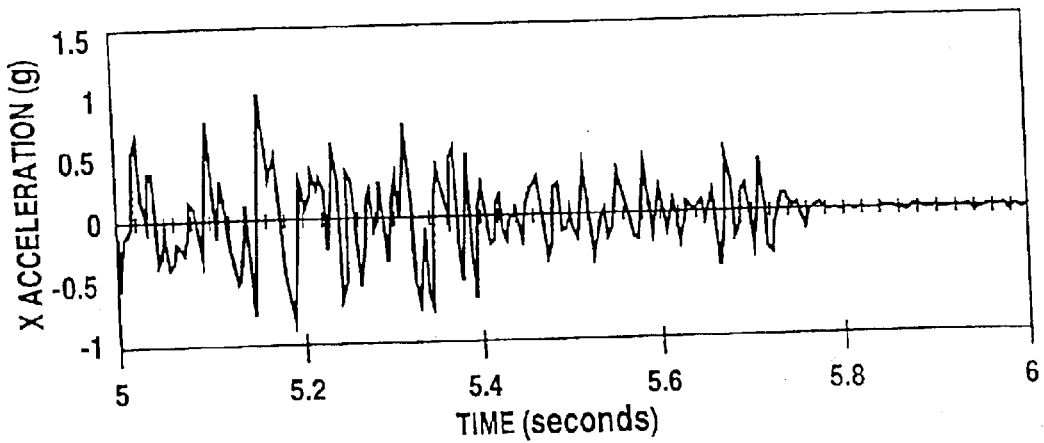
Fig. 12B1
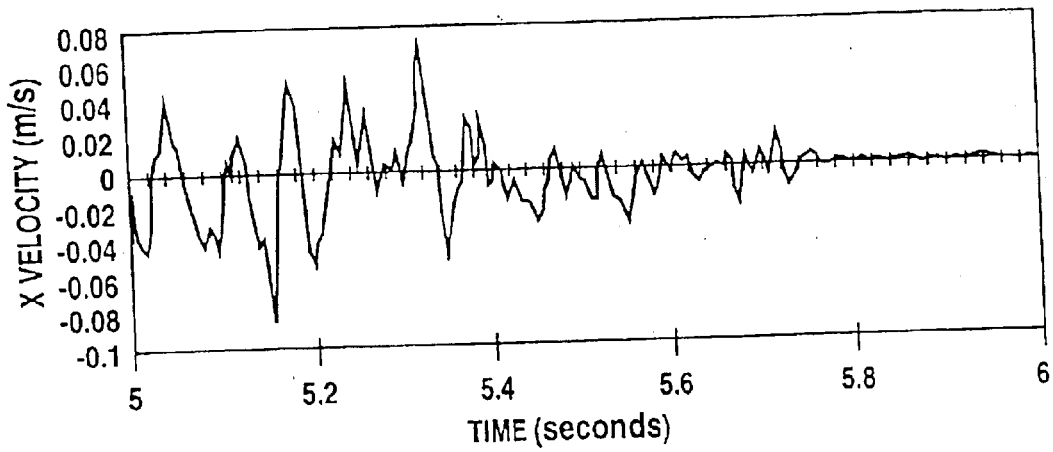
Fig. 12B2
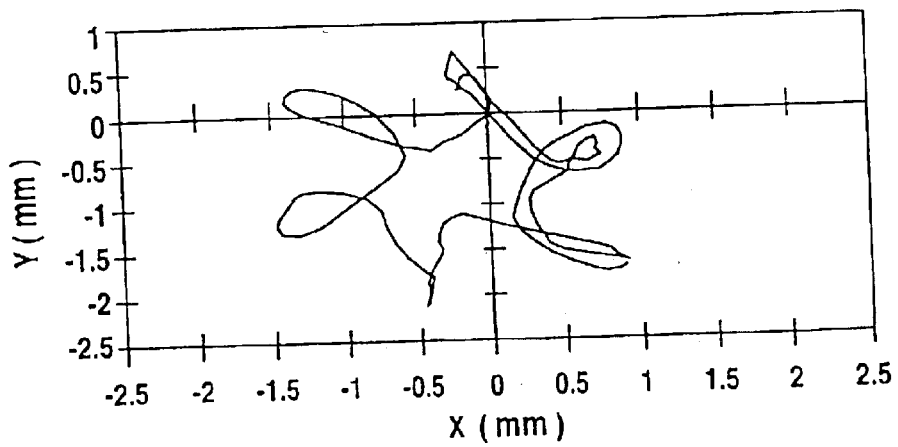
Fig. 12B3

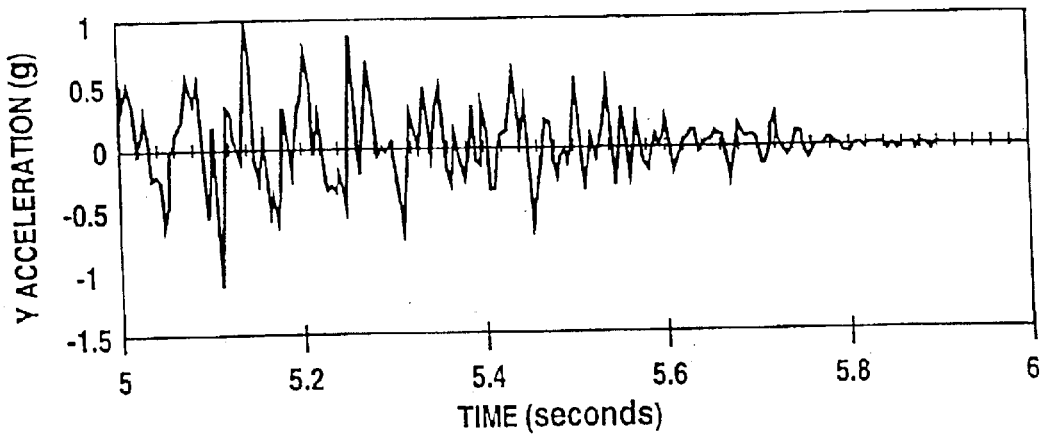
Fig. 12B4
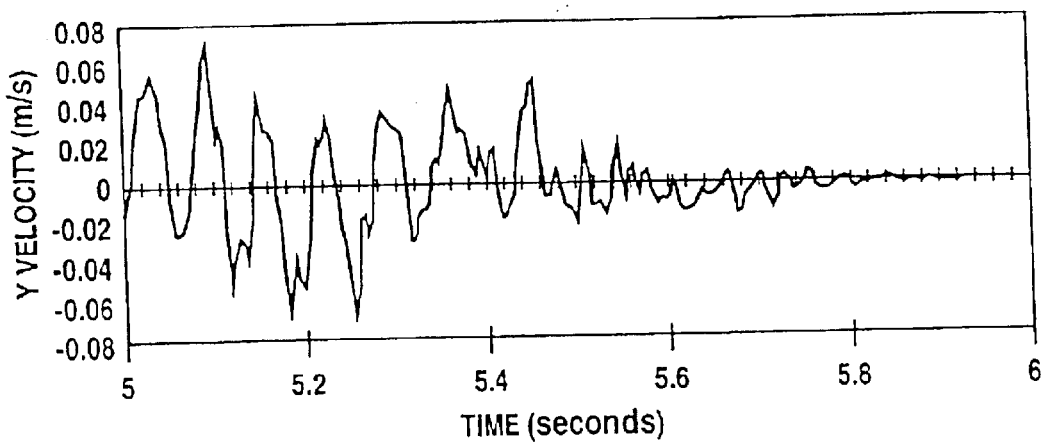
Fig. 12B5
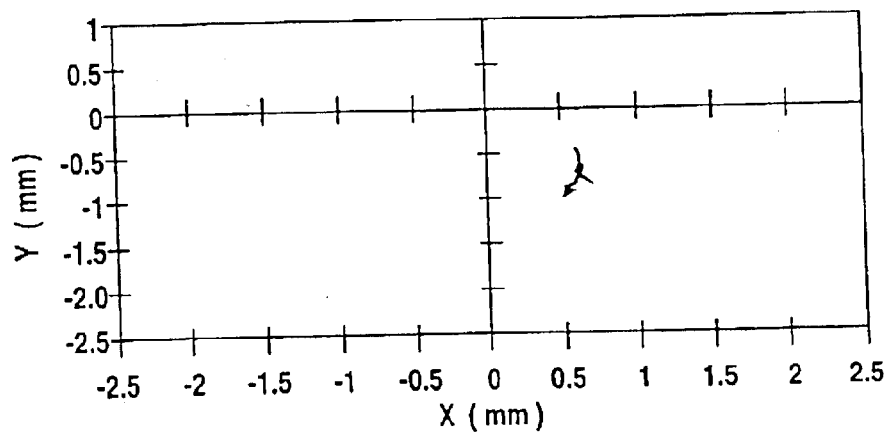
Fig. 12B6

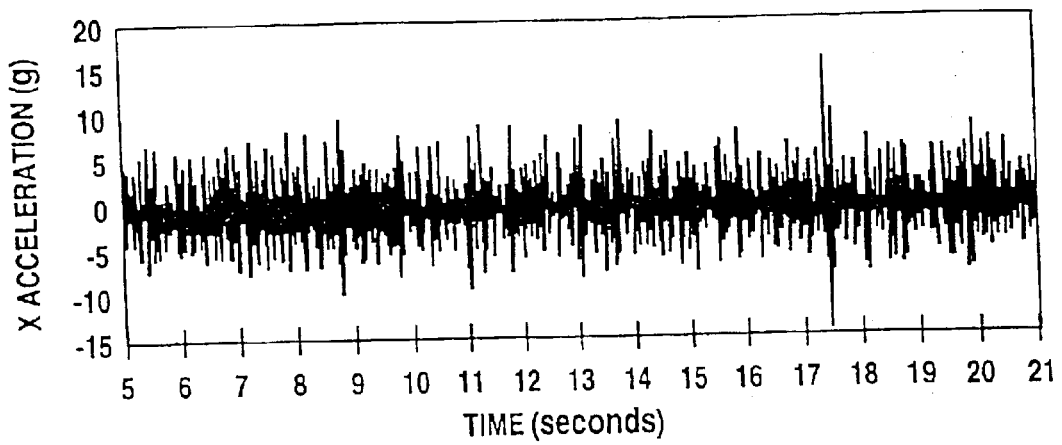
Fig. 13A1
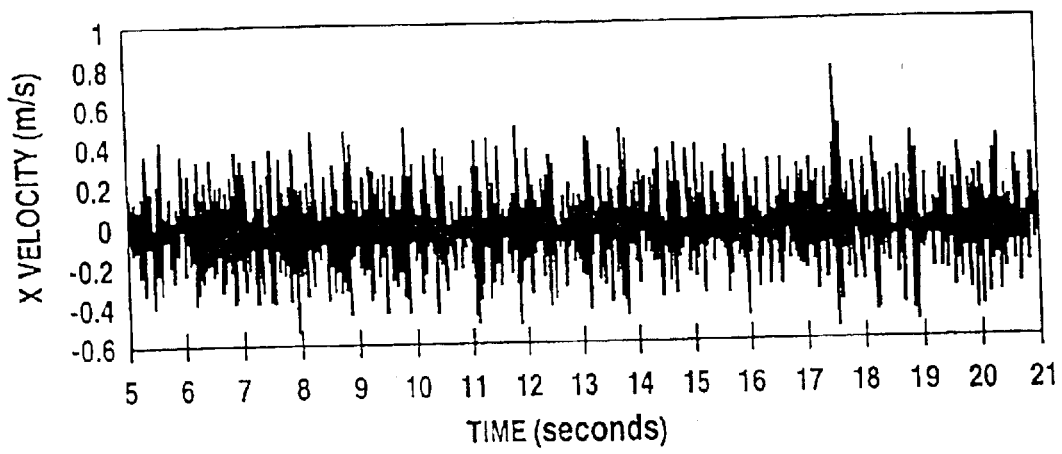
Fig. 13A2
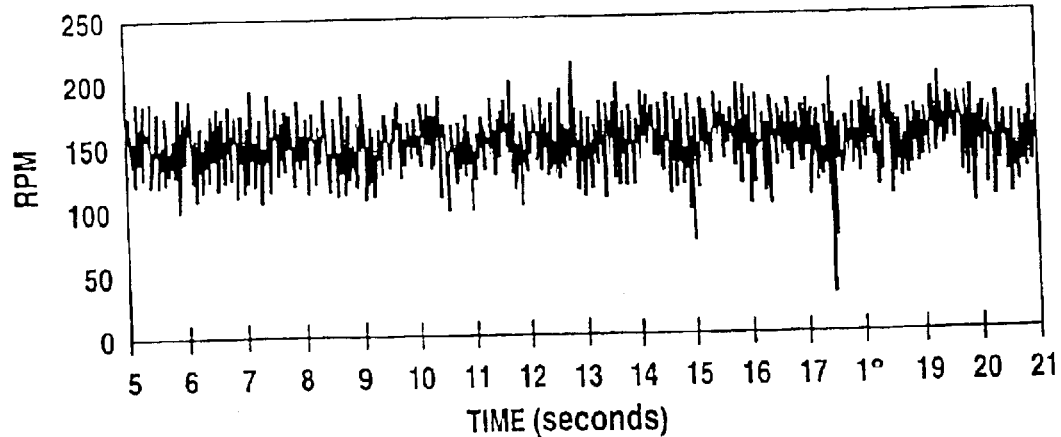
Fig. 13A3

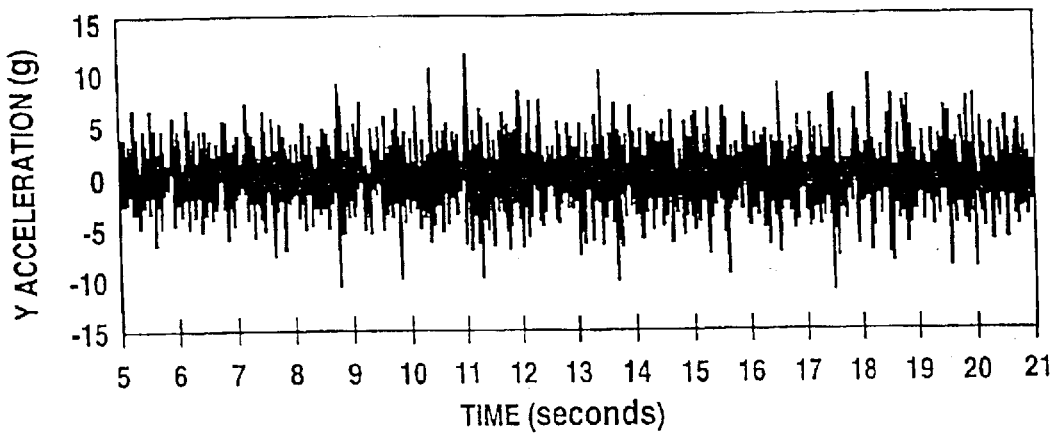
Fig. 13A4
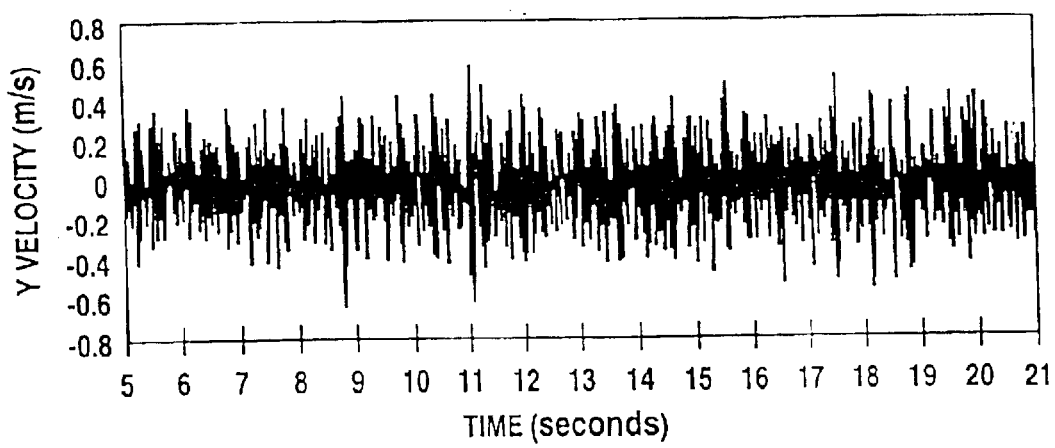
Fig. 13A5
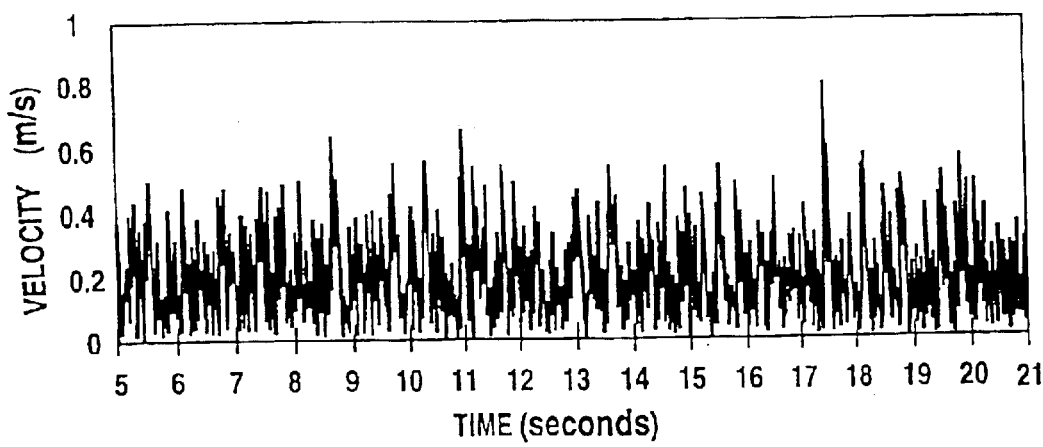
Fig. 13A6

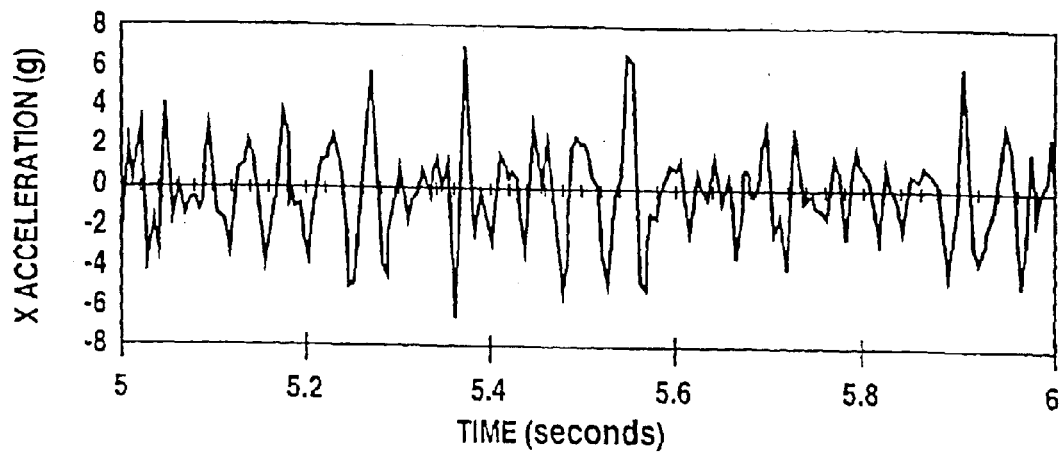
Fig. 13B1
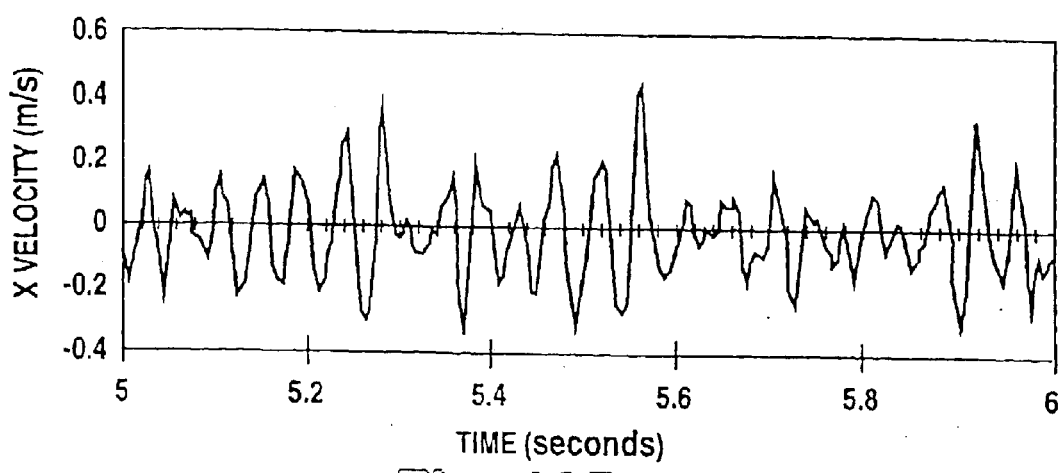
Fig. 13B2
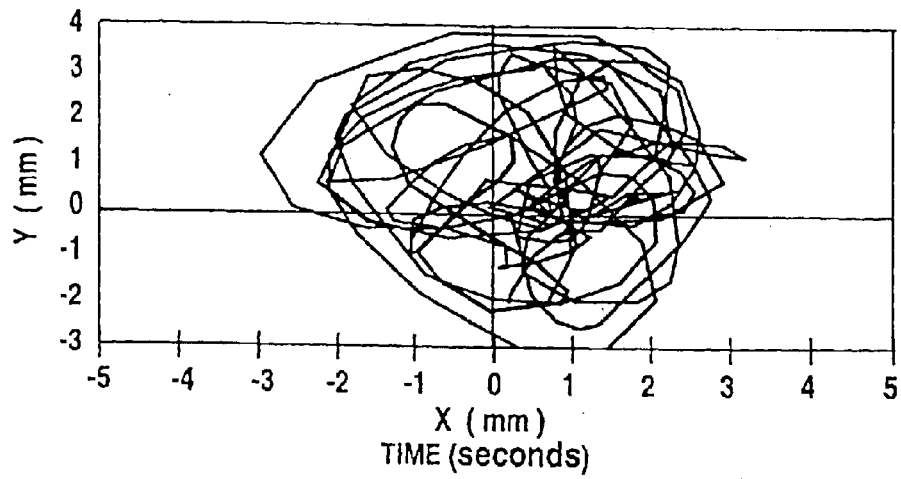
Fig. 13B3

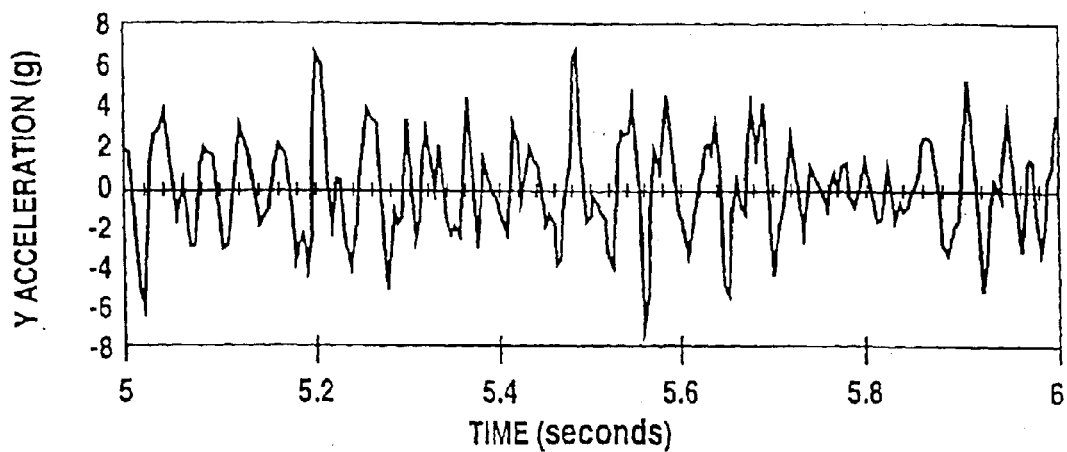
Fig. 13B4
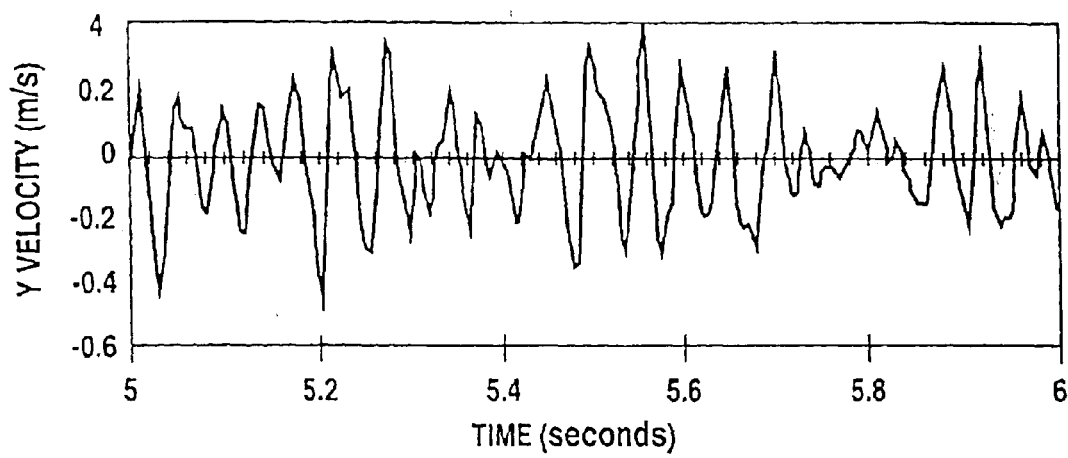
Fig. 13B5
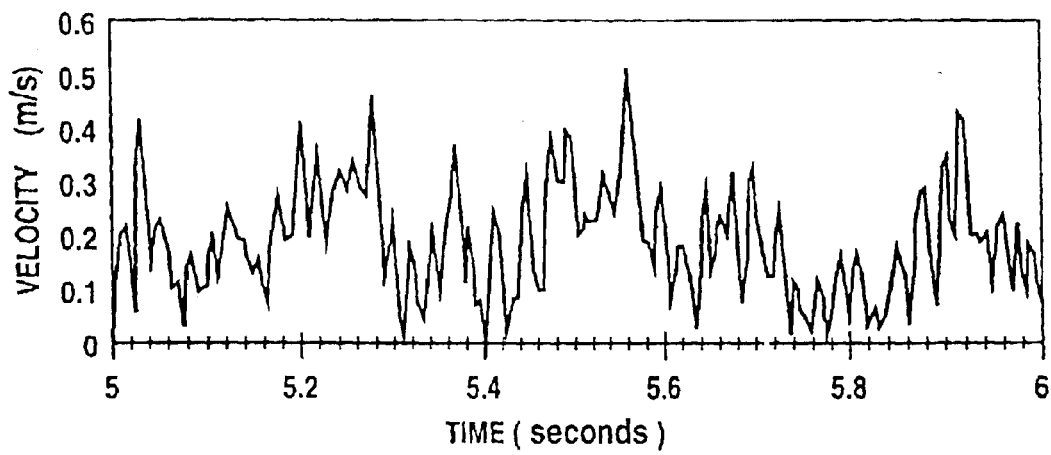
Fig. 13B6

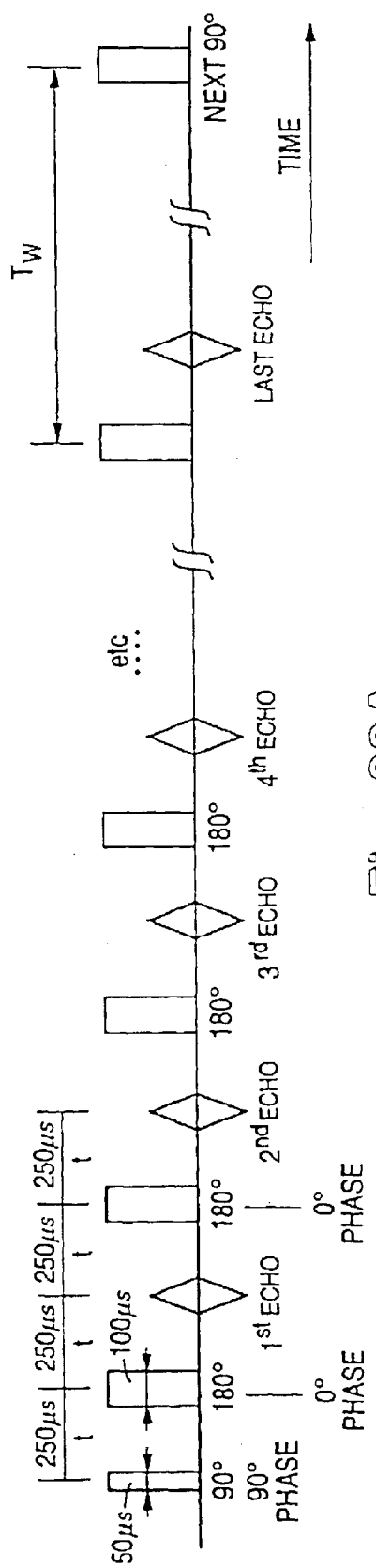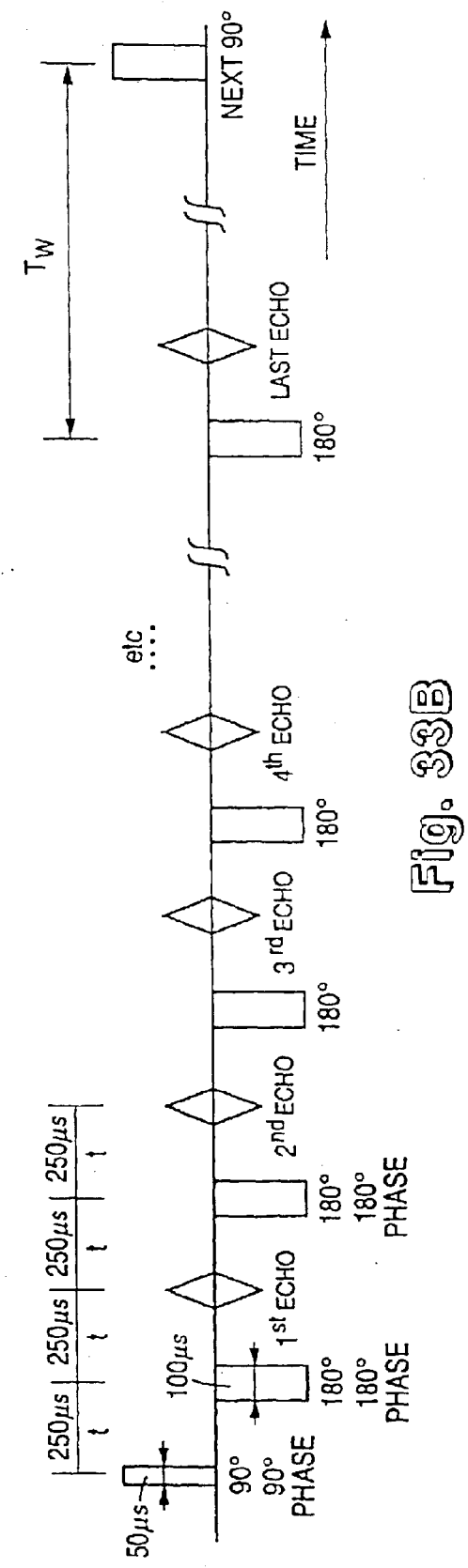

METHOD AND APPARATUS FOR NUCLEAR MAGNETIC RESONANCE MEASURING WHILE DRILLING

This application is a continuation of application Ser. No. 10/108,182 filed Mar. 27, 2002 now U.S. Pat. No. 6,583,621 which is a continuation of application Ser. No. 09/919,129, filed Jul. 31, 2001, which is a continuation of application Ser. No. 09/232,072, filed Jan. 15, 1999, now U.S. Pat. No. 6,268,726, which claims priority of provisional applications Ser. No. 60/071,612 and Ser. No. 60/071,699, both filed Jan. 16, 1998. The content of the above applications is incorporated herein by reference.

FIELD OF THE INVENTION

This invention relates generally to a method and apparatus for making pulsed nuclear magnetic resonance (NMR) measurements of earth formations while drilling a borehole. More specifically, the invention is directed to a NMR measurement-while-drilling (MWD) tool having the required mechanical strength and measurement sensitivity, and a method and apparatus for monitoring the motion of the measuring tool in order to take this motion into account when processing NMR signals from the formation surrounding the borehole.

BACKGROUND AND SUMMARY OF THE INVENTION

Various methods exist for performing downhole measurements of petrophysical parameters in geologic formations. Pulsed NMR logging is among the most important of these methods, and was developed primarily for determining parameters such as formation porosity, fluid composition, the quantity of movable fluid, permeability, and others. Importantly, NMR measurements are environmentally safe and are unaffected by variations in the matrix mineralogy.

In a typical NMR measurement, a logging tool (measurement device) is lowered into a drilled borehole to measure properties of the geologic formation near the tool. Then, the tool is extracted at a known rate while continuously taking and recording measurements. At the end of the experiment, a log is generated showing the properties of the geologic formation along the length of the borehole. This invention relates primarily to an alternative measurement, in which pulsed NMR logging can be done while the borehole is being drilled. The advantages of the latter approach in terms of saving both time and costs are apparent. Yet, very little has been done so far in terms of developing practical NMR logging-while-drilling (LWD) or measurements-while-drilling (MWD) solutions. Two of the main stumbling blocks appear to be the very stringent requirements concerning the mechanical strength of the device, as well as problems associated with inaccuracies of the received signals due to motions of the tool. The present invention addresses successfully both issues and therefore is believed to make a significant contribution over the prior art.

In order to more fully appreciate the issues discussed in detail next, a brief overview of NMR methods for measuring characteristics of formations surrounding a borehole is presented first. The interested reader is directed, for example, to the following article: Bill Kenyon et al., *Nuclear Magnetic Resonance Imaging—Technology for the 21st Century*, OIL-FIELD REV., Autumn 1995, at 19, for a more comprehensive review. The Kenyon article is incorporated herein by reference.

Basically, in the field of NMR measurements of earth formations surrounding a borehole, a downhole static magnetic field is used to align the magnetic moment of spinning hydrogen (H) protons in the formation in a first direction, the direction of the static magnetic field. In order to establish thermal equilibrium, the hydrogen protons must be exposed to the polarizing field for a multiple of the characteristic relaxation time, $T_1$. Then, the magnetic component of a radio frequency (RF) electromagnetic wave pulse, which is polarized in a second direction orthogonal to the static field, is used to tip the protons to align them in a third direction that is orthogonal to both the first and the second direction. This initial RF pulse is thus called a 90° pulse. Following the 90° pulse the protons in the formation begin to precess about the axis of the first direction. As a result, the protons produce an oscillating magnetic field. If an antenna is placed into the oscillating magnetic field, the oscillating magnetic field will produce an oscillating electric current in the antenna. Because the amplitude of the induced electrical signal is proportional to the porosity of the earth formation being measured, the signal may be calibrated to measure formation porosity. However, due to dephasing and irreversible molecular processes, the induced signal decays rapidly after the RF pulse is removed. Consequently, when the antenna is used both to transmit the RF pulses and to receive the induced NMR signal as in one embodiment of this invention, this first NMR signal may not be observable because the antenna electronics are still saturated from residual effects of the 90° RF pulse. Therefore, the NMR signal must be rebuilt as a spin echo, as discussed below, so that it may be measured.

Additionally, the behavioral characteristics of the protons after removal of the RF pulse can be used to garner information about other formation properties, such as pore size distribution and permeability. Immediately after the 90° RF pulse is turned off, the protons precess in phase. However, due to inhomogeneities in the static magnetic field and irreversible molecular processes, the protons begin to dephase, which causes the induced signal to decay. Nevertheless, the dephasing due to inhomogeneities in the static magnetic field is partially reversible. Therefore, by applying a 180° RF pulse, the instantaneous phases are reversed such that the protons gradually come back into phase, thus rebuilding the induced signal. The antenna can detect this signal because the time required for rebuilding the signal is long enough to allow the antenna electronics to recover from the 180° RF pulse. After the signal peaks at the time when the protons are back in phase, the signal will then begin to decay due to dephasing in the opposite direction. Thus, another 180° RF pulse is needed to again reverse the instantaneous phases and thereby rebuild the signal. By repeating a series of 180° RF pulses, the signal is periodically rebuilt after each dephasing, although each rebuilding is to a slightly lesser peak amplitude due to the irreversible molecular processes. Eventually, the irreversible processes prevail such that no further rephasing is possible and the signal dies out completely. Each rebuilding of the signal in this manner is called a spin echo, and the time constant associated with the decay of the spin echo amplitudes is called the transverse relaxation time, $T_2$.

Because experiments have shown that $T_2$ is proportional to the pore size of the formation, calibration and decomposition of $T_2$ yields a measure of the formation's pore size distribution. Moreover, when combined with the porosity measurement, $T_2$ yields an estimate of the formation's permeability. As noted above, the NMR signal may also be calibrated to obtain other formation characteristics, such as free fluid volume, bound fluid volume, fluid identification, and diffusion coefficients. Because the drilling mode of operation using a preferred embodiment of this invention may allow for enough time to develop only one spin echo, or at most a few spin echoes, the apparatus may achieve only porosity and limited $T_2$ measurements while drilling. However, the other types of NMR measurements discussed above are possible in nondrilling modes of operation, such as stationary tool, sliding or wiping tool.

From the preceding discussion it should be apparent that in order to enable accurate NMR measurements it is important that the same protons be tipped and rephased for each successive spin echo. Excessive movement of the tool in the borehole during NMR measurement can destroy the accuracy of the measurement by changing the location of the measurement volume, i.e., which protons in the formation are affected by the interaction of the static and RF pulse magnetic fields. Therefore, if the motion of the tool during NMR measurement is not known, which generally is the case in a logging while drilling environment, the NMR measurement may not be reliable.

The present inventors know of three issued patents directed to practical NMR measurements while drilling: U.S. Pat. No. 5,705,927 issued Jan. 6, 1998, to Sezginer et al.; U.S. Pat. No. 5,557,201 issued, Sep. 17, 1996, to Kleinberg et al.; and U.S. Pat. No. 5,280,243 issued Jan. 18, 1994, to Miller. Of these references, the '201 patent more specifically shows how to improve the tool's susceptibility to lateral tool motion by increasing the radial dimension of the measurement volume. However, the axial length of the sensitive zone (i.e., the measurement volume) of the '201 patent is on the order of two to four inches, whereas that of the present invention is on the order of two feet. Thus, the susceptibility of the present invention to axial tool movement is greatly improved over the prior art. Indeed, for typical drilling rates, axial movement of the present NMR tool has a negligible impact on the quality of the NMR measurement. Importantly, none of the three patents recited above discloses any means to monitor the tool motion to assure a drilling operator that the NMR measurements are accurate.

One method of dealing with the motion of the NMR tool in accordance with the present invention is to monitor the tool motion during NMR measurement and discard the measurement if the tool motion is above maximum acceptable limits. For example, in a preferred embodiment of this invention, testing has shown that the lateral velocity of the tool must be less than or equal to about 0.2 m/s to preserve the integrity of the NMR measurement. Accordingly, an important aspect of the present invention is the disclosure of a method for monitoring the tool motion by using two pairs of accelerometers located at the ends of two coplanar, orthogonal drill collar diameters. The accelerometers are used to measure the lateral acceleration of the tool, and the acceleration is integrated once to obtain the velocity and twice to obtain the displacement.

Although U.S. Pat. No. 4,958,125, issued Sep. 18, 1990, to Jardine et al., discloses a similar method and apparatus for determining characteristics of the movement of a rotating drill string, the method for determining lateral acceleration in the '125 patent is directed to a vertical drill string orientation. Referring to FIG. 8, four accelerometers oriented such that ac1 and ac2 are on one axis and ac3 and ac4 are on an orthogonal axis, both orthogonal to the general axis of rotation, the '125 patent sets forth the following equations of motion:

$$ac1 = ac + ax \cos d$$

$$ac2 = ac - ax \cos d$$

$$ac3 = ac + ax \sin d$$

$$ac4 = ac - ax \sin d \qquad \text{Eqs. [1]}$$

where ac is the centripetal acceleration, ax is the lateral acceleration, and d is the angle between the ac1/ac2 axis and the lateral acceleration vector. From Eqs. [1], the '125 patent derives the following expressions for the rotation speed, S, and lateral acceleration, ax:

$$S = [60/2\pi]^*[(ac1+ac2)/(2r)]^{1/2} \qquad \text{Eq. [2]}$$

$$ax = \{[(ac1-ac2)/(2)]^2 + [(ac3-ac4)/(2)]^2\}^{1/2} \qquad \text{Eq. [3]}$$

The direction of the lateral acceleration is determined by the following expression:

$$\tan d = (ac3-ac4)/(ac1-ac2) \qquad \text{Eq. [4]}$$

However, Eqs. [1] do not contain any gravitational acceleration terms. Thus, Eqs. [1] correctly describe the tool motion only if the tool is oriented vertically such that the lateral component of the gravitational acceleration is zero.

To describe the tool motion accurately if the tool is in some general, inclined orientation, the equations of motion must include the gravitational acceleration terms as follows:

$$ac1 = ac + ax \cos d + g \sin \alpha \cos e$$

$$ac2 = ac - ax \cos d - g \sin \alpha \cos e$$

$$ac3 = ac + ax \sin d - g \sin \alpha \sin e$$

$$ac4 = ac - ax \sin d + g \sin \alpha \sin e \qquad \text{Eqs. [5]}$$

where g is the earth's gravitational constant (9.81 m/s$^2$), $\alpha$ is the inclination angle of the tool axis with respect to the vertical (as shown in FIG. 7), and e is the angle between the a1/a2 axis and the g sin $\alpha$ direction (as shown in FIG. 8). As noted in the '125 patent, Eq. [2] still holds true for a general orientation because of fortuitous plus and minus signs on the gravitational acceleration terms. However, neither Eq. [3] nor Eq. [4] holds true for a general orientation. Thus, for a general orientation, another method is needed to determine the magnitude and direction of the lateral acceleration, ax.

In a specific embodiment, the present invention solves this complication caused by the presence of the gravitational acceleration terms in a general, inclined drill string orientation by incorporating a high-pass filter to eliminate those terms. This solution is possible because the rotational frequencies of typical drilling speeds are well below the frequencies of the lateral accelerations of interest. Thus, the gravitational acceleration terms, which vary periodically at the frequency of the drill string rotation speed, can be safely eliminated without corrupting the lateral acceleration signals. After filtering in this manner, the governing equations of motion revert back to Eqs. [1], and Eqs. [3] and [4] may be used to determine the magnitude and direction of the lateral acceleration. Then, the lateral velocity and lateral displacement may be obtained by integrating the lateral acceleration once and twice, respectively. By comparing the measured motion to the allowable motion criterion, it is possible to modify the NMR measurement to optimally suit a given drilling environment.

Based on information from the motion sensors and based on parameters set by the operator before the tool was deployed, in accordance with the present invention the tool enters one of the following operating modes:

(a) Shutdown. This mode is selected anytime the tool detects the presence of metallic casing and/or is on the surface, or detects motion phenomena that make NMR measurements impossible.

(b) Wireline emulation. When no motion is detected, the tool attempts to emulate NMR measurements as typically done by wireline NMR tools.

(c) Normal drilling. During normal drilling conditions, moderate lateral motion is present, which allows for abbreviated NMR measurements.

(d) Whirling. During whirling, lateral motion is violent, but short time windows exist during which the lateral velocity drops to a point, where a porosity-only measurement is possible. The tool identifies these windows and synchronizes the NMR measurement appropriately.

(e) Stick-slip. In this drilling mode, windows exist in which short NMR measurements are possible, interspersed with periods of very high lateral/rotational motion. Again, the tool identifies these windows and synchronizes the NMR measurement appropriately.

The motion management aspect of this invention provides an algorithm to predict desirable time windows in which to make valid NMR measurements. As seen in FIG. 9, experiments have identified three distinct types of tool motion: (1) normal drilling; (2) whirling; and (3) stick-slip. These three types of motion are identifiable based on the time histories of the rotation speed, lateral velocity, and lateral displacement of the tool. In normal drilling motion, the lateral velocity of the tool is typically within acceptable limits so that valid NMR measurements may be made at almost any time. Sample plots of typical tool motion during normal drilling are shown in FIGS. 10A(1)-(6) and 10B(1)-(6). In whirling motion, the lateral velocities are usually outside acceptable limits, which makes valid NMR measurements difficult to obtain. However, as shown in FIG. 9, by monitoring the velocity, acceleration, and time duration in which the velocity remains within certain prescribed limits, it is possible to predict acceptable NMR measurement periods during whirling. Sample plots of typical tool motion during whirling are shown in FIGS. 13A(1)-(6) and 13B(1)-(6). In stick-slip motion, the drill bit periodically sticks to the borehole wall and then slips away, causing the drill string to periodically torque up and then spin free. Sample plots of typical tool motion during stick-slip are shown in FIGS. 11A(1)-(6); 11B(1)-(6); 12A(1)-(6) and 12B(1)-(6). During the stick phase, the tool is virtually stationary thus providing a good time window in which to make NMR measurements. In contrast, the lateral velocity during the slip phase may be outside acceptable limits, depending on such variables as bit type, formation strength, and stiffness and length of the drill string. By analyzing the time histories in this manner, acceptable time windows may be predicted in which to make valid NMR measurements.

The motion identification aspect of this invention also provides another benefit with regard to drilling tool damage reduction and service life enhancement. Because whirling and stick-slip motion can be damaging to drilling tools, this invention's capability of identifying these types of motion is very useful to a drilling operator. Specifically, if the operator knows that the drill collar is undergoing whirling or stick-slip motion, the operator can make appropriate changes to the weight-on-bit and rotation speed parameters and thereby change the motion to approach normal drilling as much as possible. As a result, tool damage is reduced and service life is enhanced.

Alternatively, this invention also incorporates a method for measurement of the tool motion by means of acoustic sensors. In this alternative, at least two acoustic sensors are placed on the perimeter of the drill collar. If only two acoustic sensors are used, they are preferably placed on orthogonal diameters (i.e., spaced 90° apart). These acoustic sensors detect the distance from the tool to the borehole wall and thus directly measure the lateral displacement of the tool in the borehole. Because the sampling rate of the acoustic sensors is much greater than typical drill string rotation speeds, the rotation is negligible with respect to the displacement calculation. In turn, the displacement may be differentiated once to obtain the velocity and twice to obtain the acceleration. Again, by comparing the measured tool motion to the allowable motion criterion, the corresponding NMR measurement may be appropriately retained or discarded. This quality control check may be accomplished using either displacement or velocity data, because the displacement criterion is over a known time span (i.e., the time between the 90° pulse and the signal acquisition window). Alternatively, when combined with an inclinometer or magnetometer measurement from which the drill collar rotation speed may be obtained (as described in U.S. Pat. No. 4,665,511 issued May 12, 1987, to Rodney and Birchak), the time histories of the motion may be used in conjunction with the prediction algorithm discussed above to predict acceptable NMR measurement windows. The same approach could also be used with contact sensors (as described in U.S. Pat. No. 5,501,285 issued Mar. 26, 1996, to Lamine and Langeveld) instead of acoustic sensors to measure the tool displacement by measuring the change in resistance through the drilling mud.

Another alternative for the motion management aspect of this invention is to correct the NMR measurement for losses in the NMR signal due to lateral motion during measurement. That is, by measuring the lateral displacement of the tool during NMR measurement as described above, the change in the sensitive volume can be calculated, which in turn allows the calculation of an appropriate correction factor to be applied to the received NMR signal to compensate for tool movement. This correction may be accomplished by using displacement information derived from any of the three sensor types discussed above (accelerometers, acoustic sensors, or contact sensors). An advantageous embodiment of the acoustic sensor form of this invention meets a tool position error specification of about 5%, which allows correction of the NMR signal to within about 95% of the signal for a stationary tool. Therefore, rather than discard an NMR measurement taken during a period of what would otherwise be excessive lateral motion, the NMR signal can be corrected to compensate for the tool motion.

Another aspect of the motion-detection problem of this invention is the operation of phase-alternated signal averaging, which is typical for NMR data acquisition and which is further described below. The salient feature of phase alternation is the coherent accumulation of NMR data, coupled with the progressive suppression of non-NMR artifacts. A large contribution to the latter comes from magneto-acoustic oscillations ("ringing") within the ferrous material as well as pulse-induced vibrations in current-carrying conductors (also customarily termed "ringing"). The pair-wise subtraction process relies on the fact that these artifacts are more or less repeatable, given the same excitation through a series of 180° RF pulses. It has been determined by experimentation that the patterns of these artifacts tend to change cyclically with the tool's orientation and bending.

This invention provides for a means to accommodate ringing pattern changes and the effects of partial de-coupling of the magnet and antenna by taking advantage of the fact that the generally cyclical and repetitive nature of the drilling process is the source of the dynamic geometry changes. Practically all drilling involves rotation of a drill bit. Rotation is provided by bulk rotation of the entire drill string, use of a mud motor, or by a combination of both. As an example, the bit center orbit plots 10B3, 11B3, 12B3 and 13B3 show that the position of the bit is very repetitive and essentially duplicated with each revolution for drilling modes other than whirling. By measuring one of the many manifestations of this rotation, including oscillations of the on-rotating section, the NMR measurement can be repeatedly synchronized to a particular and repeatable geometry.

Magnetic and gravity tool face angles are among the most available means for tracking tool orientation on a rotating or oscillating drill string. Bending stress, position derived from integration of acceleration data, sonic sensors or contact sensors are other examples of sensors suitable for synchronization of the NMR measurement.

In an important aspect, this invention also provides a permanent magnet, preferably having tubular construction, which produces a static magnetic field that is oriented in a substantially orthogonal direction of both the axis of the borehole and the drilling device, and that diminishes in magnitude by about the square of the distance from the magnet. Over the relatively thin sensitive volume (1.5 mm thickness) the radial field gradient is essentially constant.

As shown in FIG. 6B, the magnetic field is that of a linear dipole with a field direction that depends on the azimuthal direction of the tool. Although some prior NMR tools have used magnets having a linear dipole magnetic field (such as that disclosed in U.S. Pat. No. 4,710,713), those tools did not comprise a tubular magnet through which drilling mud may be pumped nor are these magnets meant to be rotated. Additionally, although the Kleinberg et al. '201 patent discussed above comprises tubular magnets, the magnetic field produced is not a linear dipole. The tubular construction used in accordance with the present invention provides a central cavity through which drilling mud may be pumped to enable NMR measurement while drilling. Also, the magnetic field produced by the magnet has an essentially constant gradient within the measurement volume which, when combined with an RF pulse that is tuned to the proper frequency, produces a more uniform annular sensitive region (measurement volume) that is completely within the earth formation.

Another aspect of the present invention is the use of a magnet that is comprised of multiple segments. Thus, in accordance with the present invention it is possible to tailor the resultant field by tuning the contributions from the individual segments. Such tuning may be accomplished by (a) selective demagnetization, which is possible for the SmCo5 variant of samarium-cobalt material, by (b) adjusting the volume for each segment, or (c) by adjusting the polarization direction of each individual segment. Such freedom in field shaping is advantageous if it is necessary, as in the present invention, to pre-compensate the magnetic field in order to accommodate the effects of soft-magnetic material in the vicinity of the magnet.

It may not be obvious even to a person skilled in the art that the magnetic field from a linear dipole is suitable for measurements while drilling, where the magnet is rotated with respect to the formation at rates up to about 300 RPM. Any given point within the sensitive volume 36 in FIG. 6B experiences a magnetic field of approximately constant magnitude, but that rotates synchronously with the drill collar. It may appear that for hydrogen nuclei with longitudinal relaxation times $T_1$ of several seconds, these spins would not align themselves properly with a rotating field that completes a rotation in much less time than it takes for polarization. However, the relaxation time $T_1$ only governs the build-up of the magnitude of the nuclear polarization. A change in direction can be followed much faster and depends on the resonant Larmor frequency of the nucleus. At a typical field strength of 117 gauss, the resonance frequency is 500 kHz. The condition for Adiabatic Fast Passage (AFP), under which the nuclear polarization follows a change in direction of the polarizing field virtually instantaneously, is that the rate of change must be much less than the period of the Larmor frequency. Comparing 500 kHz with a maximum rotational frequency of 5/sec, we find a ratio of 100,000:1, which satisfies the requirement for an AFP condition by a wide margin. Consequently, although using a rotating drill collar which causes all fields within the formation to constantly change direction, the hydrogen nuclei always follow the changing directions without noticeable delay.

As is known in the art of NMR measurement, the frequency of the RF pulse must be tuned to the Lamior frequency ($f_L$) (in Hertz) of the hydrogen protons, which is given by the following equation:

$$f_L = 4258 B_0 \qquad \text{Eq. [6]}$$

where $B_0$ is the magnitude of the static magnetic field (in Gauss). Because the static magnetic field of this invention decreases monotonically as a function of radial distance from the tool, the location of the sensitive zone may be selected by choosing a value of $B^0$ that coincides with the desired radial distance from the tool. In this manner, the sensitive zone can be fixed entirely within the earth formation to be measured, instead of partially in the borehole. As described in U.S. Pat. No. 4,350,955, issued Sep. 21, 1982, to Jackson and Cooper, if the sensitive zone is partially in the borehole, that situation presents a serious drawback to the system in that the NMR signal from the borehole fluid overwhelms the signal from the earth formation.

Prior art systems have attempted to solve this problem by doping the borehole fluid with chemicals (as described in the '955 patent), which was time consuming and expensive, or by utilizing a gradient coil to produce an additional pulsed magnetic field to cancel the borehole signal (as described in the '201 patent), which further complicated the system. Therefore, the capability of the present invention to fix the sensitive zone completely within the earth formation without any additional apparatus constitutes a valuable improvement over most of the prior art. Moreover, the static magnetic field of this invention as a function of radial distance from the tool is such that the location of the Larmor frequency for the sodium (Na) quadruple moment lies inside the tool volume, as shown in FIG. 23. The gyromagnetic ratio of sodium is 1127 Hertz/gauss. To resonate at the same Larmor frequency, sodium requires approximately four times the field strength, a condition that is met at a diameter of about one-half of the sensitive diameter of hydrogen. The hydrogen diameter of 13.5 inches has been chosen to contain the potential sensitive volume for sodium with a diameter of 6.75 inches entirely within the tool. Therefore, this invention has the added advantage that it is not sensitive to sodium in the borehole fluid. It should be obvious to someone skilled in the art to scale the resonance diameters appropriately for tools used in different-sized boreholes.

The above-described advantage with respect to the completely-in-formation sensitive zone is made possible by combining the constant gradient tubular magnet with a nonmagnetic metal drill collar, an axially elongated antenna, high electrical conductivity shielding for the antenna, and a ferrite buffer. Although other practitioners in the art were of the opinion that this invention would not work with a metal drill collar, the inventors have demonstrated the contrary. A metal drill collar is desirable to increase the tool's strength and durability in the harsh downhole environment of high temperatures, pressures, and abrasive fluids and particles and corrosive fluids. The antenna of this invention, which is used both to transmit the RF pulses and to receive the NMR signals, is located on the outside of the drill collar and, along with the magnet, has a relatively long axial dimension to produce a sensitive volume having a large axial dimension, as described above. In one embodiment, a shield made of high conductivity material (such as copper) is placed between the outer surface of the metal drill collar and the antenna to reduce acoustic ringing of the metal drill collar due to the RF pulses and to increase the efficiency of the antenna during the transmission of the RF pulses. The shield is thin enough to attenuate surface acoustic waves in the shield, yet it is fixed to the collar firmly enough to prevent bulk vibration of the shield. Further, the shield is acoustically isolated from the collar to prevent surface acoustic waves in the shield. These acoustic and vibration characteristics are enabled by bonding the shield to the collar with a thin layer of material having the desired acoustical properties, such as rubber or lead-filled epoxy. In another embodiment, the outer surface of the drill is made highly conductive, so that there is no need for a separate shield.

Further, in accordance with this invention, a layer of ferrite material is placed between the antenna and the shielding to direct the pulsed RF magnetic fields into the formation and to further increase the efficiency of the antenna so that it requires less power in the transmission mode and has increased sensitivity in the receive mode. Preferably, the ferrite material is layered such that a more or less continuous path through the ferrite material exists along the magnetic field lines of the RF field, but repeated discontinuities are introduced in the transversal direction to the RF magnetic field lines. These features in combination enable the placement of the sensitive zone far enough away from the tool to be completely in the formation yet still allow accurate sensing of the NMR signal by the antenna.

Yet another aspect of this invention involves a high-current, low-impedance feed through connector to connect the antenna to the antenna's tuning capacitors. As in the prior art, tuning capacitors are utilized in the antenna electronics (driving circuitry) to match the impedance of the antenna so that the antenna will resonate at the desired frequency. However, the capacitors are sensitive items and require protection from the high pressures and temperatures of the borehole environment. Before the invention described in U.S. Pat. No. 5,557,201, this problem was solved by selecting capacitors with minimal pressure and temperature sensitivities and isolating the capacitors from the borehole fluids in an oil-filled compartment of the drill collar. The compartment seal separated the compartment from the borehole fluids, but the seal did not form a pressure seal and therefore the compartment saw the ambient borehole pressure. Consequently, the compartment was filled with oil to transmit the ambient pressure uniformly around the capacitors and thereby prevent them from being crushed by the high differential pressure. Moreover, because the oil expands and contracts with changing temperature and pressure, these prior art devices had to include a means of varying the volume of the compartment to compensate for the temperature and pressure changes. Thus, such a scheme was very cumbersome.

The '201 invention solved this problem by housing the antenna driving circuitry in a compartment that is not only sealed off from the borehole fluids but is also sealed off at constant atmospheric pressure. Thus, the compartment is simply filled with air instead of oil, and there is no need for a volume-regulation device. This method of protecting the capacitors makes the manufacturing of the tool much simpler and less costly. However, because the pressure in the vicinity of the antenna is much higher than the pressure in the capacitor compartment, the apparatus for feeding the antenna into the capacitor compartment must withstand a severe pressure differential. With such a high pressure differential, one would desire to minimize the area of the feed-through apparatus to minimize the force acting on it. On the other hand, because this NMR measurement-while-drilling (MWD) tool requires a very high current in the antenna, the area of the feed-through apparatus must be large enough to accommodate a conductor of sufficient size to meet the high current requirement. Additionally, the feed-through area must be large enough to supply a sufficient gap between the two antenna wires as well as to any surrounding metallic material.

This invention solves the problem posed by these conflicting area requirements by providing a conductor with a corrugated-shape cross-section for the feed-through connector. The corrugated shape of the conductor provides sufficient size to carry the high current, yet the conductor requires much less feed-through area for the connector than that which would be required for a conventional, flat cross-section conductor. Thus, this corrugated design minimizes the force on the feed-through connector while still accommodating the necessary current. Moreover, the corrugated design improves the bond between the conductor and the surrounding connector material by providing more bonding area. The connector maintains a stripline interface, thereby minimizing stray magnetic fields and electromagnetic losses.

Yet another aspect of this invention involves a method of mounting the electronics in the outer portion of the drill collar in such a way as to minimize the drill collar stresses that are transferred to the electronics. In the borehole, the drill collar is frequently subjected to bending stresses, axial stresses, and torsional stresses. Thus, while one side is in compression, the other side is in tension, and the highest stresses are in the outer portion of the drill collar. Because the drill collar rotates during drilling, the drill collar undergoes many cycles of tensile and compressive stresses. Therefore, any structure that is fixedly mounted to the drill collar will be subjected to similar strains as the collar material undergoes at the mounting surface, and the strains will be highest in the outer portion of the drill collar. Hence, the outer portion of the collar would seem to be an undesirable location to mount the delicate electronics.

This invention allows the installation of the electronics in the outer portion of the drill collar by means of a mounting scheme wherein the stresses of the drill collar are not appreciably transferred to the electronics. Specifically, one of the two ends of the electronics module is fixedly mounted to the drill collar, but the second end is mounted to the collar with a sliding connection. Thus, as the drill collar bends, elongates, and otherwise develops stresses, the second end of the electronics module slides relative to the drill collar and therefore the electronics module remains relatively free of the drill collar stresses. By virtually eliminating the transferred stresses, this invention allows the installation of the electronics in the outer portion of the drill collar and greatly reduces the potential strain and fatigue problems, such as broken printed circuit board traces and broken leads on components due to over-stress.

Finally, the NMR MWD tool embodying this invention requires very high downhole power within a very short time period. Specifically, it requires about 1.5 kilowatts during the short duration of an NMR measurement, but only a few watts between measurements For example, a typical load change would be 1 kW for 10 mscc, 50 W for three seconds, 1 kW for 10 msec, and so on. Before this invention, existing downhole power generators were not directed to meeting these kind of fluctuating power requirements. Therefore, the apparatus embodying this invention includes a high power generator to meet the need.

Accordingly, it is an object of this invention to provide an improved apparatus and method for performing a full range of NMR measurements on formations surrounding the borehole in particular while drilling that address the above issues and overcome deficiencies associated with the prior art.

BRIEF DESCRIPTION OF THE DRAWINGS

This invention may best be understood by reference to the following drawings, in which like reference numerals designate like elements:

FIG. 9 is an algorithm block-diagram of the motion management method used in accordance with a preferred embodiment of the present invention.

FIGS. 10A(1)-(6), 10B(1)-(6), 11A(1)-(6), 11B(1)-(6), 12A(1)-(6), 12B(1)-(6), 13A(1)-(6) and 13B(1)-(6) show plots of the lateral motion of the apparatus of FIG. 1 in different motion regimes.

FIGS. 33(a) and 33(b) are timing diagrams for two versions of Carr-Purcell-Meiboom-Gill pulse-echo sequences used for NMR measurements in accordance with a preferred embodiment of this invention.

DETAILED DESCRIPTION OF THE PREFERRED EMBODIMENTS

In the following description of the preferred embodiments Section A focuses on the components of the NMR measurement tool in accordance with a preferred embodiment of this invention, Section B provides a brief description of the preferred embodiment for the NMR measurement method of the present invention using motion management to compensate for tool motions during NMR logging operations.

(A) The NMR Tool

There are two versions of modern pulse-NMR logging tools in use today: the centralized MRIL® tool made by NUMAR Corporation, and the side-wall CMR tool made by Schlumberger. The MRIL® tool is described, for example, in U.S. Pat. 4,710,713 to Taicher et al. and in various other publications including: "Spin Echo Magnetic Resonance Logging: Porosity and Free Fluid Index Determination," by Miller et al., SPE 20561, 65th Annual Technical Conference of the SPE, New Orleans, La., Sep. 23–26, 1990; "Improved Log Quality With a Dual-Frequency Pulsed NMR Tool," by Chandler et al., SPE 28365, 69th Annual Technical Conference of the SPE, New Orleans, La., Sep. 25–28, 1994). Details of the structure, the operation and the use of the MR tool are also discussed in U.S. Pat. Nos. 4,717,876; 4,717,877; 4,717,878; 5,212,447; 5,280,243; 5,309,098; 5,412,320; 5,517,115; 5,557,200 and 5,696,448 all of which are commonly owned by the assignee of the present invention. The Schlumberger CMR tool is described, for example, in U.S. Pat. Nos. 5,055,787 and 5,055,788 to Kleinberg et al. and further in "Novel NMR Apparatus for Investigating an External Sample," by Kleinberg, Sezginer and Griffin, J. Magn. Reson. 97, 466–485, 1992. The interested reader is directed to the disclosure of these patents for relevant background information. Accordingly, the patents listed above are hereby incorporated by reference for all purposes.

Figure 1:
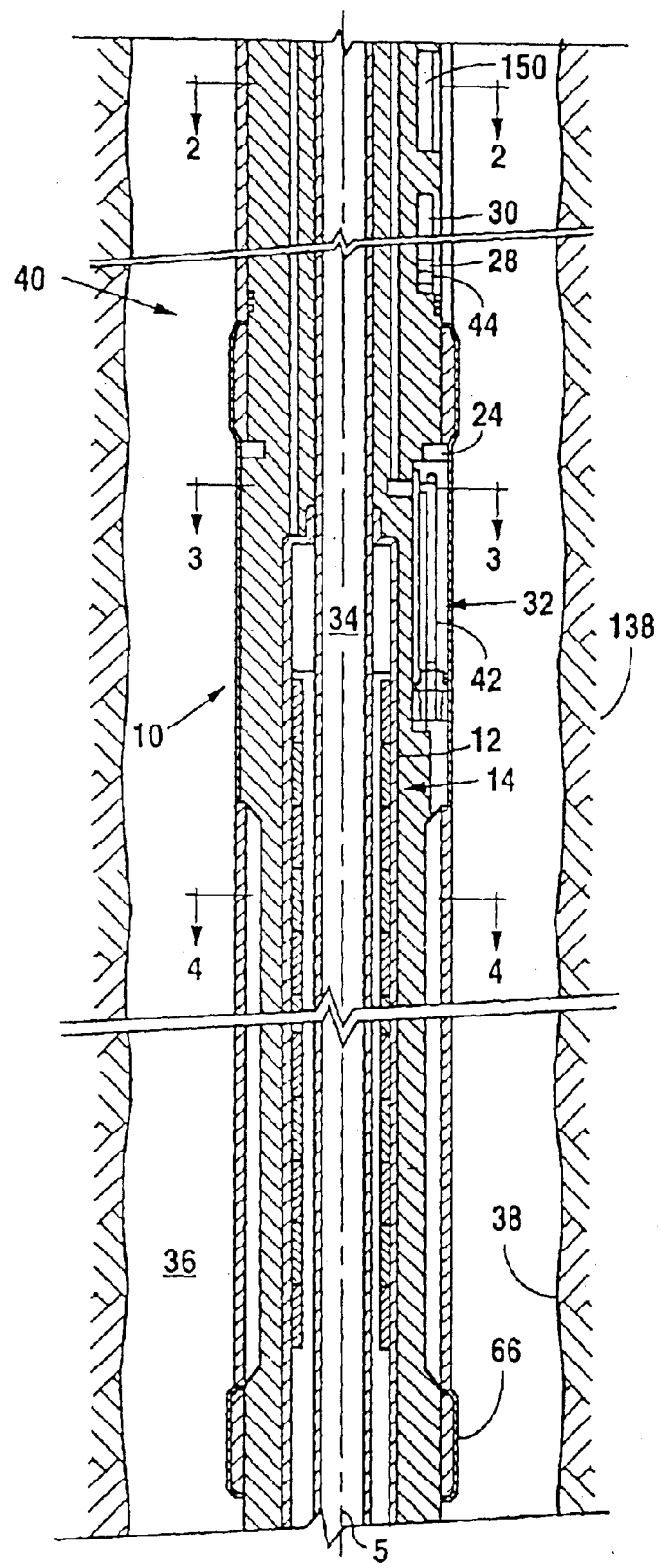
FIG. 1 is a schematic axial cross-sectional view of an apparatus constituting a preferred embodiment of the apparatus of this invention.
Figure 2:
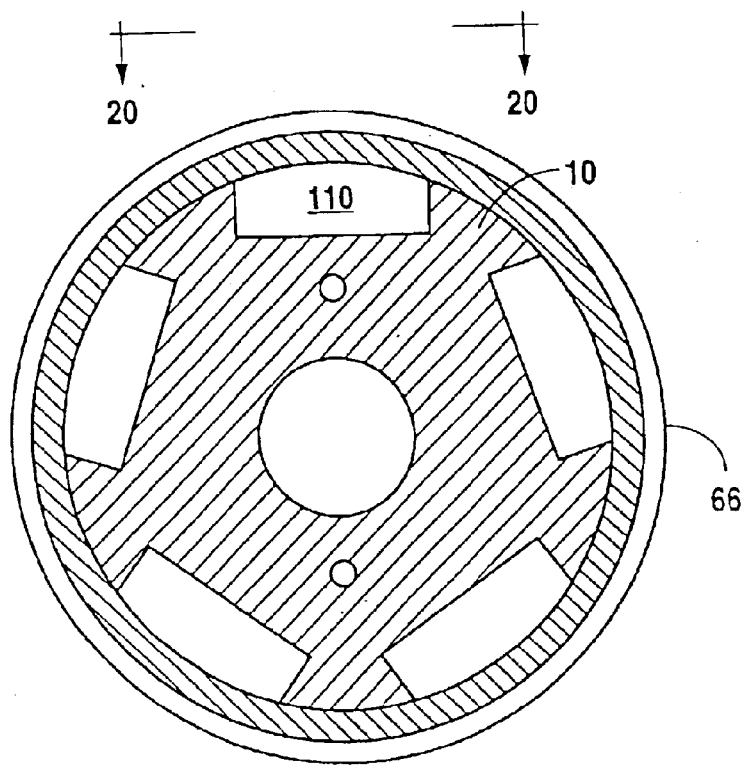
FIGS. 2, 3, 4 and 4B are diametrical cross-sectional views of the apparatus shown in FIG. 1 respectively on planes 2—2, 3—3 and 4—4.
Figure 3:
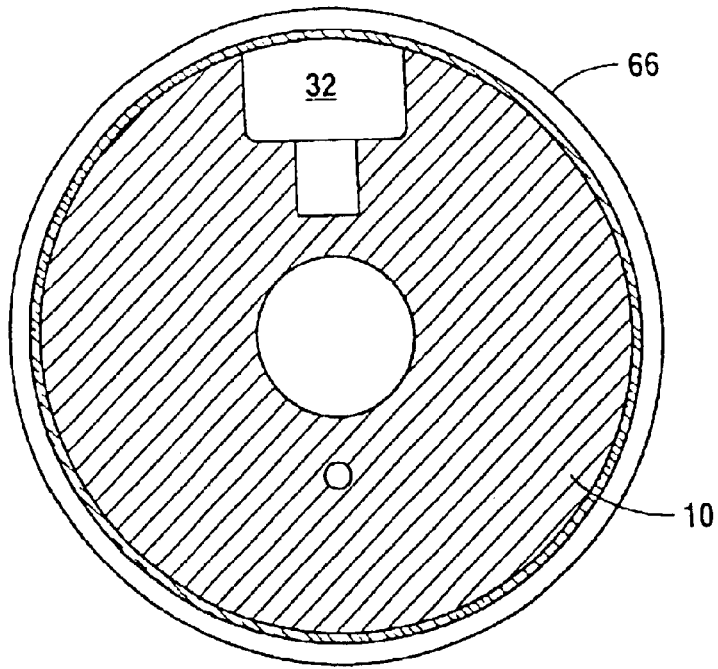

Referring to FIG. 1, it illustrates an improved NMR MWD tool 40 used and operated in accordance with a preferred embodiment of the present invention. NMR tool 40 comprises a non-magnetic metal drill collar 10 that encloses a tubular, permanent magnet 12, which surrounds a mud tube 34 through which drilling mud may be pumped during the drilling of a borehole 36 into the earth formation 138. The tool 40 further comprises a stabilizer section 66, antenna 14, magnet section 12, capacitor compartment 32 with tuning capacitors 42, accelerometers 24, antenna driver 28, signal processor 30 and data transmitter 150. Some of these components are known in the art and have been described generally, for example, in the prior art publications discussed in the preceding section, which are incorporated by reference. In the sequel, various improvements to these components of the tool and their functions are described in more detail in accordance with the preferred embodiments of the present invention.

(1) The Magnet

Figure 6A:
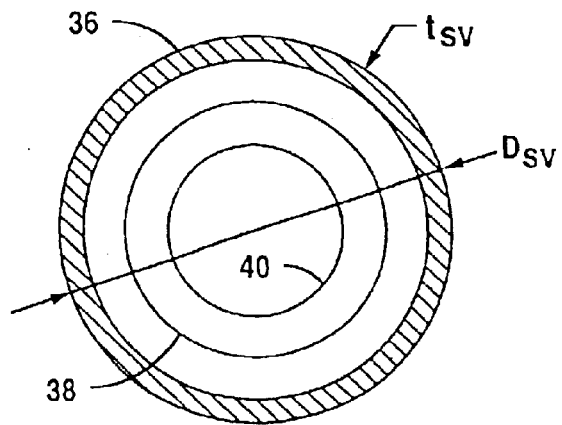
FIG. 6A is a schematic sectional view showing the sensitive volume produced by the apparatus of FIG. 1.
Figure 6B:
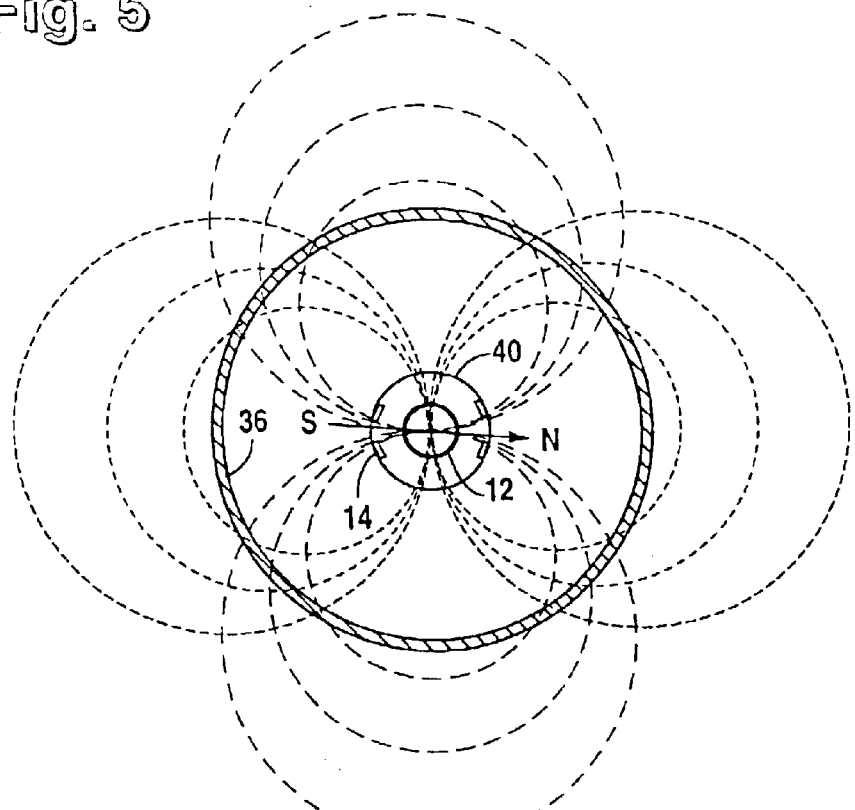
FIG. 6B is a schematic sectional view similar to FIG. 6A but showing the magnetic flux lines produced by the apparatus of FIG. 1.

In accordance with the present invention, the magnet 12 of NMR tool 40 is polarized such that a static magnetic field $B_0$ illustrated in further detail in FIG. 6B, is produced in the earth formation 138 that is substantially transversally oriented with respect to the longitudinal axis 5 of the tool. As shown in FIG. 6B, the magnetic field of the tool in accordance with the present invention can be modeled as that of a linear dipole. The magnet 12 is preferably fabricated from highly stable rare-earth material combinations, such as samarium-cobalt or neodymium-iron-boron. Custom-shaped blocks can be obtained, for example, from Magnetfabrik Schramberg, Schramberg, Germany.

In a preferred embodiment, the length of the magnet 12 is about four feet (1.2 meters), of which in a preferred embodiment only the center two feet (0.6 meters) are used for the NMR measurement. In accordance with the present invention, the additional one-foot sections at each end provide a way to pre-polarize the hydrogen nuclei in the formation and to establish nuclear polarization equilibrium before a portion of the formation enters the measurement volume. Due to the symmetric nature of magnet 12 and the measurement volume for the tool built in accordance with the present invention, the NMR response is independent of the direction (i.e., upward or downward) in which the tool moves.

Figure 4:
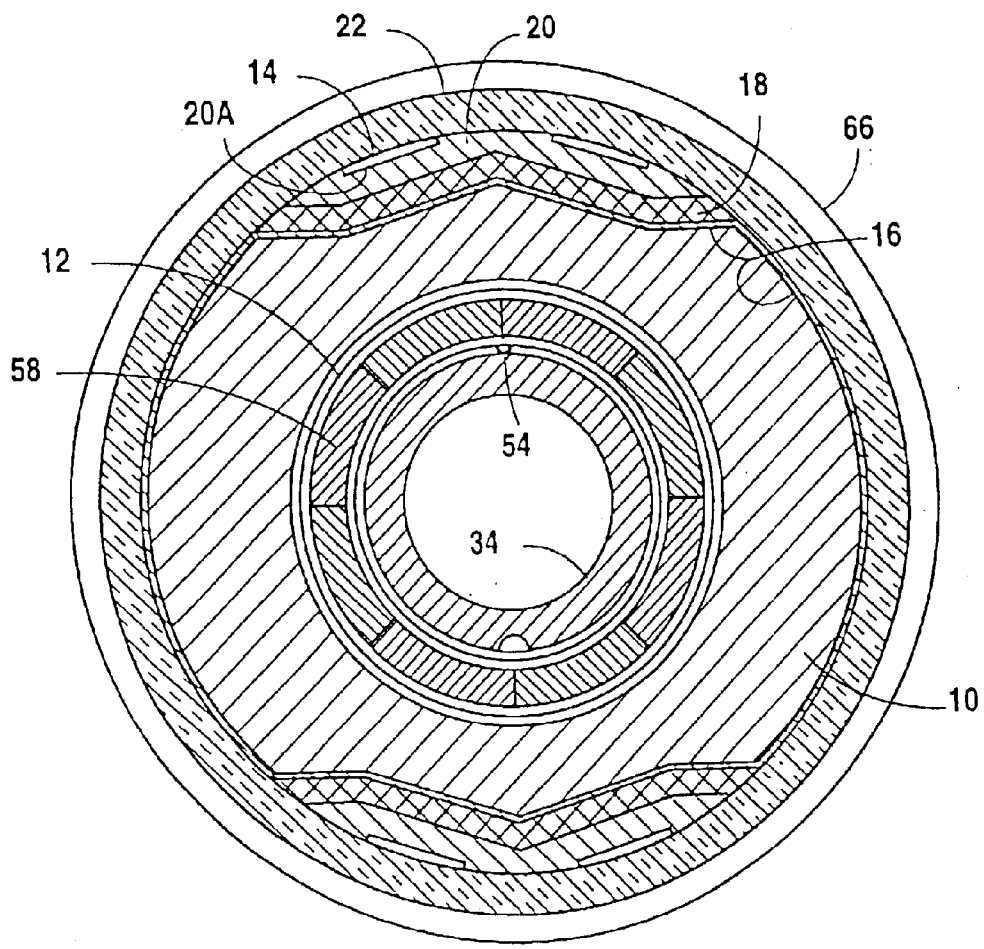
Figure 19:
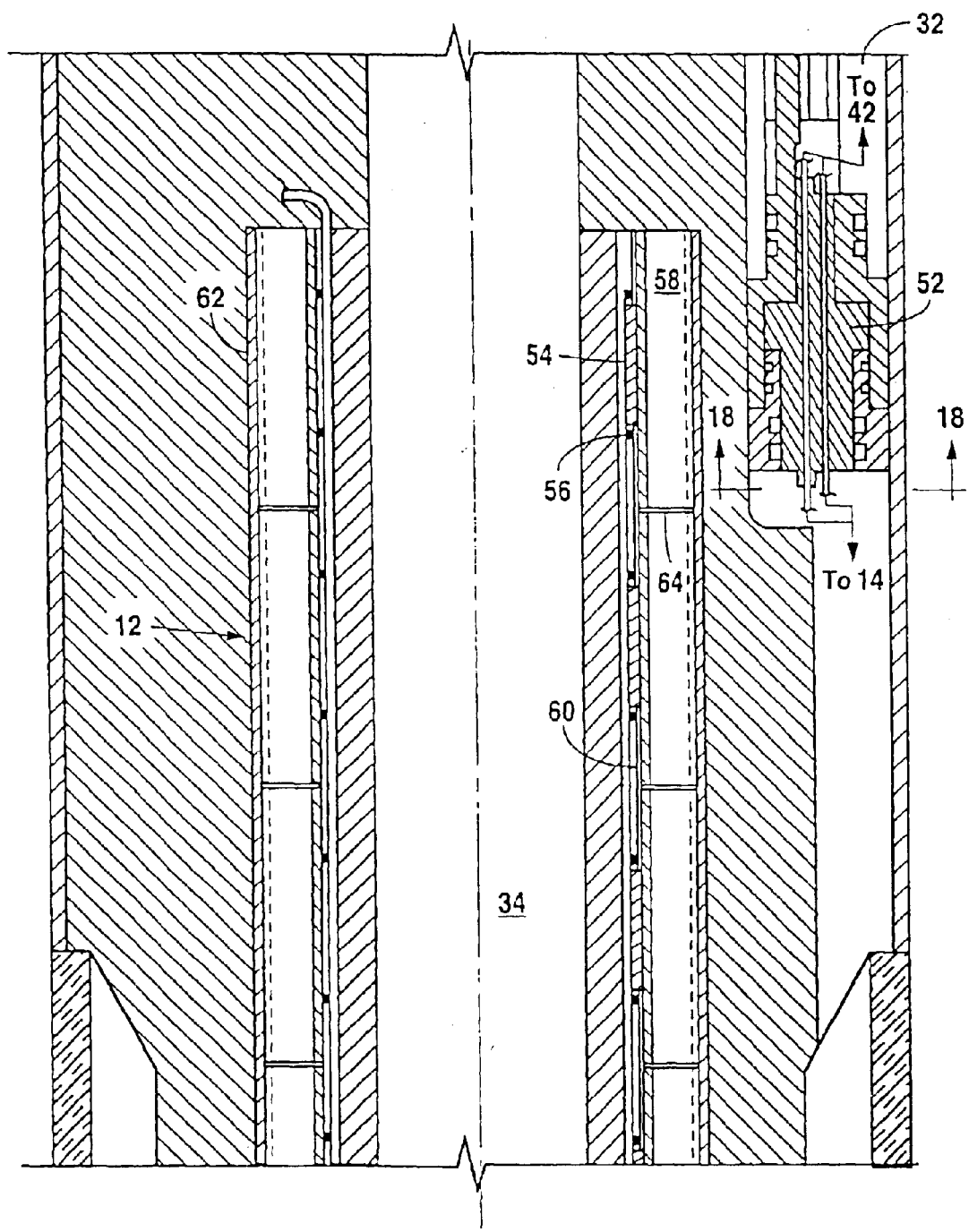
FIG. 19 is an enlarged axial cross-sectional view of a portion of the apparatus of FIG. 1 showing the magnet assembly and feed-through connector.
Figure 20:
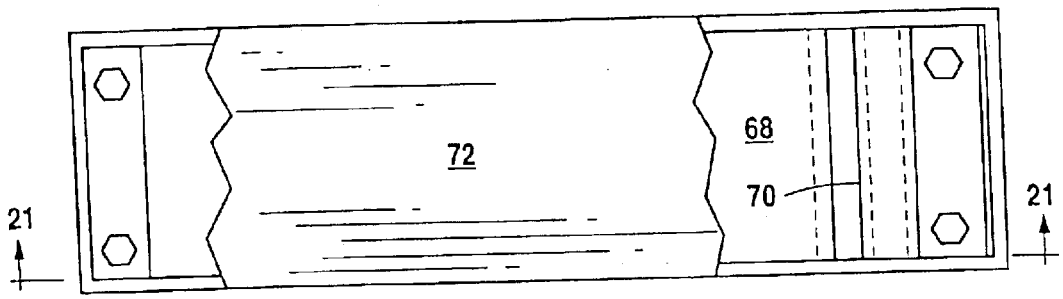
FIG. 20 is a schematic elevational view of an electronics compartment.
Figure 21:
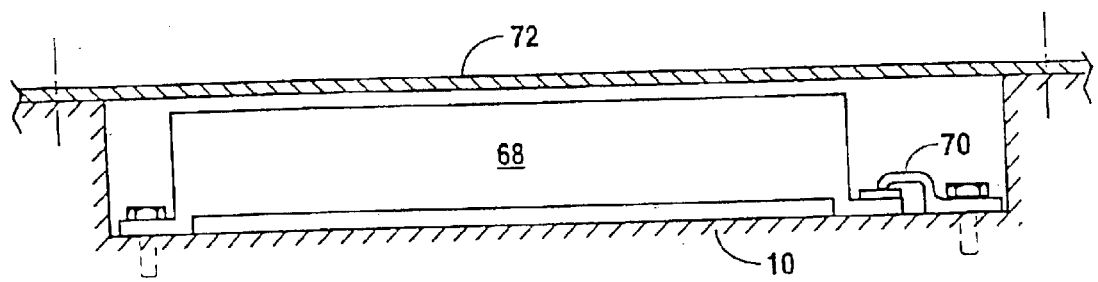
FIG. 21 is a schematic sectional view showing the assembly of the reduced-stress electronics mounting apparatus in the drill collar.
Figure 22A:
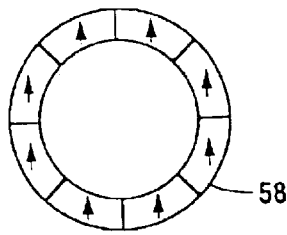
FIG. 22 contains two schematic cross-sectional views of the permanent magnet magnetized uniformly and nonuniformly.
Figure 22B:
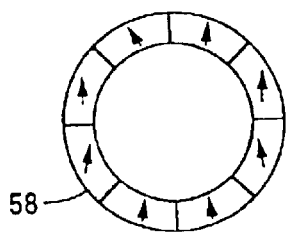
Figure 23:
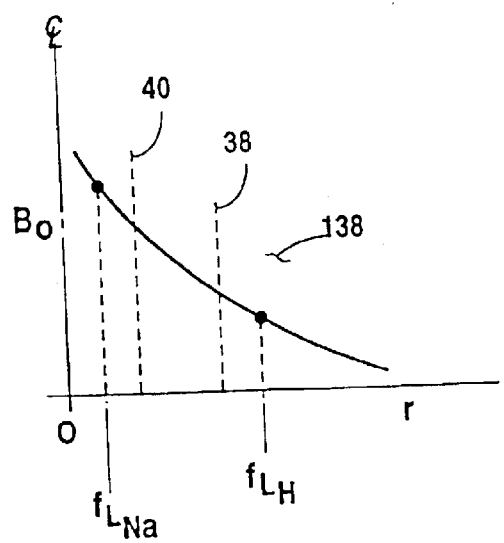
FIG. 23 is a graph showing the static magnetic field versus radial distance from the tool for the apparatus of the present invention.

As best seen in FIGS. 4 and 19, the magnet 12 in a preferred embodiment comprises a plurality of magnet segments 58. Axially, the magnet segments 58 are separated by magnet spacers 64, preferably made of silicone foam, which are installed with a compressive preload. Circumferentially, the magnet segments 58 are bonded to an inner magnet sleeve 60 and an outer magnet sleeve 62. In a specific embodiment, each axial section of magnet segments is held in proper circumferential alignment by means of a key 54 pressed into a longitudinal slot formed in the mud tube 34 and inner magnet sleeve 60. Thus, in a preferred embodiment the magnet 12 is segmented both axially and circumferentially. The axial segmentation provides improved static and dynamic loadhandling capability. The magnet 12 is installed over the mud tube 34, and a plurality of O-rings 56 are installed in the small gap between the mud tube 34 and inner magnet sleeve 60. The O-rings 56 provide a means for handling radial expansion, isolate the magnet from distortions of mud tube 34, and also help to hold the magnet 12 in place axially.

In the preferred embodiment, the magnet segments are made from samarium-cobalt, although for temperatures below about 160° C. alternative embodiments, such as neodymium-iron-boron segments would also be a suitable and less expensive choice. In accordance with the present invention, the shaping of the magnetic field outside the tool is accomplished inpart by grinding the individual samarium-cobalt segments into individual shapes and volumes. In particular, ferrite material layers are 18 mounted in a preferred embodiment over the north and south sides of the magnet and have the effect of partially short-circuiting the static magnetic flux. In order to achieve a magnetic field of uniform and sufficient magnitude within the sensitive volume, in a preferred embodiment it is necessary to: (a) slightly increase the volume of all magnetic segments, and (b) to selectively increase the segment volume on the north and south sides at the expense of east and west sides, because it is the former sides that are mostly affected by the presence of ferrite layers 18.

Figure 4A:
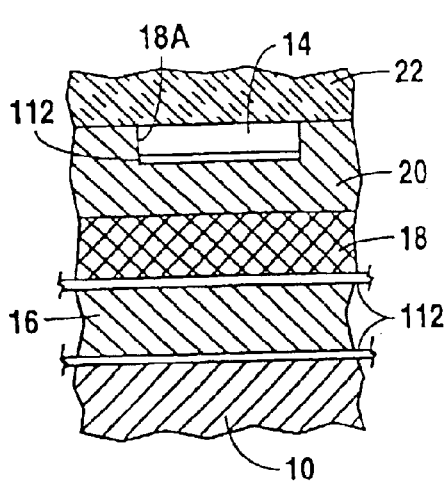
FIGS. 4A, 4C and 4D illustrate bonding layers used in accordance with the present invention.
Figure 4B:
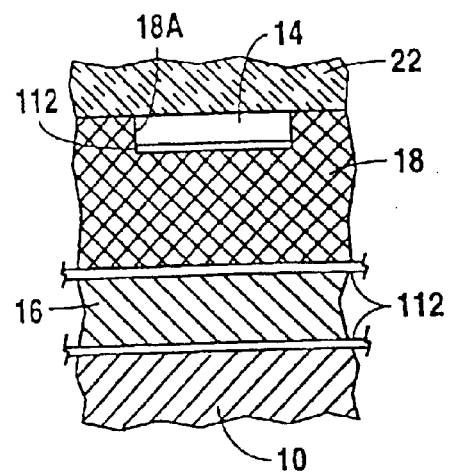
Figure 4C:
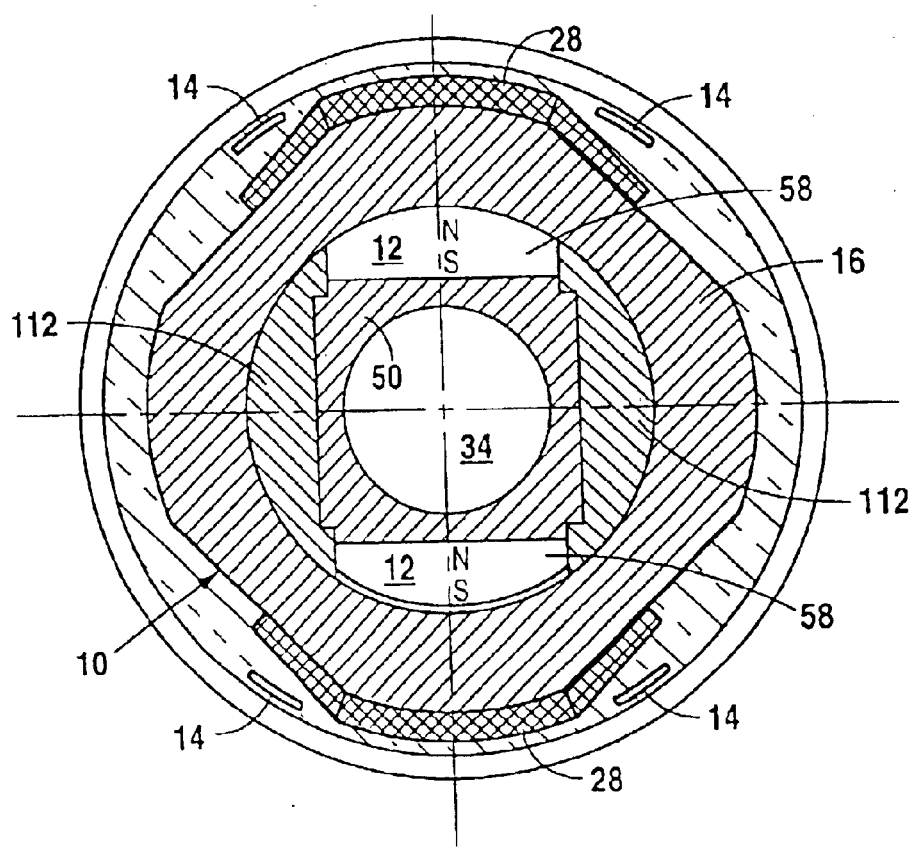

A modification to the cross section 4—4 in FIG. 1, as shown in a specific embodiment in FIG. 4 is illustrated in FIG. 4C. The arrangement illustrated in FIG. 4C is particularly advantageous because it achieves the mechanical strength of the embodiment shown in FIG. 4, combined with a simplified geometry for the magnet 12. In the embodiment illustrated in the figure, the magnet 12 is comprised of magnetized segments 58 made from samarium-cobalt. These magnetized segments are bonded to the flat sides of a magnet segment carrier 50, which is made from magnetically permeable steel (type 4130). In accordance with the present invention, the magnet segment carrier 50 is hollow to accommodate the mud tube 34, which encloses the flow channel. The orientation of magnetization is generally along the N-S direction, as indicated in FIG. 4C. The magnet segment carrier 50 generally becomes magnetized in the same N-S direction. The aforementioned pre-compensation of the magnetic field is easily accomplished, for example, by shortening or elongating the magnet carrier 50 along the N-S and/or along the E-W direction, respectively.

(2) Ferrite Material Layers

In order to improve the performance of the antenna 14 of the tool in the receive mode as well as the transmit mode, in accordance with a preferred embodiment of the present invention an axially elongated layer of ferrite material 18 is installed between the shield 16 and the antenna 14, as shown in FIGS. 4, 4A, 4B, 4C and 4D. Generally, the ferrite material layer 18 shapes the radio frequency (RF) field, by offsetting the reduction in the antenna aperture due to shield 16. Without the ferrite layer 18, large eddy currents would be induced in shield 16, which would tend to oppose the antenna currents and would result in significantly reduced sensitivity in receive mode and in much larger current and power requirements in transmit mode.

Further, it is important to note that the field generated by the magnet 12 is not rotationally symmetric in its amplitude. Rather, in a preferred embodiment, the design and construction of the magnet takes into account the effect of the soft-magnetic ferrite material layer 18, which is mounted over both the north and the south poles of magnet 12. Ferrite material must be used that does not magnetically saturate in the presence of the strong static field surrounding the magnet. Base materials for ferrites 18 that can be used in a preferred embodiment are 3F3 and/or 3F4. Although the ferrites 18 are employed in accordance with the present invention to shape the radio frequency field, it will be appreciated that they also distort the static magnetic field. Accordingly, in the present invention the main magnetic field can be pre-compensated such that the combined field from the magnet and the ferrites is essentially rotationally symmetric in its magnitude within the measurement volume. In a preferred embodiment this can be accomplished by selectively altering the volume of magnetic material on the north and south sides vs. the amount on the east and west sides of the magnet. Alternatively, or in combination with the above approach, the size of the ferrites can also be optimized for length and width to increase absorption and/or destructive reflections. In a specific embodiment the ferrites 18 can also be staggered like a brick wall for the same purpose. The required modifications of the magnet shapes are preferably determined by numerical modeling, such as provided by commercial packages, of which ANSYS is an example.

Figure 4D:
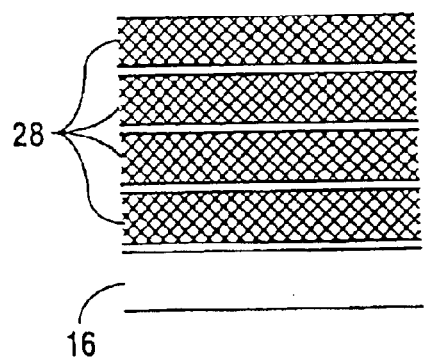

As shown in the detail FIG. 4D, in a preferred embodiment of the present invention the ferrites 28 are actually comprised of layers of ferrite material, bonded by lead impregnated epoxy resin. In a preferred embodiment, the ferrite material layers are about 0.050" thick, while the epoxy resin is about 0.015" thick. The layers are oriented such that a more or less continuous path exists for the magnetic component of the RF field. In such an arrangement, the RF magnetic field experiences little attenuation as it passes through the ferrite. On the other hand, magneto-acoustic vibrations, which are introduced by the RF pulse, are optimally dampened because the acoustic wave repeatedly experiences absorption and/or destructive reflection on the interfaces between the ferrite material and the bonding layers.

As known in the art, commercially available ferrite is physically porous as well as magnetically permeable and is therefore prone to destruction under the typically high borehole pressures. Additionally, nonisostatic pressure changes the permeability of ferrite, which in turn changes the resonant frequency of the antenna 14. Therefore, the ferrite 18 is preferably impregnated with epoxy resin under pressure and temperature as described, for example, in U.S. Pat. No. 5,644,231 to Wignall. In the alternative, the ferrite layer 18 can be prepared by hot isostatic pressure methods to press out all the voids in the ferrite. As with the interface between the drill collar 10 and the shield 16, the preferred method of mounting the ferrite layer 18 to the shield 16 in accordance with the present invention is by bonding a thin layer 112 (FIG. 4A) of rubber or lead-filled epoxy between the shield 16 and ferrite layer 18. This thin layer 112 of rubber or lead-filled epoxy serves to acoustically decouple the shield 16 from the ferrite layer 18.

(3) The Antenna

Figure 5:
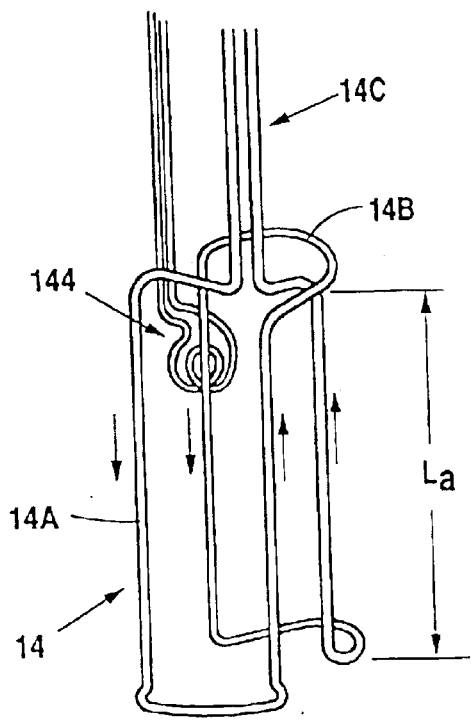
FIG. 5 is a schematic perspective view showing the configuration of the antenna for the apparatus illustrated in FIG. 1.

In accordance with the present invention, the length of the measurement volume is defined by the aperture of the antenna 14 and in a preferred embodiment is about two feet (0.6 m) long. In the preferred embodiment of the tool illustrated in FIG. 1 the antenna is used both for the transmission of radio frequency (RF) pulses into the surrounding formation 138 and for receiving NMR signals from the formation. In accordance with the present invention antenna 14, also illustrated in a schematic view in FIG. 5, is preferably made of flat, elongated copper strips 14A interconnected by peripherally extending copper strips 14B about 1 inch wide and about 0.030 inch thick, and is mounted on the external surface of the drill collar 10 along the same axial portion of the tool as the magnet 12. The antenna is fed by a transmission line 14C made from two copper strips separated by a thin layer of suitable dielectric material. In a preferred embodiment, antenna 14 is completely encapsulated with a protective coating, which is preferably made of vulcanized viton rubber or a thermoplastic composite material.

Antenna-Magnet Coupling

In accordance with the present invention it is very important to provide semi-rigid coupling between antenna 14 and permanent magnet 12. If this is not the case, relative movement of the antenna against the static magnetic field will induce an electric voltage in the antenna windings. Although such a voltage would be small, it could still be large compared with the voltages induced by NMR signals, and would have a deleterious effect on the accurate measurement of the latter. As can be seen in FIG. 4, the magnet 12 is rigidly coupled to the drill collar 10 using locking.

Despite the potential deleterious effect on the NMR signal, it has been demonstrated by experimentation that it is still advantageous to partially de-couple the antenna from the drill collar 10 through shield 16 and antenna mounting 20. Generally, this de-coupling is believed to provide a measure of isolation from the effects of dynamic geometry changes, such as cyclical bending and torsion variations in collar 10, and high-frequency vibrations created by the drilling process and transmitted through the collar.

Mounting of the Antenna

The best known method for mounting the antenna 14 onto the drill collar 10 is by first installing an antenna mounting 20 made of an electrical and structural insulator material, such as a fiber-reinforced epoxy or thermoplastic composite, onto the ferrite 18 using another thin bonding layer 112 (See FIG. 4A). A recess 20A is formed in the outer surface of the antenna mounting 20 for accepting the antenna 14, which is bonded to the antenna mounting 20 with yet another thin bonding layer 112. Alternatively, as shown in FIG. 4B, the antenna 14 may be installed directly to the ferrite layer 18, without an intervening antenna mounting 20, using a thin bonding layer 112. In such case, a recess 18A is formed in the ferrite layer 18 for accepting the antenna 14. In either case, the antenna 14 is preferably covered with an antenna cover 22 in the form of a replaceable sleeve to protect the antenna 14 from the borehole environment. The preferred material for the antenna cover 22 is also a fiber-reinforced epoxy or thermoplastic composite. With further reference to FIG. 1, in a preferred embodiment the antenna cover 22 is held in place by a stabilizer 66 installed at each end of the antenna cover 22. These stabilizers 66 are preferably made of shrink-on material that allows installation by heating the stabilizers, sliding the stabilizers onto the drill collar 10, and allowing the stabilizers 66 to contract, or shrink, upon cooling. In addition to holding the antenna cover 22 in place, the stabilizers, which have an outer diameter larger than that of the antenna cover 22, serve to minimize damage to the antenna cover 22 due to rubbing and bumping against the borehole wall 38.

When installed in this manner, the antenna 14, shield 16, ferrite 18, and magnet 12 cooperate electromagnetically to produce an annular NMR sensitive volume 36, as shown in FIGS. 6A and 6B. In a preferred embodiment, the sensitive volume 36 has a nominal diameter $D_{sv}$ of about 13.5 inches (0.34 m), a radial thickness $t_{sv}$ of about 1.5 mm, and an axial length of about 2.0 feet (0.6 m). With reference to FIG. 1, this relatively large nominal diameter allows the sensitive volume to be entirely within the formation 138, yet the antenna is efficient enough to accurately detect the NMR signals at this distance. Additionally, the static magnetic field of this invention as a function of radial distance from the tool is such that the location of the larmor frequency for the sodium quadruple moment lies inside the tool volume instead of in the borehole 36 or in its wall 38. Therefore, in an important aspect of this invention, sodium signal is prevented from developing in the borehole fluid.

As illustrated in a specific embodiment in FIG. 4, the diameter of antenna cover 22 is slightly less than the largest tool diameter. The largest tool diameter is defined by metallic stabilizers (66) that are mounted above and below the sensor section of the tool. If no stabilizing action is desired, hardened wear bands may be substituted for the stabilizers. The beneficial effect of stabilizers and/or wear bands used in accordance with the preferred embodiment is that the antenna cover 22 typically does not come into contact with the borehole wall 38. Wear bands are replaceable in the field and can be renewed between runs into the hole. It is also envisioned that metallic rings, such as stabilizers and/or wear bands, are placed immediately adjacent to the main antenna, such that in operation only the center two feet of antenna cover 22 remain exposed.

(4) The Drill Collar

FIGS. 4 and 4C, which show cross-sections along line 4—4 in FIG. 1, show two different embodiments of the drill collar 10 used in accordance with the present invention. Specifically, in the embodiment shown in FIG. 4, the collar 10 has a "wing-shape" cross section. FIG. 4C, on the other hand, illustrates an embodiment with an octagonal cross-section design. Generally, it is important to note that the ferrites 28 are shaped to conform to the outer surface of the drill collar. In the embodiment illustrated in FIG. 4C an electromagnetic shield 16 is realized by plating the drill collar, although an arrangement as shown in FIG. 4A is also possible in an alternative embodiment. Numerous different drill collar cross-section designs are possible in accordance with the present invention, where each variation embodies a particular compromise between the strength of the steel collar 10 and the efficiency of the antenna 14.

(5) Conductive Shielding

Referring next to FIGS. 4, 4A-D, in accordance with a preferred embodiment of the present invention a highly conductive shield 16, preferably made of copper, is used between the antenna 14 and the exterior of the drill collar 10. The purpose of this shield is to prevent the RF field from entering the conductive steel collar 10. Otherwise, it will be appreciated that the steel collar would reduce the Q factor of the antenna 14, resulting in diminished signal amplitude in receive mode, and increased power dissipation in transmit mode. In accordance with the present invention the shield 16 is preferably a "floating" equal-potential surface with no direct connection to the collar.

The conductive shield 16, which completely surrounds the drill collar 10 along the axial portion containing the antenna 14, also helps to reduce the ringing of the drill collar 10 due to the strong RF pulses used in NMR measurements. The preferred method for installing the shield 16 onto the drill collar 10 in accordance with the present invention is by bonding a thin layer 112 (FIG. 4A) of material having suitable acoustic properties, such as rubber or lead-filled epoxy, between the collar 10 and the shield 16. In alternative embodiments the shield can be installed using different methods, such as flame spraying, electroplating, by means of mechanical fasteners, or otherwise. In accordance with the present invention the acoustic decoupling material comprising the bonding layer 112, such as rubber or lead-filled epoxy, is desirable as a dampening material for two reasons: (1) it is soft enough to acoustically decouple the shield 16 from the drill collar 10, and (2) it is rigid enough to prevent the shield 16 from vibrating due to the interaction between the current in the antenna 14 and the static magnetic field.

(6) The Tuning Capacitor Compartment

Figure 18:
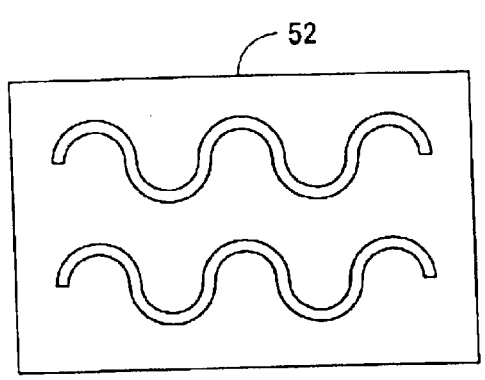
FIGS. 18 and 18A represent schematic cross-sectional views showing alternate embodiments of feed-through connectors.
Figure 18A:
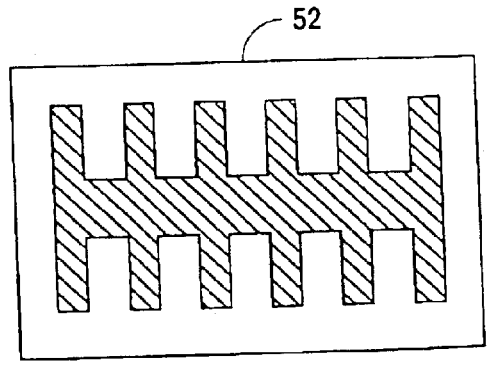

Referring back to FIG. 1, this preferred embodiment also incorporates tuning capacitors 42 housed in a tuning capacitor compartment 32 of the tool 40. The tuning capacitors 42 are used to match the impedance of the antenna 14 so that it will resonate at the desired natural frequency. As described, for example, in U.S. Pat. No. 5,557,201, the tuning capacitor compartment 32 is sealed off from the borehole environment so that the capacitors remain at atmospheric pressure instead of being exposed to the high borehole pressures. This pressure-sealed design eliminates the need for filling the capacitor compartment 32 with oil, as in prior art, to prevent the capacitors from contacting borehole fluids. Additionally, this invention comprises a high-pressure antenna feed-through connector 52, as shown in illustrative embodiments in FIGS. 18 (corrugated cross-section), 18A (multi-finned cross-section) and 19, to provide a conductive path for the electrical current from the antenna 14 to the tuning capacitors 42. The feed-through connector aspect of this invention is discussed in a preferred embodiment in an application filed concurrently herewith.

In accordance with the present invention, by maintaining the capacitor compartment at atmospheric pressure, more pressure-sensitive electronics may be mounted inside the tuning capacitor compartment. This includes, but is not limited to, electromechanical relays and associated driver electronics. Under control of the driver electronics, such relays can be used to add more tuning capacitors to the resonant circuit formed by the fixed capacitors and the antenna. Thereby, the resonant frequency of the resonant circuit can be changed and the system can be made to operate at different frequencies one at a time. Such an arrangement is advantageous because by changing the operating frequency, a different sensitive volume is selected. By using multiple volumes one at a time, more signal can be accumulated in less time and/or different NMR measurement can be performed in a quasi-simultaneous fashion. Reference is made here to the paper "Lithology-Independent Gas Detection by Gradient NMR Logging," by Prammer, Mardon, Coates and Miller, Society of Petroleum Engineers, paper SPE-30562, published in the transactions to the 1995 SPE Annual Technical Conference & Exhibition, pp. 325–336, which is hereby incorporated by reference. In FIG. 6 of this paper, a pulse sequence for an NMR wireline tool is shown that utilizes two measurement volumes at once to affect oil and gas detection.

(7) Power Generation

Figure 24:
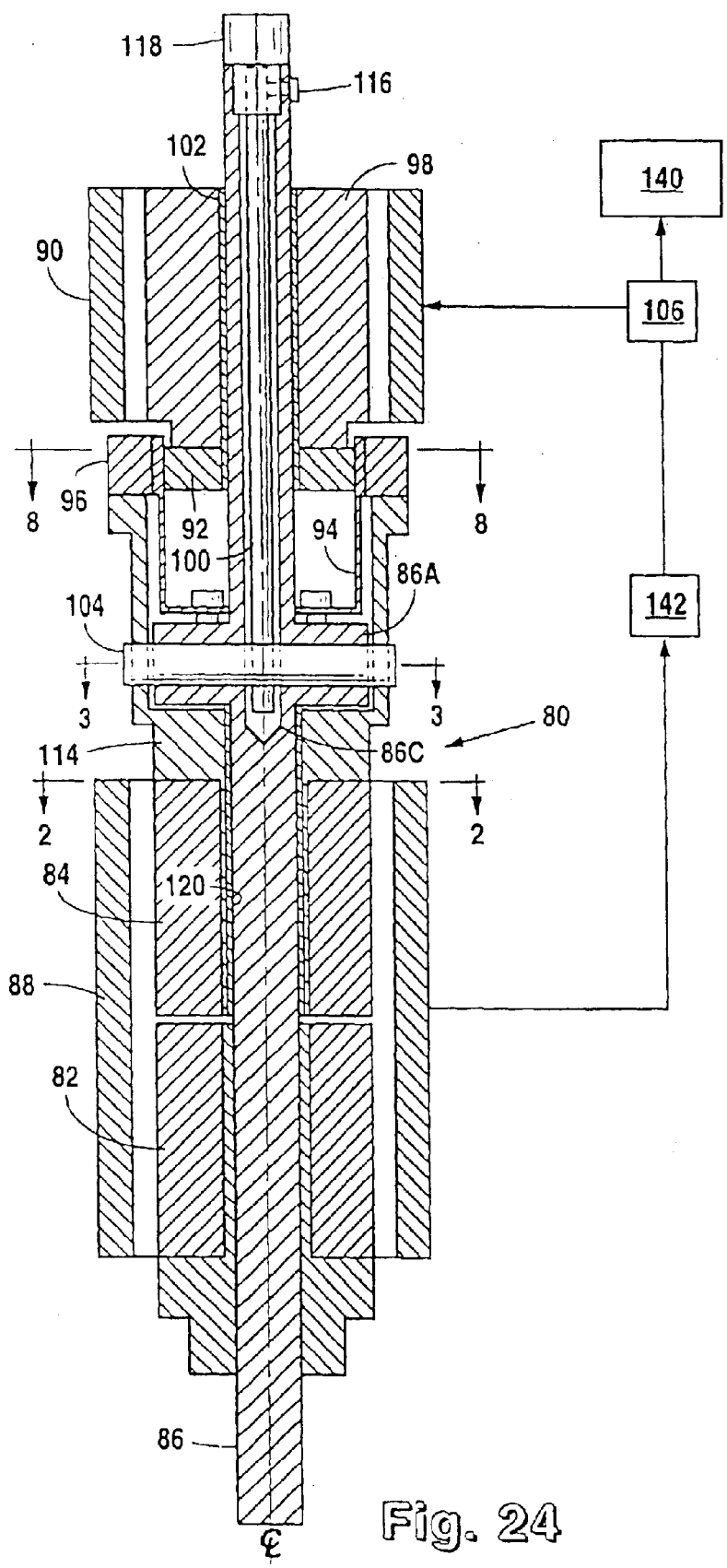
FIG. 24 is a schematic axial cross-sectional view of the power generator used in a preferred embodiment of the present invention.

FIG. 24 illustrates an electric generator 80 in accordance with the present invention for supplying electrical energy to a downhole system 140. Electric generator 80 is driven by a drive shaft 86 that is preferably connected to a conventional mud-powered turbine (not shown) and supported by bearings (not shown). Electric generator 80 comprises permanent magnets 82 and 84, which are preferably of equal length and magnetic strength and which rotate inside a fixed main armature 88 to generate downhole electric energy. Because such electric energy is needed over a widerange of rotation speeds of drive shaft 86 (i.e., the mud-powered turbine) and electrical demands of system 140, the electrical output must be controlled. The present invention controls the electrical output by providing a regulator for varying the relative rotational position of movable magnet 84 with respect to fixed magnet 82. Specifically, fixed magnet 82 is fixedly attached to drive shaft 86, but movable magnet 84 is mounted to a carriage 114 that is mounted to drive shaft 86 with a bearing 120 such that carriage 114 may rotate with respect to drive shaft 86. The degree of relative rotation between carriage 114 and drive shaft 86 is preferably limited by a stop pin 104 as discussed below.

As will be readily apparent to persons skilled in the art, the present invention may be used to generate AC or DC electrical energy. If this invention is used to generate DC electrical energy, a rectifier 142 is provided as shown in FIG. 24 to rectify the output from main armature 88 before it is fed into controller 106 and on to system 140.

Figure 25:
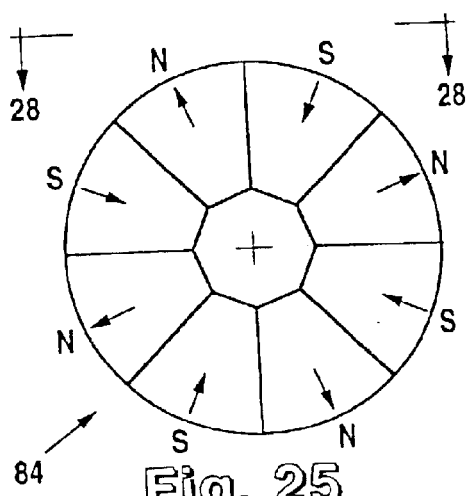
FIG. 25 is a schematic cross-sectional view of the fixed and movable magnets of the power generator.
Figure 26:
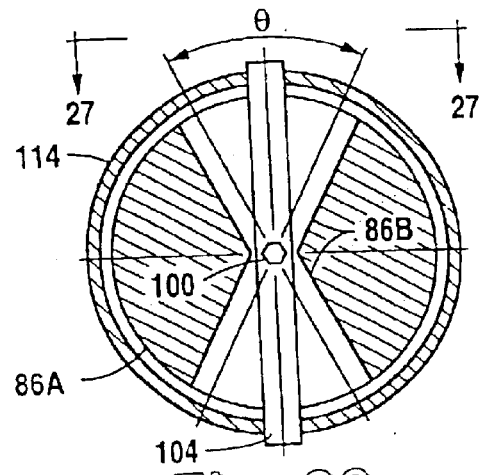
FIG. 26 is a schematic cross-sectional view taken on the plane F26—F26 as shown in FIG. 24.
Figure 27:
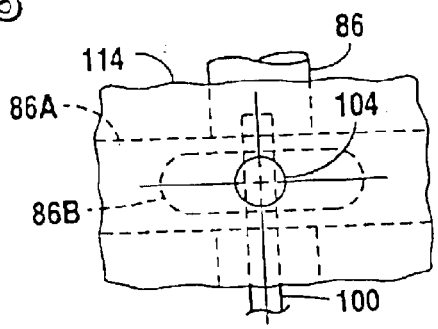
FIG. 27 is a schematic elevational view of the stop pin and cooperating structure.
Figure 28A:
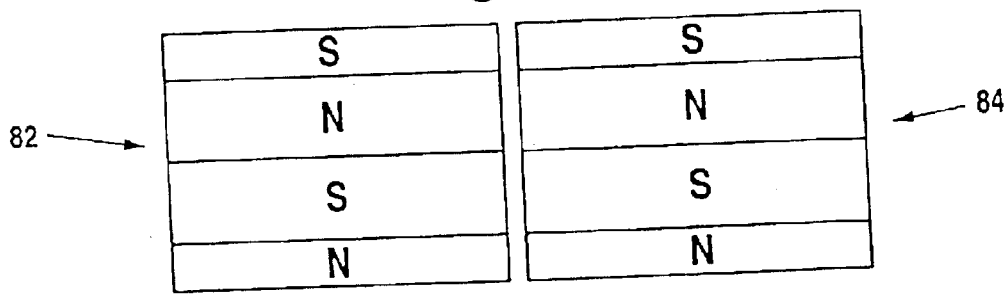
FIGS. 28A and 28B are schematic views showing the relative positions of the fixed and movable magnets of the power generator.
Figure 28B:
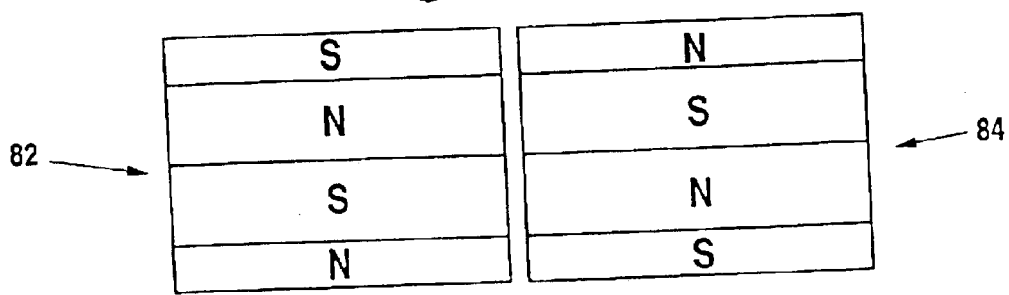
Figure 29:
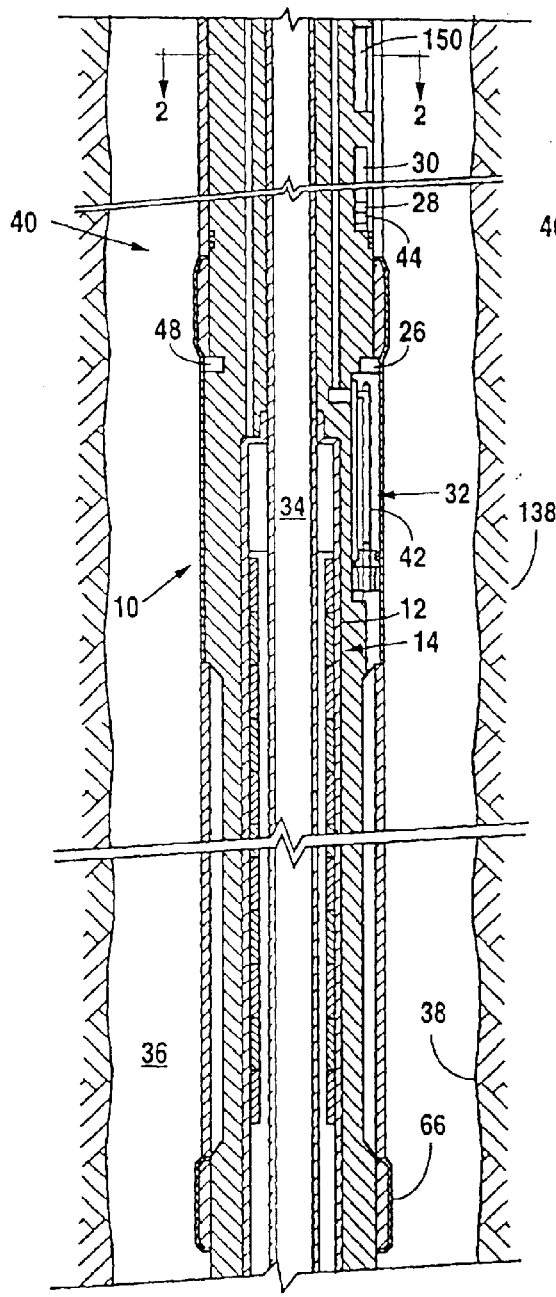
FIGS. 29 through 32 are schematic axial cross-sectional views of an apparatus constituting an alternative advantageous embodiment of this invention.
Figure 30:
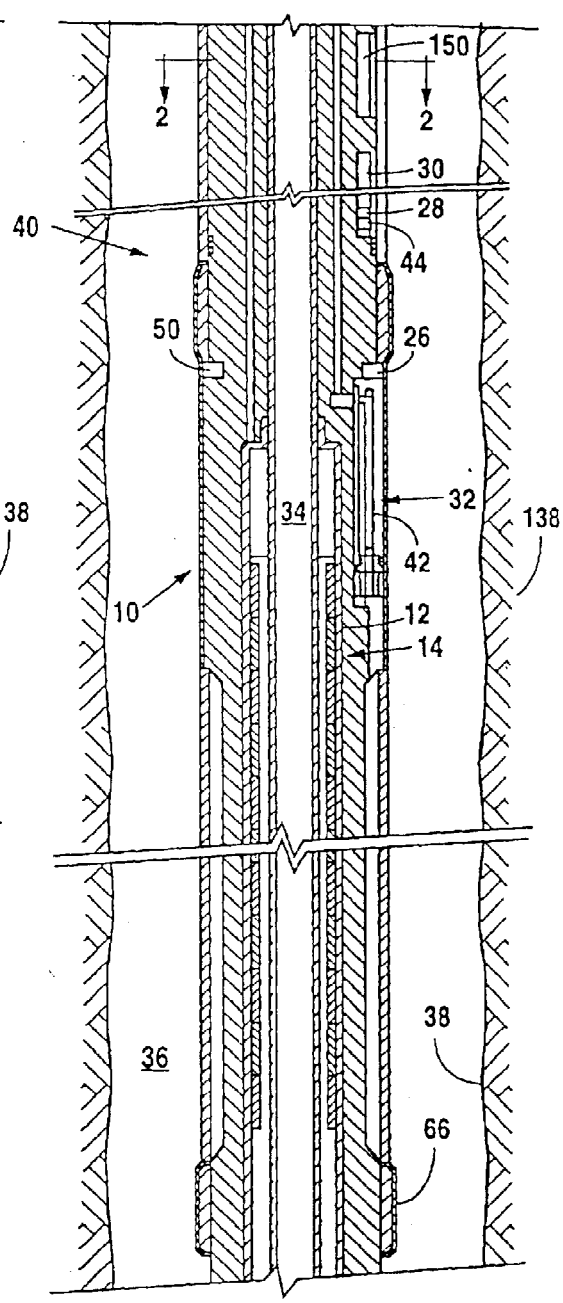
Figure 31:
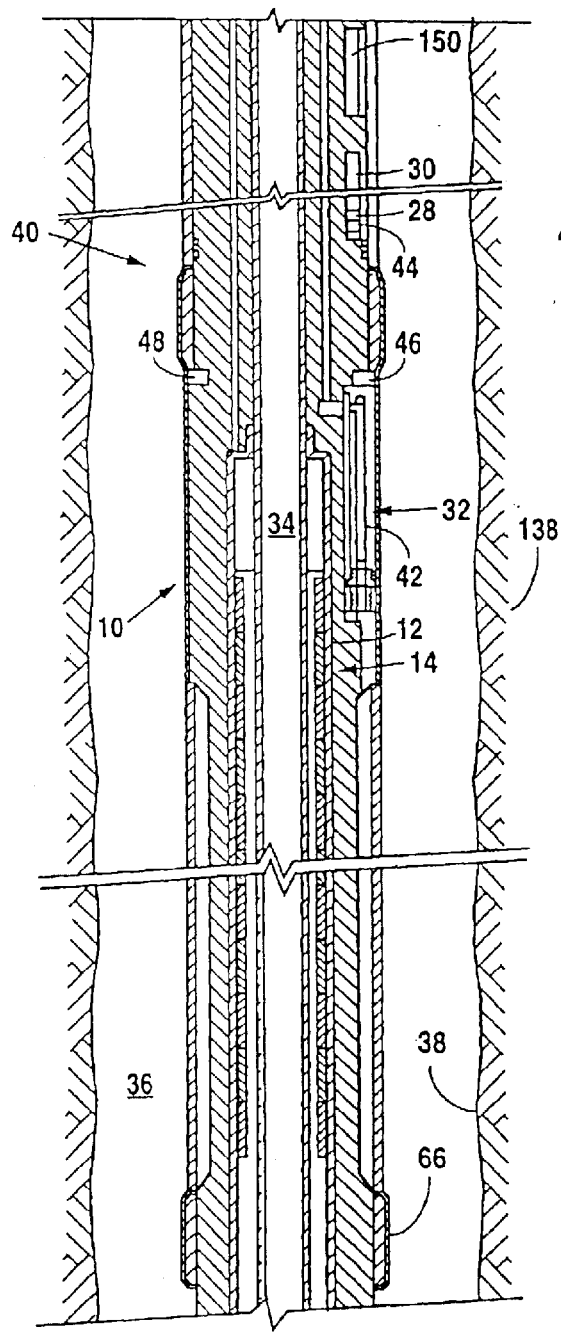

As shown in FIGS. 25, 26, 27, 28A and 28B (in which main armature 88, carriage 114, bearing 120, and drive shaft 86 are not shown for clarity), magnets 82 and 84 comprise a plurality of longitudinal permanent magnet segments, which are preferably bonded to carriage 114. The magnetization of the magnet segments alternates circumferentially from north pointing radially outward to north pointing radially inward. When magnets 82 and 84 are completely aligned as shown in FIG. 28A, the maximum electrical output will be generated. Conversely, when magnets 82 and 84 are completely misaligned as shown in FIG. 28B, zero electrical output will be generated. For the preferred embodiment shown, this range of movement is 45° (angle θ in FIG. 26). Thus, the requisite amount of electrical output is achieved by positioning magnets 82 and 84 between these two extremes. As shown in FIGS. 24, 26 and 27, a preferred embodiment limits this range of motion to the appropriate degree by means of a stop pin 104 that rotates within a transverse cavity in the form of a pair of symmetric sectors 86B within an enlarged portion 86A of drive shaft 86. A biasing element 100, preferably of hexagonal cross-section, is installed through an axial cavity 86C in one end of drive shaft 86 and into a matching, preferably hexagonal, shaped hole in stop pin 104. Biasing element 100 serves to bias carriage 114 and movable magnet 84 in the maximum-output position with stop pin 104 against one extreme of sectors 86B. This biasing effect is accomplished by applying a torsional preload on biasing element 100 in the direction of the rotation of drive shaft 86 and securing biasing element 100 in the preloaded position with a set screw 116 contained in an end fitting 118. Stop pin 104 protrudes through a hole in carriage 114 and thereby rotates with carriage 114 when carriage 114 is rotated by a drag torque, as discussed below, After carriage 114 has been rotated from its initial position with respect to drive shaft 86 by means of a drag torque as discussed below, stop pin 104 serves to return carriage 114 to its initial position by means of biasing element 100.

Persons skilled in the art will recognize that the hexagonal shape of biasing element 100 and the corresponding hole in stop pin 104 are simply a convenient means of fastening biasing element 100 to stop pin 104 using a segment of a conventional hex key (Allen wrench). In general, the shape need not be hexagonal so long as another means of fastening biasing element 100 to stop pin 104 is provided. Furthermore, the means of biasing carriage 114 and movable magnet 84 toward a certain position could take a variety of other forms, such as a coil spring. Moreover, the biasing mechanism could be located outside rather than inside drive shaft 86 if, for instance, electrical wires need to be routed through the inside of drive shaft 86. Also, although a preferred embodiment comprises a biasing mechanism, a biasing mechanism is not absolutely necessary for all applications and could be eliminated, if desired.

Persons skilled in the art will also recognize that the configuration of magnets 82 and 84 and the relative rotation limiting device for varying the amount of electrical output generated by an embodiment of this invention may take a variety of other forms. For example, the relative rotation may be limited to less than that which would be required to achieve complete misalignment of magnets 82 and 84 such that the maximum allowable rotation produces a certain fraction of maximum output instead of zero output. Alternatively, magnets 82 and 84 may be made of unequal axial length such that rotation into the completely misaligned position produces a certain fraction of maximum output instead of zero output. Additionally, the number of magnet segments comprising magnets 82 and 84 may be varied such that a rotation angle other than 45° is required to achieve complete misalignment. As shown in FIG. 25, the cross-sections of magnets 82 and 84 preferably have a circular outer shape and a polygonal inner shape. A circular outer shape is preferable for providing an optimal magnetic field to cooperate with main armature 88, and a polygonal inner shape is preferable for ease of manufacture and to help prevent the magnet segments from de-bonding from carriage 114 due to torsional loads. However, the outer and inner shapes of magnets 82 and 84 may comprise other suitable shapes, as will be readily recognized by persons skilled in the art. Because magnets 82 and 84 may be of polygonal cross-section or circular cross-section, the term "circumferential" as used herein to describe magnets 82 and 84 should be understood to mean the peripheral dimension of those elements, whether flat or curved. Also, although the magnet segments comprising magnets 82 and 84 are preferably of equal circumferential dimensions, they may be of unequal circumferential dimensions, if desired.

Further, the regulator for varying the position of movable magnet 84 with respect to fixed magnet 82 may take a variety of forms. Referring to FIG. 24, a preferred regulator comprises a drag element 98 mounted to a bearing 102 on drive shaft 86. Drag element 98, which rotates inside a fixed drag armature 90, is preferably made of copper and serves as a path for developing an eddy current. It should be understood that copper is referred to as a preferred material for certain elements of this invention, but any suitable conductive material could be used in place of copper for such elements. In typical downhole operations, fluctuations in parameters such as input RPM, electrical demands of system 140, and ambient temperature tend to cause fluctuations in the electrical output from main armature 88. Therefore, a preferred regulator includes a controller 106 which contains suitable electronics for monitoring the electrical output from main armature 88 and making appropriate adjustments to the input to drag armature 90, as discussed below, to modify the electrical output from main armature 88 and thereby meet the electrical requirements of system 140. Specifically, controller 106 generates an appropriate electrical control current in the windings of drag armature 90, which sets up a first magnetic field. The rotation of drag element 98 within the first magnetic field creates an eddy current in drag element 98, which is a function of (1) the magnetic field created by drag armature 90, (2) the speed of rotation of drag element 98, (3) the conductivity of drag element 98, and (4) the axial length of drag element 98. In turn, the eddy current in drag element 98 produces a second magnetic field that opposes the first magnetic field, which creates a drag torque on drag element 98. Thus, drag element 98 (rotor) and drag armature 90 (stator) function as a drag torque generator. The drag torque causes drag element 98 to rotate relative to drive shaft 86 in the direction opposite that of the drive shaft rotation. Because drag element 98 is connected to movable magnet 84 through a torque converter as discussed below, the drag torque rotates movable magnet 84 relative to fixed magnet 82 by an appropriate amount according to the applied electrical control current. The relative movement of movable magnet 84 with respect to fixed magnet 82 modifies the electrical output from main armature 88. Thus, as controller 106 senses deviations in the output from main armature 88, controller 106 makes appropriate modifications to the electrical control current in drag armature 90 to cause appropriate modifications to the output from main armature 88 and thereby meet the electrical requirements of system 140.

Persons reasonably skilled in the art will recognize that the required drag torque may be generated by a variety of other rotor/stator configurations, such as: (1) a copper drag element rotating inside permanent magnets housed in a fixed armature; (2) permanent magnets rotating inside a fixed copper cylinder; (3) a copper drag element rotating inside a motor-driven, rotatable drag armature comprising a series of alternately magnetized permanent magnet segments, similar to magnets 82 and 84 as shown in FIG. 25, which can be rotated in either direction to advance or retard the drag element, as appropriate; or (4) a drag element, comprising a series of alternately magnetized permanent magnet segments similar to magnets 82 and 84 as shown in FIG. 25, rotating within a stator comprising windings which can be energized to control the speed and direction of a rotating magnetic field and thus advance or retard the drag element, as appropriate. The foregoing options (1) and (2) would not include a controller 106 and therefore would not be responsive to the output from main armature 88; rather, those two open-loop options would be responsive only to changes in drive shaft speed and would simply limit the output from main armature 88. By contrast, the latter two options (3) and (4) would provide an additional advantage of helping to reduce the time that the apparatus takes to return to the initial, maximum-output position by enabling the application of a "reverse" drag torque (i.e., a torque in the same direction as the rotation of drive shaft 86) to drag element 98, thereby assisting biasing element 100 in moving carriage 114 and movable magnet 84 back to their initial position. If desired, option (1) or (2) could be used in conjunction with the other drag torque generator configurations described herein to provide both a rudimentary limit to the output and a more sophisticated output control mechanism. The rudimentary limit provided by option (1) or (2) in such a hybrid configuration may be desirable, for example, to prevent an electrical overload in the event of failure of the electronics in controller 106. Of course, the drag torque could also be supplied by a mechanical brake.

To achieve the desired movement of carriage 114 with as small a drag torque as possible, the drag torque generated on drag element 98 is preferably multiplied using a torque converter as it is transmitted to carriage 114. In a preferred embodiment, the torque converter comprises a harmonic drive mechanism such as those sold by Harmonic Drive Technologies, Inc. and HD Systems, Inc. Alternatively, the torque converter could comprise other known gear mechanisms, such as a planetary gear mechanism. Although it may be possible to eliminate the torque converter in certain embodiments of this invention, the absence of a torque converter would increase the input torque requirements to unacceptable levels in most instances.

As shown in FIG. 24, a preferred harmonic drive mechanism comprises a wave generator 92, a flexspline 94, and a circular spline 96. Drag element 98 is fixedly connected to wave generator 92, and circular spline 96 is fixedly connected to carriage 114 which comprises movable magnet 84. Circular spline 96 is relatively stiff and has internal teeth to engage flexspline 94. Flexspline 94, which is of slightly smaller diameter than circular spline 96 and has fewer teeth (usually two fewer) than circular spline 96, is relatively flexible and has external teeth to engage circular spline 96. Wave generator 92 comprises an elliptical, thin raced ball bearing that fits inside flexspline 94 and causes flexspline 94 to engage circular spline 96 at each end of the major axis of the ellipse. Wave generator 92, flexspline 94, and circular spline 96 cooperate such that each revolution of wave generator 92 causes circular spline 96 to rotate by only two teeth, for example. Thus, the drag torque on drag element 98 is multiplied as transmitted to carriage 114 and movable magnet 84 as a control torque. A tradeoff for achieving this torque multiplication is that the harmonic drive mechanism increases the response time of the apparatus. However, if desired, the use of a motor-driven, rotatable drag armature as mentioned above would help to decrease the response time.

Because power generator 80 comprises a brushless, non-contact apparatus, it has an additional advantage of being capable of operating while immersed in oil. Thus, if oil is needed for pressure balancing due to high downhole pressures, this generator can safely operate in an oil-filled compartment.

Persons skilled in the art will recognize that other advantageous configurations are possible to vary the amount of electrical output generated by an embodiment of this invention. For example, an advantageous configuration may be to fix the initial relationship of magnets 82 and 84 in a certain degree of misalignment such that the default electrical output is somewhat less than the maximum possible output. Indeed, it may be beneficial in certain applications to have an initial relationship of complete misalignment of magnets 82 and 84 such that the initial electrical output is zero. By selecting the proper arrangement of the harmonic drive output direction and the direction of the biasing torque, the drag torque could be made to increase or decrease the electrical output, as desired. However, in a preferred embodiment of this invention, controller 106 is powered by a portion of the output from main armature 88. Therefore, an initial relationship of complete misalignment of magnets 82 and 84 which produces zero initial output generally would not be desirable unless an alternate power source is provided for controller 106.

Still another advantageous configuration may be to have a threaded cooperation of movable magnet 84 on drive shaft 86 such that the drag torque created on drag element 98 translates movable magnet 84 axially and thereby changes the electrical output by changing the percentage of movable magnet 84 that is encompassed by main armature 88. Such a threaded configuration would also vary the electrical output by changing the separation distance between fixed magnet 82 and movable magnet 84.

Because the present invention is intended to be able to operate at elevated downhole temperatures, the various magnets referred to herein preferably comprise samarium-cobalt (Sm—Co) magnets. Although some other types of magnets, such as neodymium-iron-boron (Nd—Fe—B) magnets, generally provide better magnetic flux at lower temperatures, Sm—Co magnets maintain better energy density at temperatures above about 150° C. However, any suitable type of magnets may be used, if desired.

(8) Electronics

Figure 33:
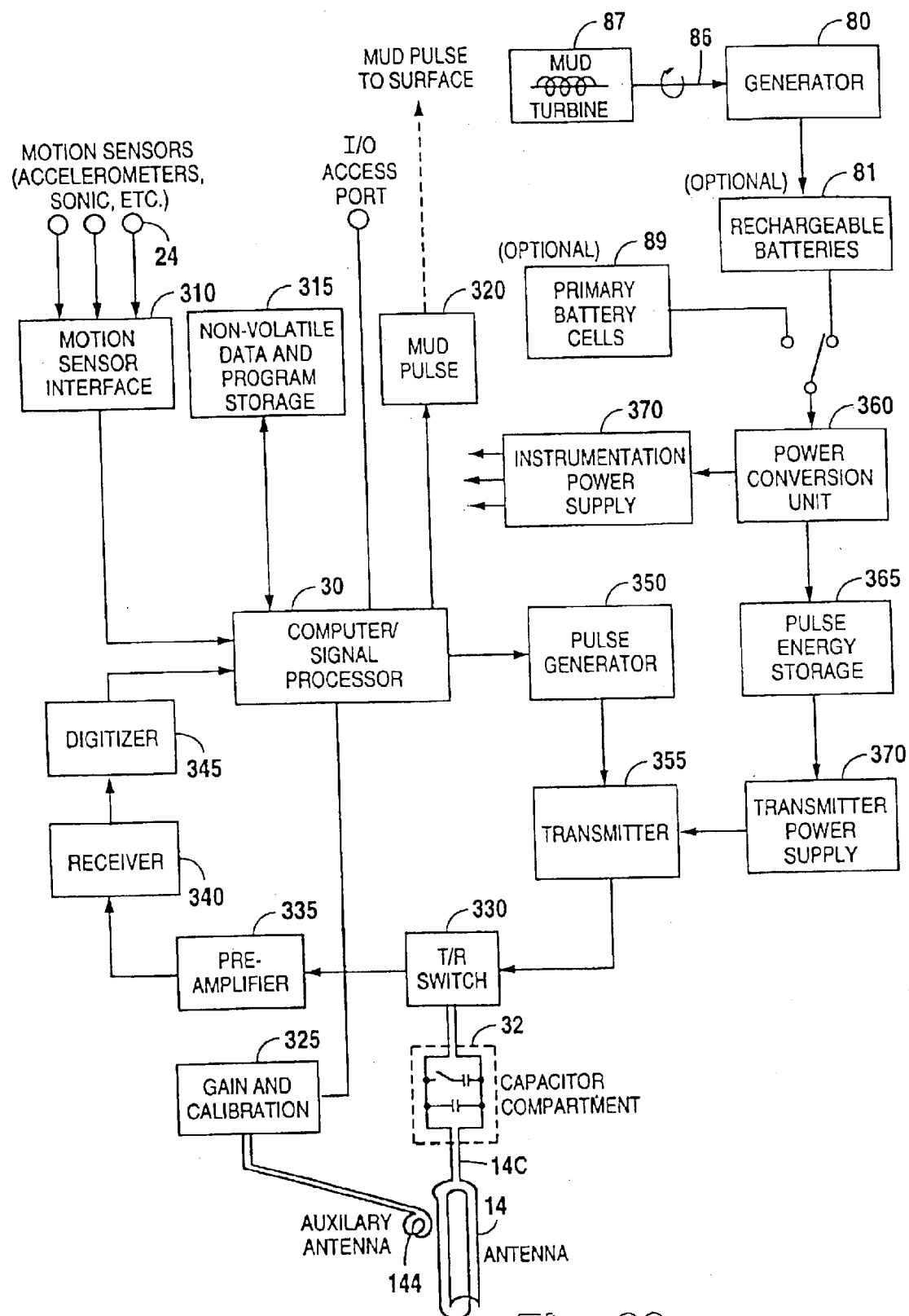
FIG. 33 is a block diagram of the tool electronics.
Figure 34:
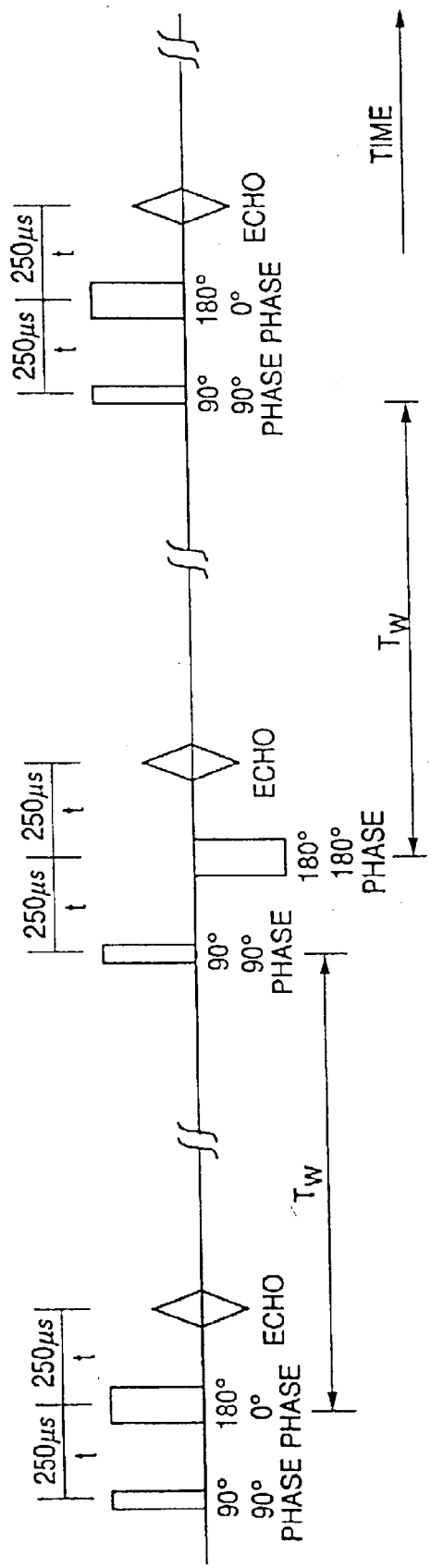
FIG. 34 is a timing diagram for a single-echo CPMG sequence incorporating phase alternation.

Referring next to FIG. 33, it illustrates in a block-diagram form the preferred electronics arrangement for the tool of the present invention. In particular, the resonant circuit comprised of antenna 14 and the tuning capacitors 32 is interfaced to a transmit/receive switch 330. This T/R switch receives pulsed RF power from the transmitter 355, which is gated by the pulse generator 350. The pulse generator is under control of the computer/signal processor 30. The T/R switch 330 routes the received signal to a preamplifier 335, which in turn drives the receiver section 340. The received, amplified signal is digitized in digitizer 345 and fed into the processor 30.

In a preferred embodiment, processor 30 receives real-time motion data from the motion sensor interface 310, which conditions the electrical signal from motion sensors 24. The operation of the motion sensors is described in frther detail below. Additionally, the processor reads from and writes to a non-volatile data and program memory 315. In a preferred embodiment, this memory retains data even when the electronics is not supplied with electrical power. In a preferred implementation, the non-volatile memory uses "Flash" EEPROM integrated circuits. Another suitable option is a battery-powered low-power CMOS static RAM. The memory 315 holds all data acquired during a run. Processor 30 performs real-time processing on the data to extract an indication of formation porosity and of log quality. In a preferred embodiment, this data is converted into a data stream of preferably very low bit rate and are fed into a mud-pulse system 320 that broadcasts the data stream to the surface by means of pressure pulses within the fluid column within the drill collar. Above-surface processing equipment (not shown) can be used to display the results to an operator. It will be appreciated that different tool-to-surface communication approaches are possible in alternative embodiments. Further, those skilled in the art will appreciate that downhole processor 30 may be implemented using two or more dedicated signal processors communicating with each other. In this embodiment, each processor can be performing a different task. For example, with reference to the following section on motion detection, a dedicated processor can be used to monitor signals related to the motion of the tool in the borehole and to provide signals for defining appropriate time windows when NMR signals from the formation are to be processed by a separate signal processor. It is applicants' intention that any suitable processor configuration can be used in accordance with the principles of the present invention. Further, it should be apparent that various options that exist for storage and communication of the acquired information to the user can be used without departing from the spirit of this invention.

The electrical power required to operate the tool was described in some detail in the preceding section. FIG. 33 illustrates the power generation in a block diagram form. In particular, as shown this power is derived in accordance with the present invention from one or more of the following sources: (a) an (optional) bank of primary battery cells 89, typically of the lithium type, or (b) from a turbine/generator combination 80-87 that converts a portion of the mechanical energy delivered by the flowing mud column into electrical energy. The generator can be used to directly drive the power conversion unit 360. A potential disadvantage of this arrangement is that the tool cannot operate without mud being continuously pumped from the surface through the drill collar through the NMR tool to the drill bit. This requirement could potentially interfere with the requirements of the drilling operation. Therefore, in a preferred embodiment, the turbine/generator combination is used to charge a bank of rechargeable secondary battery cells 81, for example of the nickel-cadmium or silver-oxygen type. In a preferred embodiment, the generator 80 is sufficiently powerful to recharge the secondary elements in a short amount of time, while these secondary cells supply electric power to the tool during the time when no or very slow mud flow exists.

The power conversion unit 360 converts the energy from primary or secondary cells into a form suitable for short-term storage in high-voltage capacitors 365. These capacitors feed the transmitter power supply 370 and are capable of discharging within fractions of milliseconds as required to generate high-power RF pulses of short durations.

(9) Auxiliary Antennas and Their Functions

Figure 32:
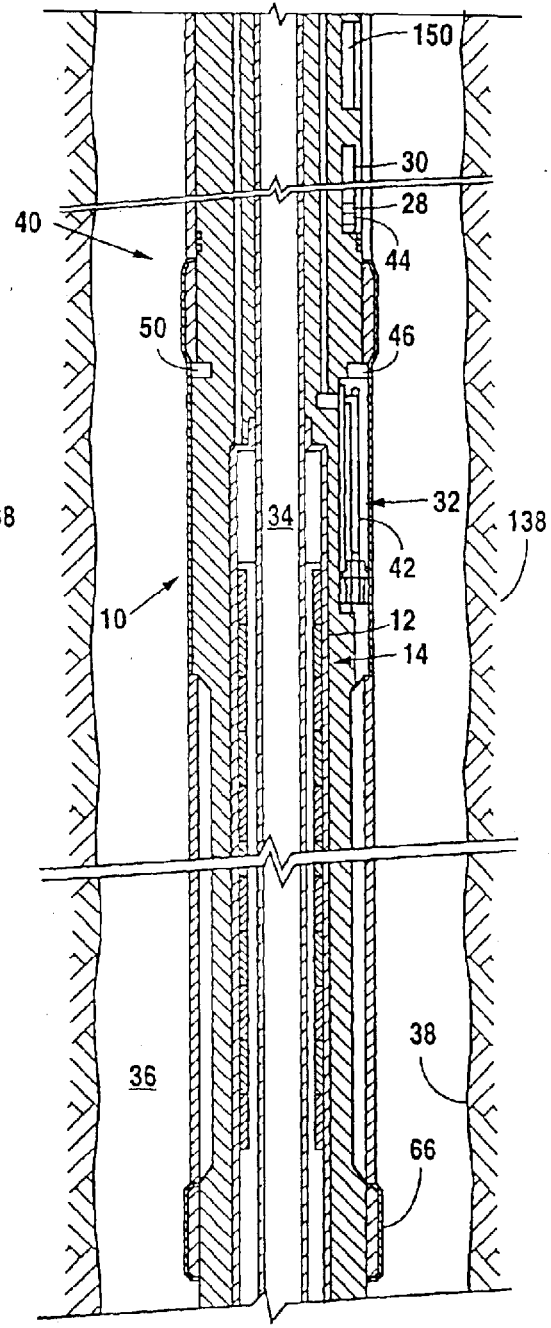

Another important aspect of the present invention is the use of one or more auxiliary coils 144 as shown in FIG. 33 and FIG. 5. These coils are mounted in one or more recesses within the aperture of the main antenna 14, where a small amount of the RF flux from the main antenna is sampled by the auxiliary coil(s) 144. Coil(s) 144 act as small antennas and are interfaced to a calibration circuit 325 (FIG. 32), which is under control of processor 30. The purpose of coil(s) 144 is three-fold: Firstly, during transmission of RF pulses, coil 144 picks up a fraction of the RF magnetic flux and generates a proportional voltage. This voltage is amplified by the electronics and generates an indicator signal for the strength of the outgoing RF pulse. This information is fed back into the driver electronics for the RF pulse generation to increase or to decrease the delivered RF pulse power. Thus, in accordance with the present invention a constant RF pulse amplitude is achieved that is independent of variable load conditions due to changes in borehole size, changes in the conductivity of borehole fluids and/or changes in conductivity of the formation.

In accordance with the present invention the auxiliary antennas 144 have another purpose: Before an NMR pulse sequence is started, a reference signal of known amplitude is injected into the system by means of coil(s) 144. The resultant magnetic flux is picked up by the antenna 14, amplified and processed by the signal processor. This reference signal acts in a preferred embodiment as built-in secondary calibration. In particular, by comparing the signal amplitudes received during the CPMG sequence to the apparent signal strength of the reference signal, it is possible to derive signal amplitudes which are independent of the system gain factor and of the Q factor of the resonant circuit formed by the antenna and the resonant capacitor(s). The reference signal is typically transmitted once per second through coil(s) 144.

Furthermore, a potentially dangerous condition can be detected by monitoring the apparent strength of the reference signal generated by the auxiliary antennas. Specifically, a low reference signal is typically caused by excessive loading of the antenna 14, for instance by the presence of metallic pipe lining the borehole walls and surrounding the NMR tool. Transmitting an RF pulse in such a situation could potentially damage the RF transmitter by reflecting the outgoing energy back into the tool. Therefore, in accordance with a preferred embodiment, a timing circuit is triggered when an excessive load condition exists and disables the transmitter for about 15 more minutes after the load condition is removed. This is a fail-safe mechanism used in a preferred embodiment to make sure that the tool is never in the vicinity of casing when the transmitter is turned on.

The fail-safe mechanism described above is also used in accordance with the present invention to make sure that the tool never transmits RF energy while in free air on the surface. Such a transmission may be disruptive and potentially hazardous for nearby electronic circuits. Accordingly, a protective, conductive blanket is provided, that the operator wraps around the tool whenever the tool is on the surface. The tool detects this condition once every second and goes into fail-safe mode with the transmitter turned off. After the conductive blanket is removed, in a specific embodiment the operator has about 15 minutes to deploy the tool into the borehole. Typically, the borehole near the surface is cased, which keeps the RF transmitter turned off as long as the tool resides within the cased portion of the borehole.

Finally, the periodic signal radiated by auxiliary antenna(s) 144 provides in accordance with the present invention a convenient means for verifying the operation of processor 30 without having to make electrical contact with the tool.

(B) NMR Measurement Methods Using Motion Management

NMR measurement methods are generally known and are described in a variety of prior art references including, for example, U.S. Pat. Nos. 4,710,713; 5,212,447; 5,280,243; 5,309,098; 5,412,320; 5,517,115, 5,557,200 and 5,696,448 to the assignee of the present invention. These patents are incorporated herein by reference for all purposes. The following discussion therefore focuses on aspects of the NMR measurement methods relevant in the context of the present invention.

The preferred method for the NMR measurement in accordance with the present invention is to use the Carr-Purcell-Meiboom-Gill pulse sequence (CPMG) as shown in FIGS. 33(a) and 33(b). The first pulse in the sequence (90°-pulse, with 90° phase) is typically 50 $\mu$sec long, all subsequent pulses (180°-pulses, with 0° phase) are typically 100 $\mu$sec long. The timing is such that the center-to-center delay between the first and the second pulse ($\tau$) is 250 $\mu$sec and all other pulses are 500 $\mu$sec center-to-center apart. With such a pulse timing, NMR echoes can be detected between all consecutive 180° pulses.

After each CPMG pulse sequence, a wait time $T_W$ of several seconds is necessary in order to allow the hydrogen to re-polarize to an equilibrium condition. Therefore, although the actual pulse sequence may last only for milliseconds, each measurement takes several seconds, once the wait time is taken into account. It is therefore advantageous to issue a CPMG sequence only during time windows when lateral tool motion is slow to improve the chances for a valid NMR measurement and not to waste valuable measurement time. Since the exact delay between CPMG pulse sequences is not critical, is it possible, to extend, if necessary, the minimum required delay $T_W$ by additional time in order to start a new measurement in a favorable time window.

Conversely, the thin shell of the sensitive volume 36 (FIG. 6A), suggests that moderate lateral tool motion can be helpful by automatically selecting a new sensitive volume within a small delay after a CPMG measurement. By monitoring the lateral tool motion, the tool can determine when such a condition exists and can speed up the measurement cycle by shortening the wait time $T_W$.

(1) Signal Processing Using Phase-Alternated Pairs

In accordance with the present invention the echo responses acquired within a CPMG sequence are preferably digitized and recorded in two channels: in-phase and in-quadrature. In a first processing step, data from consecutive CPMG sequences are added echo-by-echo and channel-by-channel to form a phase-alternated pair (PAP). The first data half of a PAP comes from a CPMG sequence as shown in FIG. 33(a), the second half is supplied by a CPMG sequence as shown in FIG. 33(b). The difference between the sequences shown in FIGS. 33(a) and 33(b) is that in the latter the phases of all 180° pulses have been inverted. The net effect of using PAP in accordance with the present invention is that artifacts, which tend to be coherent with the phases of the 180° pulses, tend to cancel out, while the NMR signal, whose phase is tied to the initial 90° pulse, is amplified. For those skilled in the art it should be obvious that the same effect can be achieved by inverting the phase of the 90° pulse from 90° to 270°, accompanied by subtracting—instead of adding—the resultant echo streams.

In order to achieve the beneficial effect of PAP accumulation, both parts of a PAP must be valid NMR measurements. An important part of the present invention is that information about the tool motion is incorporated into the NMR sequencing. Thus, in a specific embodiment, if during any CPMG sequence the lateral motion exceeded the allowable limits, the resultant data set is discarded and the computer/signal processor 30 attempts to re-acquire a valid data set. To this end, the computer delays by the appropriate wait time $T_W$ and repeats the previous CPMG sequence. In accordance with this embodiment, only when the data has been validated the sequence proceeds to the next measurement.

To describe motion management as used in the present invention in the proper context, it should be noted that it is well known in the art that the amplitude of the first echo is fairly good approximation of the number of hydrogen atoms in the fluid state and therefore can be calibrated to read fluid-filled porosity. Therefore, in accordance with a first embodiment of this invention, the simplest possible CPMG measurement consists of only one 90° pulse, one 180° pulse and one signal acquisition. The total time from the first pulse to the end of the signal acquisition in this case is about 0.5 msec. It has been demonstrated by numerical modeling and by experiments that a lateral displacement of about 0.1 mm is allowable within this time period without causing an undesired change in echo amplitude. This translates into a maximum limit for transversal velocity of 0.2 m/sec.

Figure 35A:
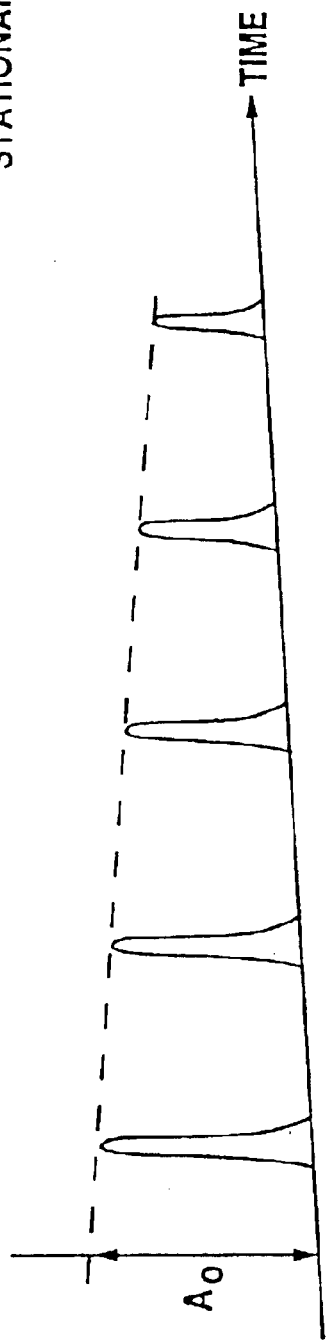
FIG. 35 is a schematical sketch of the echo amplitudes obtained from a phase-alternated pair, in a stationary tool (a), and during lateral motion (b).
Figure 35B:
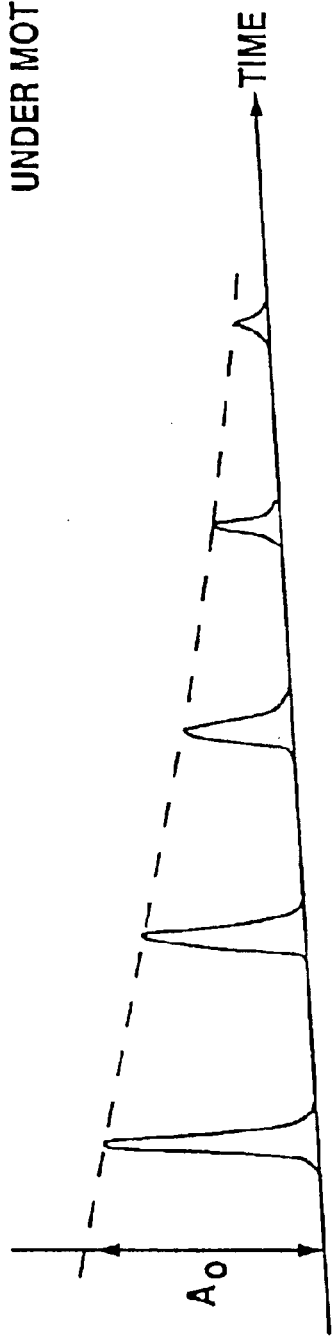

Alternatively, the CPMG pulse sequence may be continued with more 180° pulses and data acquisitions. Subsequent echoes may become more and more depressed because the sensitive volume shifts laterally through the formation. However, as shown in FIGS. 35a and 35b, even in this case an approximation of the initial echo amplitude can be recovered. FIG. 35a shows typical echo amplitudes without motion present. The peaks of the echoes are curve-fitted and extrapolated back to the time of the initial 90° pulse, as known in the art. The resultant amplitude $A_o$ is a direct measure of formation porosity. With tool motion present, the echo amplitudes become more and more depressed as shown in FIG. 35b, and curve-fitting and back-extrapolation yields a possibly different approximate value for the initial amplitude $A_o$. The following description illustrates approaches to motion management used in accordance with the present invention to correct NMR measurement signals obtained from moving tools.

(2) Motion Management

Referring back to FIG. 1, in a specific embodiment, the motion management aspect of this invention comprises accelerometers 24 along with a signal processor 30 for processing the accelerometer signals and the NMR signals from the formation, and a conventional data transmitter 150 to transmit the data to the surface. In certain embodiments, an additional high-pass filter 44 can also be used. Alternatively, another advantageous embodiment shown in FIG. 29 comprises acoustic sensors 26 and an inclinometer 48. Yet another embodiment of the motion management used in accordance with the present invention, shown in FIG. 30, comprises acoustic sensors 26 and a magnetometer 50. Another advantageous embodiment shown in FIG. 31 comprises contact sensors 46 and an inclinometer 48. Still another advantageous embodiment shown in FIG. 32 comprises contact sensors 46 and a magnetometer 50. In the embodiments of FIGS. 29 through 32, the signal processor 30 is for processing, in addition to the NMR signals from the formation, the acoustic sensor, contact sensor, inclinometer, and magnetometer signals, as the case may be. The various embodiments having accelerometers, acoustic sensors, contact sensors, inclinometer, and/or a magnetometer can be used in accordance with the present invention to manage the lateral motion of the tool 40 in the borehole 36, i.e., to account for it as part of the signal processing algorithm.

Tool Motion Regimes

In the preferred embodiment, the type of NMR measurement performed is adapted to the tool motion regime in an automatic fashion. The following motion regimes can be identified and correspond to particular NMR measurements:

1. Stationary tool. If no lateral motion is detected, the tool can replicate NMR measurements similar to wireline operation. Because the measurement volume does not substantially change during the course of a few 100 milliseconds, the CPMG sequence is extended to include typically 501 pulses and 500 echoes. The wait time between experiments is chosen to allow the same sensitive volume to re-polarize between CPMG sequences and is on the order of 5 seconds.
2. Normal drilling mode. Some lateral motion is present, but the speed does not exceed 0.2 m/s. This means that at least the first echo is always valid and possibly more echoes, depending on the instantaneous velocity. In this motion regime, in a preferred embodiment the tool selects a shortened CPMG sequence of typically 51 pulses and 50 echoes. The wait time is shortened by about a factor of one-half to 2.5 seconds. Data taken during an interval where the velocity exceeds 0.2 m/s are discarded and the sequencer attempts to re-acquire the same data. All data are time-stamped and stored in non-volatile memory, together with motion data immediately acquired before and after the NMR measurement. The echo amplitudes are curve-fitted as shown in FIG. 35, and the obtained amplitude $A_o$ is converted into porosity units and reported in real-time to the surface by means of the mud-pulse system.
3. Whirling mode. In this mode, the lateral velocities are typically outside acceptable limits. In a specific embodiment the tool selects the shortest possible CPMG sequence consisting of only two pulses and a single echo. The processor waits for the motion detection to identify a moment when the instantaneous speed is below 0.15 m/s and attempts an NMR measurement that lasts 0.5 msec. Immediately after the NMR data acquisition, the instantaneous velocity is checked again. If it does not exceed 0.2 m/s, the NMR data point is accepted, otherwise rejected. The minimum delay between measurements is about 2.5 sec, but the actual delay can be highly variable, depending on the frequency of motion windows.
4. Stick/slip mode. In this mode, certain time windows exist in which the tool is almost stationary. The tool monitors the motion data to determine whether or not these windows are longer than a 50-echo CPMG sequence. If not, the tool falls back to the single-echo of a whirling condition (3). If yes, the CPMG sequence compatible with normal drilling is selected (50 echoes). The tool triggers the CPMG measurement at the onset of a "sticking" condition, but no sooner than about 2.5 seconds after the last measurement. Motion data taken during and after the CPMG sequence is recorded to determine if the window was wide enough to validate all 50 echoes.

In accordance with the present invention the tool is programmable before being deployed in the borehole. The operator can choose which of the operating modes (1)–(4) can be selected during run time. Also, certain modes may be forced, bypassing the downhole decision logic.

FIG. 9 is a block-diagram of the motion management algorithm used in accordance with the present invention. The algorithm starts at 200 and proceeds to measure the tool's lateral acceleration and rotation speed (RPM) at 205. If in decision block 210 the RPM measurement indicates stick-slip motion (235), the next step 240 is to forecast the stick phase and then calculate the average and maximum lateral velocities in block 245. Next the computed quantities are compared at 250 to some predetermined constants. In particular, if average lateral velocity is less than or equal to $V_{a1}$ and the maximum lateral velocity is less than or equal to $V_{a2}$, then it is safe to process the NMR signals, and the algorithm proceeds to prepare NMR sampling at 260.

If the conditions in decision block 250 are not met, the velocities indicate that the tool is undergoing whirling motion possibly combined with stick-slip motion, and the whirling portion of the algorithm must be followed.

If the RPM measurement does not indicate stick-slip motion at 210, then the next step 215 is to calculate the average and maximum lateral velocities. If in decision block 220 the average lateral velocity is shown to be less than or equal to a predetermined value $V_{a1}$ and the maximum lateral velocity is also shown less than or equal to another value $V_{a2}$, then the velocities indicate normal drilling motion 225. In such case, it is safe to proceed with the NMR sampling in block 230. However, if the average lateral velocity is greater than $V_{a1}$ or the maximum lateral velocity is greater than $V_{a2}$, then the velocities indicate that the tool is undergoing whirling motion, indicated in block 265. In that case, further calculations are needed.

When the velocities indicate whirling motion, the next step 270 is to calculate the duration of time for which the lateral velocity is less than $V_{a2}$. If that duration is greater than or equal to a parameter $T_a$, then the next step 275 is to calculate the duration in which the lateral velocity is less than a parameter $V_{a1}$. If this second duration is greater than or equal to $T_a$, then the NMR measurement 280 should be made when the lateral velocity is less than or equal to $V_{a1}$ and the absolute value of the lateral acceleration is less than a pre-determined value. If this second duration is less than $T_a$, then the NMR measurement 285 should be made when the lateral velocity is less than or equal to $V_{a2}$ and the absolute value of the lateral acceleration is less than a pre-determined value. Similarly, if the duration of time for which the lateral velocity is less than $V_{a2}$ is also less than $T_a$, then the second duration calculation is not needed and the NMR measurement 285 should be made when the lateral velocity is less than or equal to $V_{a2}$ and the absolute value of the lateral acceleration is less than a pre-determined value.

In the preferred embodiment, the maximum motion criterion in the MWD mode is that the lateral velocity must be less than or equal to about 0.2 m/s. However, to be conservative, the criterion maybe set at 0.15 m/s to provide a 33% margin of safety. The variables used in the embodiment illustrated in FIG. 9 are thus as follows:

$V_{a1}$=0.10 m/s $V_{a2}$=0.15 m/s $T_a$=10 ms

In the sliding/wiping mode, the maximum motion criterion may be different due to different NMR sampling times, and the cut-off frequency for the high-pass filter 44 (see FIG. 1) may be different depending on the drill collar rotation speed.

Accelerometer-based Motion Management

Figure 7:
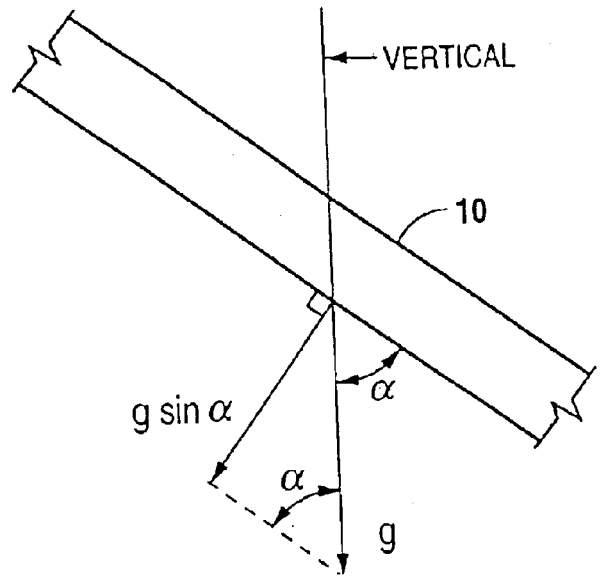
FIG. 7 is a schematic elevational view showing the gravitational acceleration of the apparatus of FIG. 1 when said apparatus is inclined with respect to the vertical.
Figure 8:
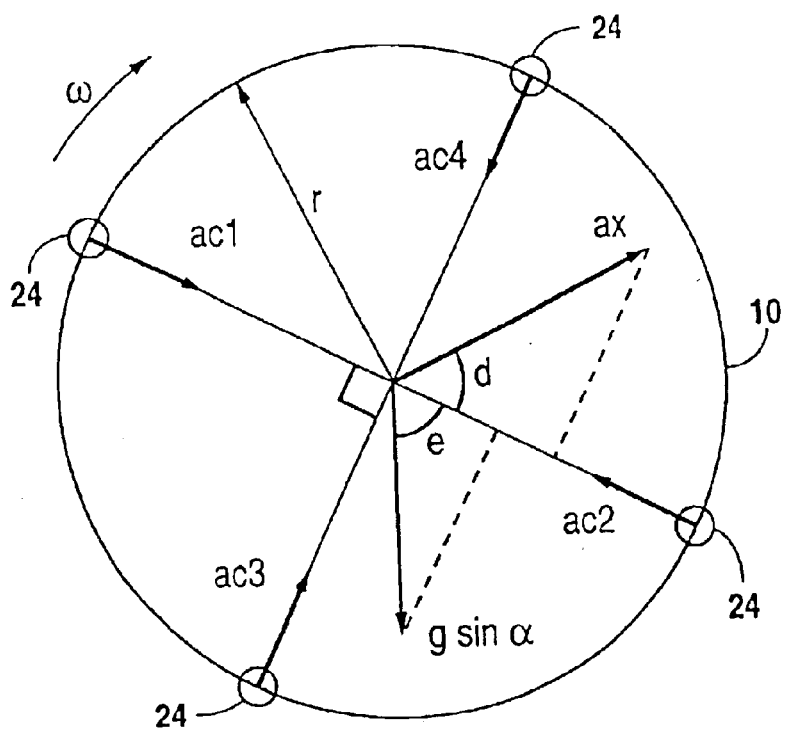
FIG. 8 is a schematic cross-sectional view showing a preferred embodiment for the arrangement of the accelerometers in the apparatus of FIG. 1.

In a preferred embodiment, four accelerometers 24 are placed around the circumference of the drill collar 10 as shown in FIG. 8. Accelerometers ac1 and ac2 are at opposite ends of one diameter, and accelerometers ac3 and ac4 are at opposite ends of a perpendicular diameter. The in-plane component of the gravitational acceleration g sin α, is oriented in the vertical plane, and the lateral acceleration vector is in some arbitrary direction. In typical applications, the drill collar rotates at angular velocity w, producing centripetal acceleration ac=rw². As discussed above, the motion of the drill collar 10 for an arbitrary inclined orientation (as shown in FIG. 7) is governed by Eqs. [5]. To eliminate the gravity terms in Eqs. [5], a high-pass filter 44 (see FIG. 1) may be used. The frequency cut-off for the high-pass filter is above that of the typical drill string rotation speeds. The governing equations then become simplified to those of Eqs: [1], so that the drill collar rotation speed S and the magnitude and direction of the lateral acceleration ax may be determined by Eqs. [2], [3], and [4].

Figure 39:
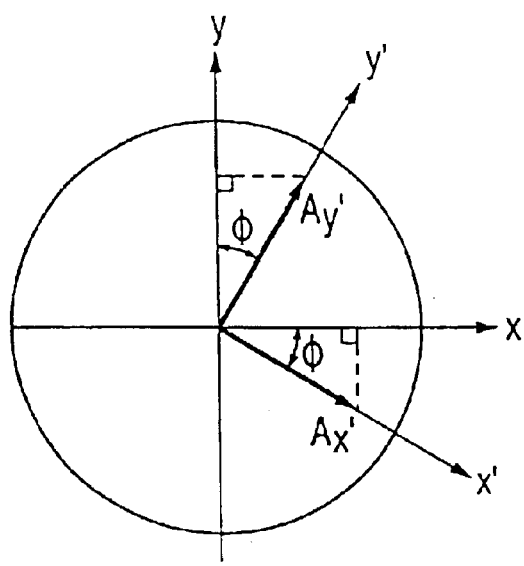
FIG. 39 is a schematic cross-sectional diagram showing a rotating coordinate system (x',y') and a fixed coordinate system (x,y) for the apparatus of FIG. 1.

Because the tool 40 is typically rotating, the initial measurement of the lateral acceleration ax is with respect to a rotating coordinate system (x',y'), as shown in FIG. 39. However, the velocity and displacement of the tool 40 are needed in the fixed reference frame of the borehole (earth). Thus, the lateral acceleration measurement must be converted to a fixed coordinate system (x,y) by way of a coordinate transformation. Referring to FIG. 39, the orthogonal components of the lateral acceleration ax in the rotating coordinate system are represented as $A_x'$ and $A_y'$. The rotating coordinate system is rotationally displaced from the fixed coordinate system by an angle φ. Therefore, the orthogonal components, $A_x$ and $A_y$, of the lateral acceleration ax in the fixed coordinate system are calculated as follows:

$A_x = A_x' \cos\phi + A_y' \sin\phi$     Eq. [7]

$A_y = -A_x' \sin\phi + A_y' \cos\phi$     Eq. [8]

The angle φ (in radians) is obtained from the following relation:

$\phi = \phi_o + \omega t$     Eq. [9]

where $\phi_o$ is the initial value of the angle φ, ω is the angular velocity (in radians/second) of the drill collar 10, and t is time (in seconds). Because the actual value of the initial condition, $\phi_o$, is not important for purposes of this invention, $\phi_o$ may be assumed to be zero.

After converting the lateral acceleration ax into the fixed reference frame, the signal processor 30 is then used to integrate the lateral acceleration ax once to obtain the tool's lateral velocity, and twice to obtain the tool's lateral displacement. The signal processor 30 then uses these parameters in conjunction with the motion management algorithm as shown in FIG. 9 to predict acceptable time windows in which to make NMR measurements. After NMR measurements are made, the signal processor 30 also verifies that they were made within acceptable levels of lateral motion.

Acoustic-Sensor-Based Motion Management

In the acoustic sensor versions of the apparatus (FIGS. 29 and 30), a plurality of at least two acoustic sensors 26 are placed around the perimeter of the drill collar 10. Similarly; in the contact sensor embodiments of the apparatus (FIGS. 31 and 32), a plurality of at least two contact sensors 46 are placed around the perimeter of the drill collar 10. Instead of measuring the tool's lateral acceleration, these embodiments measure the tool's lateral displacement by sensing the tool's distance from the borehole wall at a plurality of times. Then, the signal processor 30 differentiates the displacement measurements once to obtain the tool's lateral velocity, and twice to obtain the tool's lateral acceleration.

Figure 14:
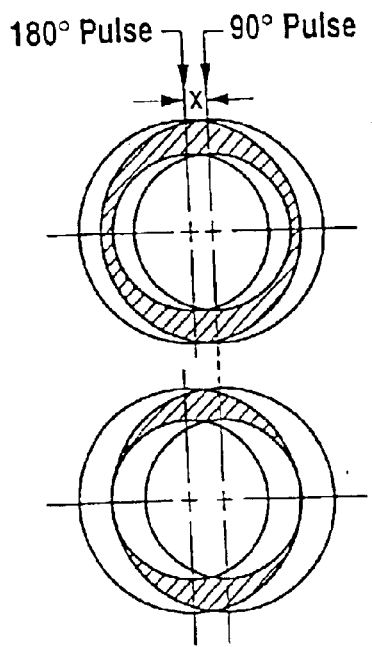
FIG. 14 shows various stages of the change in sensitive volume for the apparatus of the present invention, which are due to lateral motion.
Figure 17:
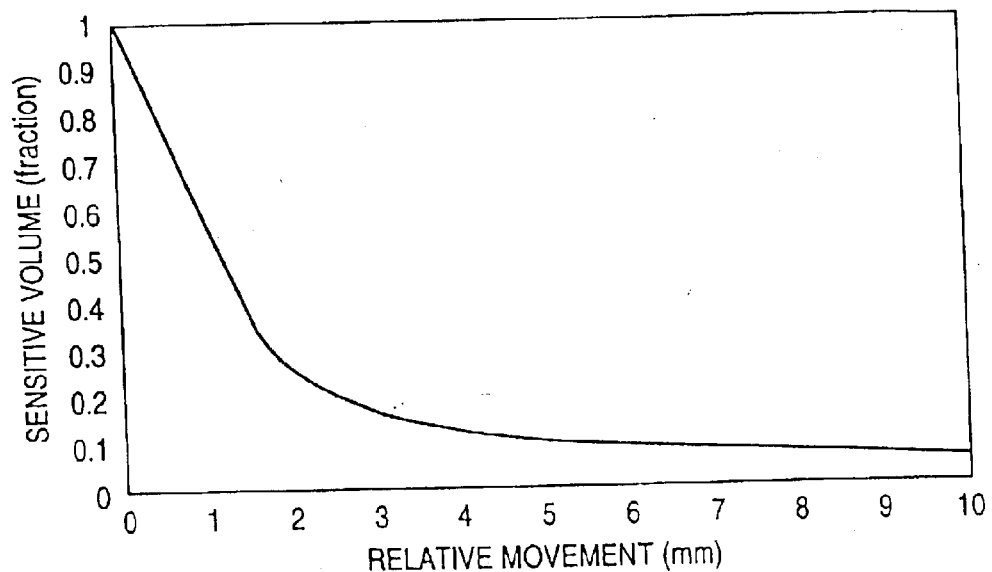
FIG. 17 shows a plot of the sensitive volume as a function of lateral displacement.

In the single-echo acquisition modes of whirling and stick/slip, the measurement can tolerate lateral velocities of up to about 0.5 m/s. Although up to 50% signal amplitude is lost at the upper limit of the range 0.2–0.5 m/s, this loss can be recovered by estimating the average lateral velocity during the NMR measurement (0.5 msec). In FIG. 14, the shaded area represents the portion (overlap) of the sensitive volume that is the same at the time of the 90° pulse and the first-echo signal acquisition window. The percentage that the shaded area bears to the original, full cross-sectional area of the sensitive volume is the same as the percentage that the received NMR signal amplitude bears to the NMR signal amplitude that would have been received if the tool had remained stationary. Thus, the plot of FIG. 17 shows the relationship between the fraction of the original sensitive volume at the time of the NMR echo and lateral tool movement between the 90° pulse and the NMR echo. The signal processor uses this relationship to apply the appropriate correction factor to the NMR signal.

Figure 15:
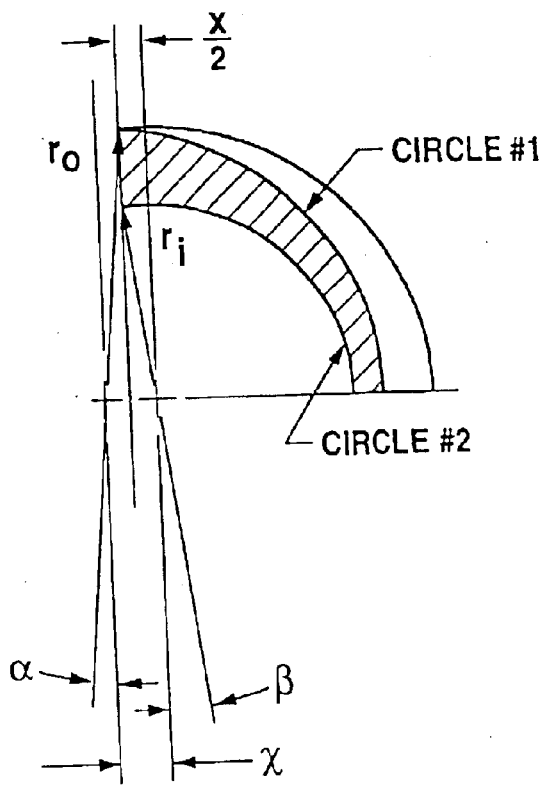
FIGS. 15 and 16 show how the change in sensitive volume may be calculated in accordance with a preferred embodiment of the present invention.

FIG. 15 shows how to calculate the area of the overlapping portions of the measurement volume of FIG. 14. Referring to FIG. 15, because radii $r_o$ and $r_i$ are much greater than the displacement x, the angles α and β are approximately equivalent. Therefore, for a single quadrant, the area enclosed by circle #1 is given by the relation $A_1 = (\frac{1}{4})(\pi r_o^2)[(\pi/2 - \alpha)/\pi/2]$     Eq. [10]

and the area enclosed by circle #2 is given by the relation $A_2 = (\frac{1}{4})(\pi r_i^2)[(90+\alpha)/90]$     Eq. [11]

The area of the triangle is given by the relation $A_t \approx (\frac{1}{2})(x)[(r_o + r_i)/2]$     Eq. [12]

Thus, the area $A_a$ of the hatched portion is given by the equation $A_a \approx A_1 - (A_2 + A_t)$     Eq. [13]

Figure 16:
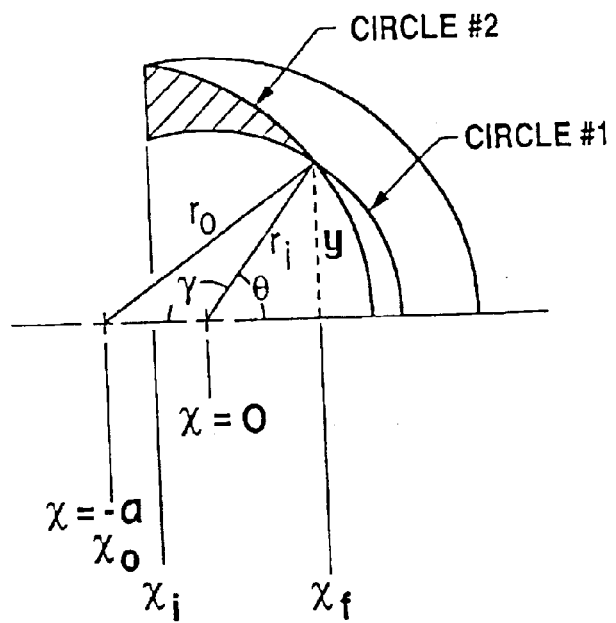

FIG. 16 illustrates the computation in another embodiment in which the area $A_b$ of the hatched portion 16 is determined by the equation $A_b = A_2 - A_1$     Eq. [14]

FIG. 17 is a plot of $A_a$ expressed as a fraction of the initial area of the sensitive volume for x<1.5 mm. This plot is for a preferred embodiment of the NMR MWD tool for which the sensitive volume has a nominal diameter of 13.5 inches and a thickness of 1.5 mm.

Figure 37:
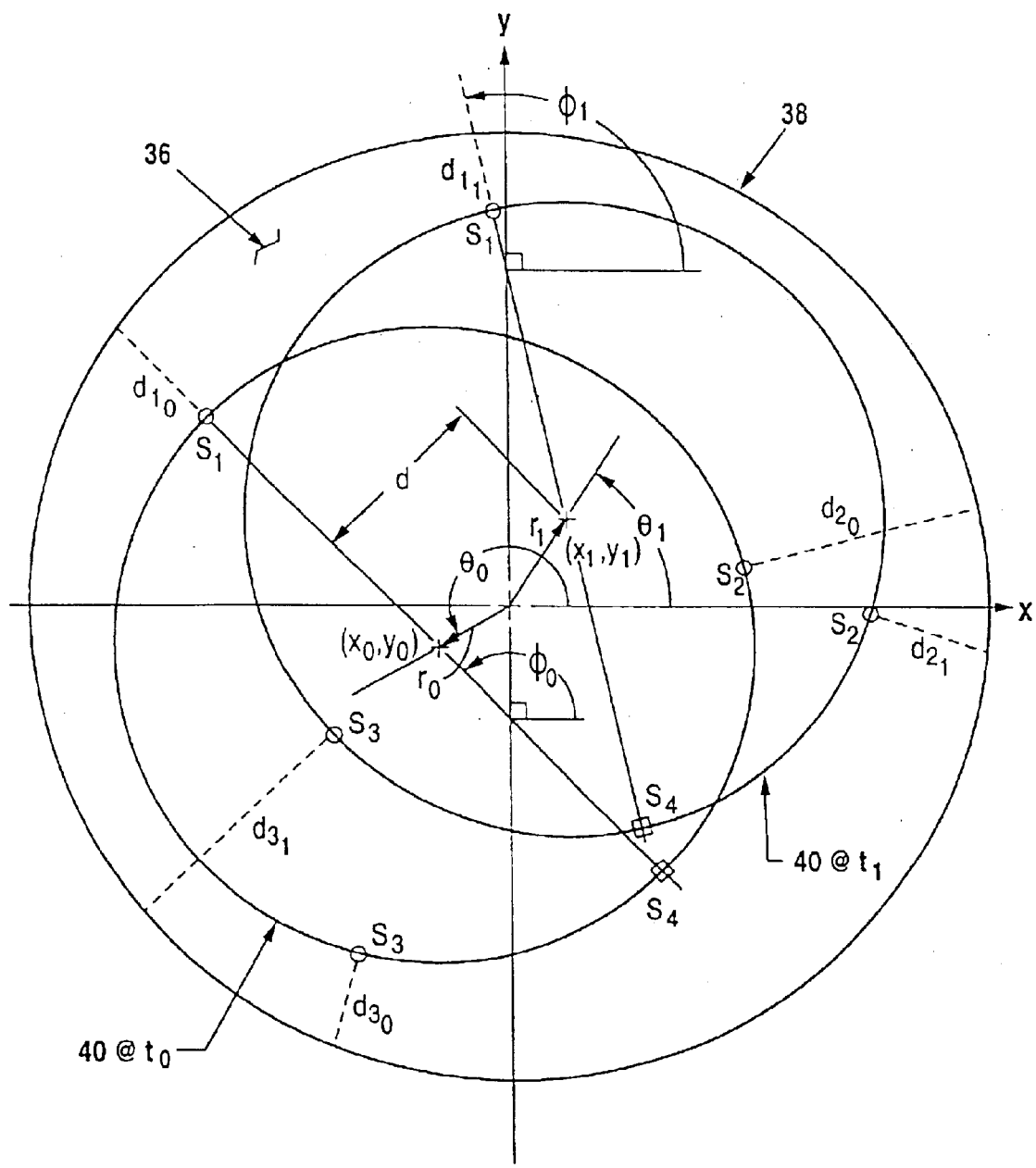
FIG. 37 is a schematic cross-sectional view depicting two positions of an apparatus shown in any of FIGS. 29 through 32.
Figure 38:
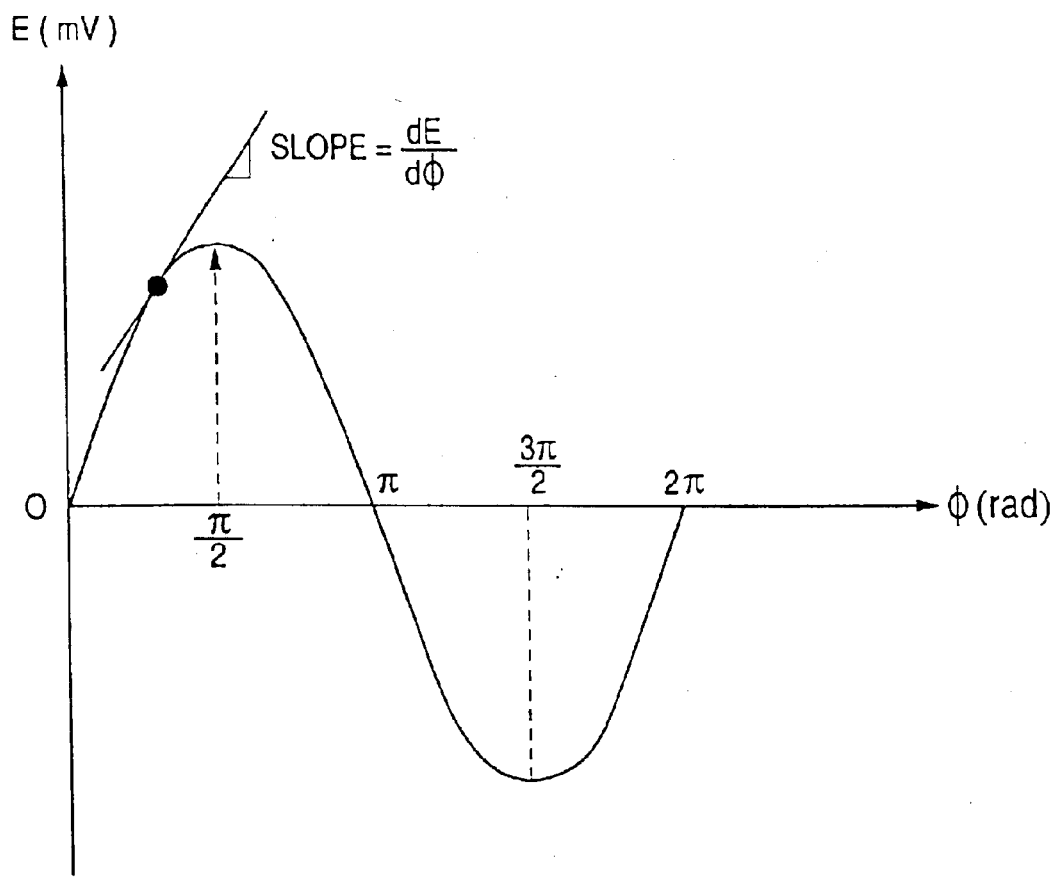
FIG. 38 is a graph showing the sinusoidal variation of the electrical signal generated by either the magnetometer or inclinometer, as appropriate, in an apparatus shown in any of FIGS. 29 through 32.

If the sampling rates of the acoustic sensors 26 or contact sensors 46, as the case may be, do not exceed the rotation speed of the tool 40 by a sufficient margin, then the rotation of the tool 40 is no longer negligible with respect to the lateral displacement. In such cases, at least three acoustic sensors 26 or contact sensors 46 must be used in conjunction with either an inclinometer 48 or magnetometer 50 (FIGS. 29 to 32). Referring to FIG. 37, the acoustic sensors 26 or contact sensors 46 are represented by the symbols $S_1$, $S_2$, and $S_3$, which are preferably spaced uniformly (i.e., 120 degrees apart) around the perimeter of the tool 40, as shown. The inclinometer 48 or magnetometer 50 is represented by the symbol $S_4$ (hereafter referred to as instrument $S_4$). For convenience, the location of instrument $S_4$ is taken to be opposite sensor $S_1$. The sensors $S_1$, $S_2$, and $S_3$ yield displacement measurements $d_1$, $d_2$, and $d_3$, which provide an estimate of the diameter of the borehole 36. As the tool 40 rotates, the instrument $S_4$ produces a sinusoidal electrical signal, E, as a function of the rotational position, f, of the tool 40 within the borehole 36 (FIGS. 37 and 38). Together with the slope, $dE/d\phi$, of the curve in FIG. 38, the value of E determines the angle $\phi$. The coordinate system (x,y) in FIG. 33 is fixed to the borehole 36, but the actual orientation of this coordinate system within the borehole is arbitrary. For convenience, the coordinate system (x,y) has been chosen such that the peak electrical signal, E, occurs when instrument $S_4$ is in the negative y direction (i.e., $\phi=\pi/2$), and the angle $\phi$ is referenced from the x axis according to the right hand rule. The values of $d_1$, $d_2$, $d_3$, and $\phi$ determine the location of the center of the tool 40 within the borehole 36, which may be described in either rectangular coordinates (x,y) or radial coordinates (r,θ), as shown in FIG. 33. By measuring the location $(x_0,y_0)$ and $(x_1,y_1)$ of the center of the tool 40 at two successive times $t_0$ and $t_1$, the lateral displacement, d, of the tool 40 may be calculated as follows:

$$d=[(x_1-x_0)^2+(y_1-y_0)^2]^{1/2} \qquad \text{Eq.[15]}$$

The lateral displacement, d, may then be used to correct the NMR signal, as discussed above. Alternatively, the components of the lateral velocity ($V_x$ and $V_y$) the lateral velocity ($V_L$), and the rotation speed (RPM) of the tool 40 may be calculated by the following equations $$V_x=(x_1-x_0)/(t_1-t_0) \qquad \text{Eq. [16]}$$

$$V_y=(y_1-y_0)/(t_1-t_0) \qquad \text{Eq. [17]}$$

$$V_L=[(V_x)^2+(V_y)^2]^{1/2} \qquad \text{Eq. [18]}$$

$$RPM=(60/2\pi)*(\phi_1-\phi_0)/(t_1-t_0) \qquad \text{Eq. [19]}$$

for use in the motion management algorithm of FIG. 9.

Persons skilled in the art will recognize that a potential difficulty exists for either an inclinometer 48 or magnetometer 50 in certain orientations of the tool 40. Specifically, if instrument $S_4$ is an inclinometer, the electrical signal, E, will be constant rather than sinusoidal if the inclinometer is in a vertical orientation. Similarly, if instrument $S_4$ is a magnetometer, the electrical signal, E, will be constant rather than sinusoidal if the magnetometer is aligned with the earth s magnetic field. In either case, the consequence of a constant electrical signal, E, is that the angle $\phi$ is not determinable, which precludes the calculation of the lateral displacement and rotation speed of the tool 40. This potential difficulty may be eliminated by including both an inclinometer 48 and a magnetometer 50 in the tool 40 so that, for any orientation of the tool 40 within the earth, at least one of the two instruments will produce a sinusoidal electrical signal, E.

NMR Signal Processing Using Motion Management

Figure 36:
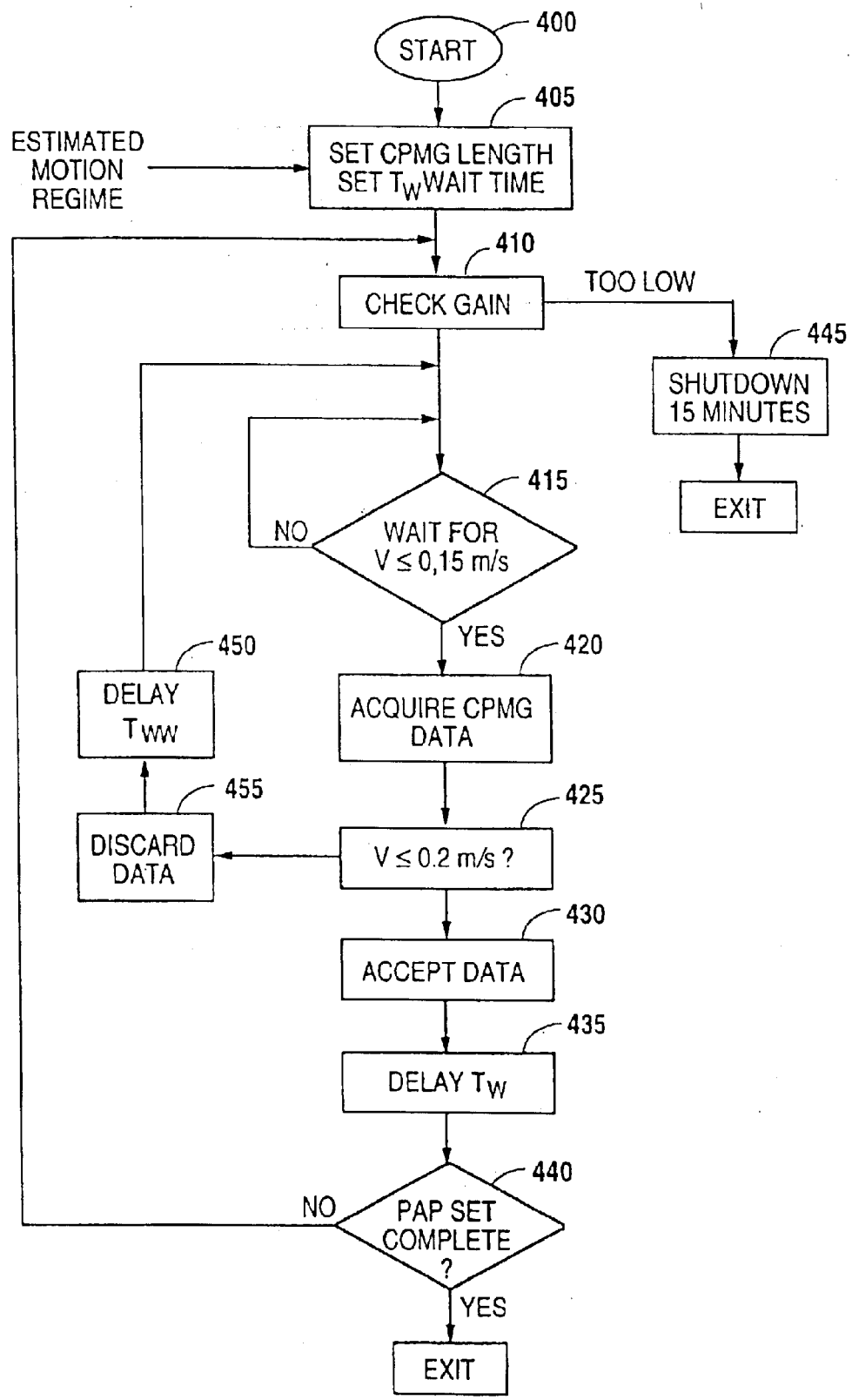
FIG. 36 shows the NMR data acquisition algorithm used by the signal processor of FIG. 33.

The preferred method for collecting NMR data during motion is shown as a flow chart in FIG. 36. It is assumed that the principal motion regime has been determined according to the algorithm illustrated in FIG. 9. In accordance with the present invention at the start 400 of the algorithm this information allows to optimally select the length of the CPMG pulse train and the wait time between CPMG pulse/echo measurements in block 405. As a safety measure, prior before pulsing the transmitter, the system gain is determined at 410 by injecting a reference signal into auxiliary coil (See FIG. 5). If the received signal returned through the main antenna 14 is too low, the tool shuts down at 445 for a predetermined time, e.g., 15 minutes. Otherwise, the actual CPMG sequence is delayed at 415 until a suitable time window with an instantaneous lateral velocity of less than 0.15 m/s occurs. In the stationary and normal drilling modes, this condition should always be met.

Next, a CPMG pulse-echo sequence of pre-determined length is broadcast and echo data are acquired at 420, as known in the art. After every CPMG sequence, the lateral velocity is re-checked at 425. If it exceeds 0.2 m/s, the newly acquired data is discarded at 455 and the tool delays by a pre-determined time $T_{ww}$ at 450. Typically, $T_{ww}$ is shorter than $T_w$ to take advantage of the fact that the tool moved to a fresh volume. After $T_{ww}$ seconds, the search for a suitable time window resumes at 415 as shown in FIG. 36.

If the check at 425 indicates valid data, the data set is accepted at 430; the tool delays for the pre-determined time $T_w$ are set at 435, and the cycle repeats with the acquisition of the second half of a PAP. Once the PAP set is complete, at 440 the algorithm exits.

As noted above, the beneficial effect of phase-alternated signal averaging is achieved in accordance with the present invention by coherent accumulation of NMR data, coupled with the progressive suppression of non-NMR artifacts. Most of the latter is comprised of pulse-induced magneto-acoustic ringing from metallic and magnetic structures within the tool. It has been determined by experimentation that the patterns of said artifacts tend to change cyclically with the tool's orientation and bending.

With reference back to FIG. 32, in a preferred embodiment the signal processor 30 derives an estimate of the tool's orientation from the set of motion sensors, in particular from magnetic pick-up of the earth's magnetic field and/or from the gravity component of the accelerometer data. Within the time windows imposed by the lateral motion, processor 30 attempts to synchronize the NMR measurement with the rotation of the tool string. Under normal drilling conditions, lateral velocities are almost always within acceptable limits and rotational synchronization tends to dominate the time sequencing of the NMR data collection. Under whirling conditions, the opportunities for synchronizing the NMR measurement to the tool orientation start to disappear. If the time windows derived from lateral velocities drop under a pre-determined value, processor 30 no longer attempts synchronization based on tool orientation.

While the foregoing has described and illustrated aspects of various embodiments of the present invention, those skilled in the art will recognize that alternative components and techniques, and/or combinations and permutations of the described components and techniques, can be substituted for, or added to, the embodiments described herein, It is intended, therefore, that the present invention not be defined by the specific embodiments described herein, but rather by the appended claims, which are intended to be construed in accordance with the following well-settled principles of claim construction: (a) Each claim should be given its broadest reasonable interpretation consistent with the specification; (b) Limitations should not be read from the specification or drawings into the claims (e.g., if the claim calls for "antenna", and the specification and drawings show a coil, the claim term "antenna" should not be limited to a coil, but rather should be construed to cover any type of antenna); (c) The words "comprising", "including", and "having" are always open-ended, irrespective of whether they appear as the primary transitional phrase of a claim or as a transitional phrase within an element or subelement of the claim; (d) The indefinite articles "a" or "an" mean one or more; where, instead, a purely singular meaning is intended, a phrase such as "one", "only one", or "a single", will appear; (e) Words in a claim should be given their plain, ordinary, and generic meaning, unless it is readily apparent from the specification that an unusual meaning was intended; (f) an absence of the specific words "means for" connotes applicants' intent not to invoke 35 U.S.C. § 112 (6) in construing the limitation; (g) Where the phrase "means for" precedes a data processing or manipulation "function," it is intended that the resulting means-plus-function element be construed to cover any, and all, computer implementation(s) of the recited "function"; (h) a claim that contains more than one computer-implemented means-plus-function element should not be construed to require that each means-plus-function element must be a structurally distinct entity (such as a particular piece of hardware or block of code); rather, such claim should be construed merely to require that the overall combination of hardware/firmware/software which implements the invention must, as a whole, implement at least the function(s) called for by the claim's means-plus-function element(s); (i) a means-plus-function element should be construed to require only the "function" specifically articulated in the claim, and not in a way that requires additional "functions" which may be described in the specification or performed in the preferred embodiment(s); (j) The existence of method claims that parallel a set of means-plus-function apparatus claims does not mean, or suggest, that the method claims should be construed under 35 U.S.C. § 12 (6).

What is claimed is:

1. A nuclear magnetic resonance (NMR) logging tool for conducting measurements of a down hole formation, comprising:
   (a) a permanent magnet having longitudinal axis;
   (b) a nonmagnetic metal drill collar surrounding the permanent magnet;
   (c) an antenna mounted on the outside of said drill collar; and
   (d) one or more soft-magnetic elements installed in proximate relationship with the antenna, said soft-magnetic elements shaping radio frequency (RF) fields generated by the antenna;
   (e) a motion detector generating signals corresponding to motions of the NMR logging tool.

2. The NMR tool of claim 1 further comprising a down hole signal processor for processing NMR signals from said formation.

3. The NMR tool of claim 1 further comprising a drill bit for drilling a borehole in said down hole formation.

4. The NMR tool of claim 1 further comprising one or more pre-polarization magnets positioned proximate said permanent magnet along its longitudinal axis.

5. The NMR tool of claim 4 comprising two pre-polarization magnets each prepolarization magnet positioned at an end of said permanent magnet.

6. The NMR tool of claim 1, wherein said permanent magnet comprises a plurality of magnet segments.

7. The NMR tool of claim 6, wherein said plurality of magnet segments is made of rare earth materials.

8. The NMR tool of claim 1 further comprising one or more auxiliary antennas to enable sampling of radio frequency (RF) flux from the antenna.

* * * * *